US010973763B2

(12) United States Patent
Narain et al.

(10) Patent No.: US 10,973,763 B2
(45) Date of Patent: Apr. 13, 2021

(54) INHALABLE PHARMACEUTICAL COMPOSITIONS

(75) Inventors: Niven Rajin Narain, Cambridge, MA (US); John Patrick McCook, Frisco, TX (US)

(73) Assignee: Berg LLC, Framingham, MA (US)

(*) Notice: Subject to any disclaimer, the term of this patent is extended or adjusted under 35 U.S.C. 154(b) by 461 days.

(21) Appl. No.: 13/526,333

(22) Filed: Jun. 18, 2012

(65) Prior Publication Data
US 2012/0321698 A1 Dec. 20, 2012

Related U.S. Application Data

(60) Provisional application No. 61/498,505, filed on Jun. 17, 2011.

(51) Int. Cl.
*A61K 9/127* (2006.01)
*A61K 9/12* (2006.01)
(Continued)

(52) U.S. Cl.
CPC .............. *A61K 9/12* (2013.01); *A61K 9/0078* (2013.01); *A61K 9/127* (2013.01); *A61K 31/122* (2013.01);
(Continued)

(58) Field of Classification Search
CPC ........ A61K 9/12; A61K 9/0078; A61K 9/127; A61K 31/122; A61K 9/0073; A61K 47/24; G01N 15/0205; G01N 15/0211; G01N 2015/0038; Y10T 29/49716; A61P 9/12; A61P 7/10; A61P 37/08; A61P 37/00; A61P 35/00; A61P 31/10; A61P 31/06; A61P 31/04; A61P 29/00; A61P 25/00; A61P 21/04; A61P 21/02; A61P 21/00; A61P 11/16; A61P 11/06; A61P 11/00
(Continued)

(56) References Cited

U.S. PATENT DOCUMENTS 4,515,736 A 5/1985 Deamer
4,525,350 A 6/1985 Casey et al.
(Continued)

FOREIGN PATENT DOCUMENTS

CA 2553690 A1 8/2005
CA 2680825 A1 9/2008
(Continued)

OTHER PUBLICATIONS

Bliznakov, E., "Effect of Stimulation of the Host Defense System* by Coenzyme Q10 on Dibenzpyrene-Induced Tumors and Infection with Friend Leukemia Virus in Mice", Proc. Nat. Acad. Sci. USA, 70(2): 390-394 (Feb. 1973).
(Continued)

*Primary Examiner* — Gollamudi S Kishore
(74) *Attorney, Agent, or Firm* — McCarter & English, LLP; Jill A. Mello

(57) ABSTRACT

Inhalable pharmaceutical compositions can include an aqueous dispersion of particles including a hydrophobic bioactive agent (e.g., CoQ10) suitable for continuous aerosolization. Due to their chemical composition and methods of manufacture, the pharmaceutical compositions exhibit distinctive physicochemical properties that provide advantageous aerosol transmission and output.

56 Claims, 49 Drawing Sheets

(51) Int. Cl.
*A61K 31/122* (2006.01)
*A61K 9/00* (2006.01)
*G01N 15/02* (2006.01)
*G01N 15/00* (2006.01)

(52) U.S. Cl.
CPC ..... *G01N 15/0205* (2013.01); *G01N 15/0211* (2013.01); *G01N 2015/0038* (2013.01); *Y10T 29/49716* (2015.01)

(58) Field of Classification Search
USPC ......................................................... 424/450
See application file for complete search history.

(56) References Cited

U.S. PATENT DOCUMENTS

| | | | |
|---|---|---|---|
| 4,636,381 A | 1/1987 | Takada et al. | |
| 4,654,373 A | 3/1987 | Bertelli | |
| 4,824,669 A | 4/1989 | Folkers et al. | |
| 4,895,727 A | 1/1990 | Allen | |
| 5,015,483 A | 5/1991 | Haynes et al. | |
| 5,045,559 A | 9/1991 | Scott | |
| 5,192,528 A * | 3/1993 | Radhakrishnan et al. | 424/45 |
| 5,220,042 A | 6/1993 | Iwaki et al. | |
| 5,362,494 A | 11/1994 | Zysman et al. | |
| 5,378,461 A | 1/1995 | Neigut | |
| 5,539,021 A | 7/1996 | Pate et al. | |
| 5,569,464 A | 10/1996 | Endo et al. | |
| 5,602,184 A | 2/1997 | Myers et al. | |
| 5,603,958 A | 2/1997 | Morein et al. | |
| 5,651,991 A | 7/1997 | Sugiyama et al. | |
| 5,688,842 A | 11/1997 | Pate, III et al. | |
| 5,700,482 A | 12/1997 | Frederiksen et al. | |
| 5,700,653 A | 12/1997 | Lu et al. | |
| 5,738,868 A | 4/1998 | Shinkarenko | |
| 5,770,222 A | 6/1998 | Unger et al. | |
| 5,876,737 A | 3/1999 | Schonrock et al. | |
| 5,889,062 A | 3/1999 | Hoppe et al. | |
| 5,891,465 A | 4/1999 | Keller et al. | |
| 5,900,230 A | 5/1999 | Cutler | |
| 5,912,272 A | 6/1999 | Hoppe et al. | |
| 5,944,012 A | 8/1999 | Pera | |
| 5,962,243 A | 10/1999 | Brown et al. | |
| 6,005,086 A | 12/1999 | Evans et al. | |
| 6,048,566 A | 4/2000 | Behnam et al. | |
| 6,048,886 A | 4/2000 | Neigut | |
| 6,054,261 A | 4/2000 | Masterson | |
| 6,071,495 A | 6/2000 | Unger et al. | |
| 6,107,276 A | 8/2000 | Carli et al. | |
| 6,184,353 B1 | 2/2001 | Evans et al. | |
| 6,197,349 B1 | 3/2001 | Westesen et al. | |
| 6,200,550 B1 | 3/2001 | Masterson et al. | |
| 6,228,891 B1 | 5/2001 | Enzmann et al. | |
| 6,261,575 B1 | 7/2001 | Hoppe et al. | |
| 6,300,377 B1 | 10/2001 | Chopra | |
| 6,303,582 B1 | 10/2001 | Eljamal et al. | |
| 6,334,999 B1 | 1/2002 | Gilbert et al. | |
| 6,346,233 B1 | 2/2002 | Knight et al. | |
| 6,372,234 B1 | 4/2002 | Deckers et al. | |
| 6,403,116 B1 | 6/2002 | Anderson et al. | |
| 6,403,117 B1 | 6/2002 | Sprott et al. | |
| 6,416,957 B1 | 7/2002 | Evans et al. | |
| 6,417,233 B1 | 7/2002 | Sears et al. | |
| 6,441,050 B1 | 8/2002 | Chopra | |
| 6,461,593 B1 | 10/2002 | Hanioka et al. | |
| 6,468,552 B1 | 10/2002 | Stahl et al. | |
| 6,479,058 B1 | 11/2002 | McCadden | |
| 6,482,943 B1 | 11/2002 | Blokhin et al. | |
| 6,503,523 B2 | 1/2003 | Hoppe et al. | |
| 6,506,915 B1 | 1/2003 | West | |
| 6,511,800 B1 | 1/2003 | Singh | |
| 6,531,117 B2 | 3/2003 | Heger et al. | |
| 6,573,284 B1 | 6/2003 | Riley et al. | |
| 6,576,660 B1 | 6/2003 | Liao et al. | |
| 6,576,678 B1 | 6/2003 | Bruening et al. | |
| 6,582,710 B2 | 6/2003 | Deckers et al. | |
| 6,582,723 B2 | 6/2003 | Gorsek | |
| 6,596,287 B2 | 7/2003 | Deckers et al. | |
| 6,599,513 B2 | 7/2003 | Deckers et al. | |
| 6,623,746 B1 | 9/2003 | Wadle et al. | |
| 6,630,160 B1 | 10/2003 | Evans et al. | |
| 6,652,837 B1 * | 11/2003 | Edwards | A61K 9/0075 424/45 |
| 6,652,891 B2 | 11/2003 | Selzer | |
| 6,656,928 B1 | 12/2003 | McCadden | |
| 6,663,886 B2 | 12/2003 | Nagy et al. | |
| 6,686,485 B2 | 2/2004 | West | |
| 6,696,082 B2 | 2/2004 | McCully | |
| 6,696,484 B2 | 2/2004 | Liao et al. | |
| 6,699,464 B1 | 3/2004 | Popp et al. | |
| 6,727,234 B2 | 4/2004 | Wiemer et al. | |
| 6,733,790 B1 | 5/2004 | Garces Garces | |
| 6,740,338 B1 | 5/2004 | Chopra | |
| 6,753,325 B2 | 6/2004 | Rosenbloom | |
| 6,756,062 B2 | 6/2004 | Johnston et al. | |
| 6,803,193 B1 | 10/2004 | Hopper et al. | |
| 6,806,069 B2 | 10/2004 | Chokshi | |
| 6,809,176 B2 | 10/2004 | Blokhin et al. | |
| 6,811,767 B1 | 11/2004 | Bosch et al. | |
| 6,862,890 B2 | 3/2005 | Williams, III et al. | |
| 6,867,024 B2 | 3/2005 | Chokshi | |
| 6,906,106 B2 | 6/2005 | Chevalier | |
| 6,923,988 B2 | 8/2005 | Patel et al. | |
| 7,001,888 B2 | 2/2006 | Tidmarsh et al. | |
| 7,025,955 B2 | 4/2006 | Siddiqui et al. | |
| 7,083,572 B2 | 8/2006 | Unger et al. | |
| 7,083,780 B2 | 8/2006 | Ansmann et al. | |
| 7,091,241 B2 | 8/2006 | Gilloteaux et al. | |
| 7,094,804 B2 | 8/2006 | Behnam | |
| 7,101,536 B2 | 9/2006 | Mongiat et al. | |
| 7,132,268 B2 | 11/2006 | Miyake et al. | |
| 7,147,841 B2 | 12/2006 | Herzog | |
| 7,169,385 B2 | 1/2007 | Fantuzzi et al. | |
| 7,169,590 B2 | 1/2007 | Ueda et al. | |
| 7,176,171 B2 | 2/2007 | Nieendick et al. | |
| 7,179,880 B2 | 2/2007 | Kawa et al. | |
| 7,182,938 B2 | 2/2007 | Andre et al. | |
| 7,198,801 B2 | 4/2007 | Carrara et al. | |
| 7,208,298 B2 | 4/2007 | Miyake et al. | |
| 7,250,174 B2 | 7/2007 | Lee et al. | |
| 7,268,107 B2 | 9/2007 | Nieendick et al. | |
| 7,273,606 B2 | 9/2007 | Fantuzzi et al. | |
| 7,279,456 B2 | 10/2007 | Dufay et al. | |
| 7,311,897 B2 | 12/2007 | Ehlis et al. | |
| 7,318,929 B2 | 1/2008 | Schieferstein et al. | |
| 7,357,918 B2 | 4/2008 | Comte et al. | |
| 7,438,903 B2 | 10/2008 | Parkhideh | |
| 7,794,694 B2 | 9/2010 | Giacomoni et al. | |
| 8,147,825 B2 | 4/2012 | Hsia et al. | |
| 8,337,931 B2 | 12/2012 | Bromley | |
| 8,372,395 B2 | 2/2013 | Yu et al. | |
| 8,454,945 B2 | 6/2013 | McCook et al. | |
| 8,685,446 B2 | 4/2014 | Casana-Giner et al. | |
| 8,753,675 B1 | 6/2014 | Chopra | |
| 8,785,598 B2 | 7/2014 | Chung et al. | |
| 8,815,567 B2 | 8/2014 | Ye | |
| 8,961,958 B2 | 2/2015 | Harris et al. | |
| 9,168,216 B2 | 10/2015 | Gavin et al. | |
| 2001/0021704 A1 | 9/2001 | Ghyczy et al. | |
| 2001/0022965 A1 | 9/2001 | Heger et al. | |
| 2001/0043909 A1 | 11/2001 | SaNogueira et al. | |
| 2002/0039595 A1 | 4/2002 | Keller | |
| 2002/0044913 A1 | 4/2002 | Hamilton | |
| 2002/0048551 A1 * | 4/2002 | Keller et al. | 424/43 |
| 2002/0048559 A1 | 4/2002 | Shinoda et al. | |
| 2002/0049422 A1 | 4/2002 | Brewitt | |
| 2002/0071852 A1 | 6/2002 | Deckers et al. | |
| 2002/0102296 A1 | 8/2002 | Giovanella et al. | |
| 2002/0106337 A1 | 8/2002 | Deckers et al. | |
| 2002/0114820 A1 | 8/2002 | Deckers et al. | |
| 2002/0127252 A1 | 9/2002 | Kramer et al. | |
| 2002/0155151 A1 | 10/2002 | Enzmann et al. | |
| 2002/0156302 A1 | 10/2002 | West | |
| 2002/0182199 A1 | 12/2002 | Hoppe et al. | |

(56) References Cited

U.S. PATENT DOCUMENTS

| | | |
|---|---|---|
| 2003/0012762 A1 | 1/2003 | Zulli et al. |
| 2003/0031688 A1 | 2/2003 | Ghosh et al. |
| 2003/0044441 A1 | 3/2003 | Schmid et al. |
| 2003/0049323 A1 | 3/2003 | Hitt et al. |
| 2003/0077297 A1 | 4/2003 | Chen et al. |
| 2003/0091518 A1 | 5/2003 | Pauly et al. |
| 2003/0104048 A1 | 6/2003 | Patel et al. |
| 2003/0104080 A1 | 6/2003 | Singh et al. |
| 2003/0105030 A1 | 6/2003 | Liao et al. |
| 2003/0105031 A1 | 6/2003 | Rosenbloom |
| 2003/0108493 A1 | 6/2003 | Henry et al. |
| 2003/0113354 A1 | 6/2003 | Schmid et al. |
| 2003/0118576 A1 | 6/2003 | Brancato et al. |
| 2003/0124158 A1 | 7/2003 | Heidenfelder et al. |
| 2003/0129150 A1 | 7/2003 | Pauly et al. |
| 2003/0143166 A1 | 7/2003 | Heger et al. |
| 2003/0144346 A1 | 7/2003 | Liao et al. |
| 2003/0152598 A1 | 8/2003 | Heidenfelder et al. |
| 2003/0161849 A1 | 8/2003 | Heidenfelder et al. |
| 2003/0167556 A1 | 9/2003 | Kelley |
| 2003/0170265 A1 | 9/2003 | Henry et al. |
| 2003/0180231 A1 | 9/2003 | Danoux et al. |
| 2003/0180278 A1 | 9/2003 | Hoppe et al. |
| 2003/0180352 A1 | 9/2003 | Patel et al. |
| 2003/0185865 A1 | 10/2003 | Jentzsch et al. |
| 2003/0190284 A1 | 10/2003 | Annapragada et al. |
| 2003/0215406 A1 | 11/2003 | Schreiner et al. |
| 2003/0219472 A1 | 11/2003 | Pauletti et al. |
| 2004/0028614 A1 | 2/2004 | Corbella et al. |
| 2004/0034107 A1 | 2/2004 | Enzmann |
| 2004/0043045 A1 | 3/2004 | Seipel et al. |
| 2004/0063648 A1 | 4/2004 | Pandol et al. |
| 2004/0067260 A1 | 4/2004 | Milley et al. |
| 2004/0086538 A1 | 5/2004 | Sauermann et al. |
| 2004/0109880 A1 | 6/2004 | Pauly et al. |
| 2004/0110848 A1 | 6/2004 | Peffley et al. |
| 2004/0122109 A1 | 6/2004 | Fujii et al. |
| 2004/0126367 A1 | 7/2004 | Fujii et al. |
| 2004/0137070 A1 | 7/2004 | Scherzer et al. |
| 2004/0142006 A1 | 7/2004 | Bleckmann et al. |
| 2004/0142007 A1 | 7/2004 | Moussou et al. |
| 2004/0142009 A1 | 7/2004 | Ansmann et al. |
| 2004/0151710 A1 | 8/2004 | Bozzacco |
| 2004/0151711 A1 | 8/2004 | West |
| 2004/0167034 A1 | 8/2004 | Coote et al. |
| 2004/0170560 A1 | 9/2004 | Fossheim et al. |
| 2004/0170581 A1 | 9/2004 | Henry et al. |
| 2004/0185071 A1 | 9/2004 | Hatazaki |
| 2004/0191190 A1 | 9/2004 | Pauly et al. |
| 2004/0191263 A1 | 9/2004 | Hageman et al. |
| 2004/0197279 A1 | 10/2004 | Bleckmann et al. |
| 2004/0197354 A1 | 10/2004 | Doring et al. |
| 2004/0208935 A1 | 10/2004 | Giovanella et al. |
| 2004/0219114 A1 | 11/2004 | Andersson et al. |
| 2004/0228910 A1 | 11/2004 | Enzmann et al. |
| 2004/0234559 A1 | 11/2004 | Bleckmann et al. |
| 2004/0258717 A1 | 12/2004 | Sauermann et al. |
| 2005/0000390 A1 | 1/2005 | Nieendick et al. |
| 2005/0008581 A1 | 1/2005 | Parkhideh |
| 2005/0019278 A1 | 1/2005 | Berg-Schultz |
| 2005/0019353 A1 | 1/2005 | Prinz et al. |
| 2005/0036976 A1 | 2/2005 | Rubin et al. |
| 2005/0037036 A1 | 2/2005 | Nielsen et al. |
| 2005/0058610 A1 | 3/2005 | Baschong et al. |
| 2005/0069582 A1 | 3/2005 | Fantuzzi |
| 2005/0070611 A1 | 3/2005 | Fantuzzi |
| 2005/0079164 A1 | 4/2005 | Fantuzzi et al. |
| 2005/0084505 A1 | 4/2005 | Muller et al. |
| 2005/0100537 A1 | 5/2005 | Evans et al. |
| 2005/0106190 A1 | 5/2005 | Kawa et al. |
| 2005/0106199 A1 | 5/2005 | Schreiber et al. |
| 2005/0112156 A1 | 5/2005 | Busch et al. |
| 2005/0118209 A1 | 6/2005 | Jentzsch et al. |
| 2005/0136081 A1 | 6/2005 | Kawa et al. |
| 2005/0142123 A1 | 6/2005 | Chen et al. |
| 2005/0142153 A1 | 6/2005 | Schreiber et al. |
| 2005/0142665 A1 | 6/2005 | Wachtel et al. |
| 2005/0147598 A1 | 7/2005 | Ueda et al. |
| 2005/0152856 A2 | 7/2005 | Andersson et al. |
| 2005/0214333 A1 | 9/2005 | Lanzendoerfer et al. |
| 2005/0214369 A1 | 9/2005 | Ko et al. |
| 2005/0220726 A1 | 10/2005 | Pauly et al. |
| 2005/0220826 A1 | 10/2005 | Kawa et al. |
| 2005/0226824 A1 | 10/2005 | Kawa et al. |
| 2005/0226858 A1 | 10/2005 | Kitamura et al. |
| 2005/0226947 A1 | 10/2005 | Kern |
| 2005/0238679 A1 | 10/2005 | Biergiesser et al. |
| 2005/0255057 A1 | 11/2005 | Andre et al. |
| 2005/0276764 A1 | 12/2005 | Kolbe et al. |
| 2005/0281772 A1 | 12/2005 | Bromley et al. |
| 2005/0287206 A1 | 12/2005 | Fantuzzi et al. |
| 2005/0288378 A1 | 12/2005 | Yan et al. |
| 2006/0002964 A9 | 1/2006 | Schreiber et al. |
| 2006/0002992 A1* | 1/2006 | Schmehl ............ A61K 9/1271 424/450 |
| 2006/0008426 A1 | 1/2006 | Daring et al. |
| 2006/0008482 A1 | 1/2006 | Prinz et al. |
| 2006/0010519 A1 | 1/2006 | Kadowaki et al. |
| 2006/0013888 A1 | 1/2006 | Fantuzzi |
| 2006/0035981 A1 | 2/2006 | Mazzio et al. |
| 2006/0039956 A1 | 2/2006 | Hensen et al. |
| 2006/0051462 A1 | 3/2006 | Wang |
| 2006/0057081 A1 | 3/2006 | Boxrud |
| 2006/0073106 A1 | 4/2006 | Berg-Schultz et al. |
| 2006/0093633 A1 | 5/2006 | Stab et al. |
| 2006/0099158 A1 | 5/2006 | Zander et al. |
| 2006/0121016 A1 | 6/2006 | Lee |
| 2006/0127384 A1 | 6/2006 | Capaccioli et al. |
| 2006/0140970 A1 | 6/2006 | Telerman et al. |
| 2006/0153783 A1 | 7/2006 | Ehlis et al. |
| 2006/0154993 A1 | 7/2006 | Littarru et al. |
| 2006/0188459 A1 | 8/2006 | Heinrichs et al. |
| 2006/0188492 A1 | 8/2006 | Richardson et al. |
| 2006/0193905 A1 | 8/2006 | Ehringer et al. |
| 2006/0198830 A1 | 9/2006 | Shastri et al. |
| 2006/0204447 A1* | 9/2006 | Knight et al. ................. 424/45 |
| 2006/0251690 A1 | 11/2006 | Lipshutz et al. |
| 2006/0251708 A1 | 11/2006 | Chen et al. |
| 2006/0280691 A1 | 12/2006 | Wang et al. |
| 2006/0286046 A1 | 12/2006 | Haber |
| 2006/0292220 A1 | 12/2006 | Giordano et al. |
| 2007/0053985 A1 | 3/2007 | Ueda et al. |
| 2007/0071779 A1 | 3/2007 | McKie |
| 2007/0085059 A1 | 4/2007 | Mora-Gutierrez et al. |
| 2007/0092469 A1 | 4/2007 | Jacobs |
| 2007/0104701 A1 | 5/2007 | Ueda et al. |
| 2007/0104810 A1 | 5/2007 | Kern |
| 2007/0110731 A1 | 5/2007 | Riley |
| 2007/0122349 A1 | 5/2007 | Wachtel et al. |
| 2007/0154498 A1 | 7/2007 | Bortz et al. |
| 2007/0172436 A1 | 7/2007 | Zhang |
| 2007/0184041 A1 | 8/2007 | Burja |
| 2007/0184076 A1 | 8/2007 | Unger et al. |
| 2007/0189994 A1 | 8/2007 | Berg et al. |
| 2007/0196349 A1 | 8/2007 | Kitamura et al. |
| 2007/0196914 A1 | 8/2007 | Murray et al. |
| 2007/0202090 A1 | 8/2007 | Prosek et al. |
| 2007/0218042 A1 | 9/2007 | Khaled |
| 2007/0243180 A1 | 10/2007 | Tanaka et al. |
| 2007/0248590 A1 | 10/2007 | Milne et al. |
| 2007/0253941 A1 | 11/2007 | Naidu et al. |
| 2007/0258966 A1 | 11/2007 | Ueda et al. |
| 2007/0258967 A1 | 11/2007 | Ueda et al. |
| 2007/0259009 A1 | 11/2007 | Linder |
| 2007/0275021 A1 | 11/2007 | Lee et al. |
| 2008/0008694 A1 | 1/2008 | Elgebaly et al. |
| 2008/0020022 A1 | 1/2008 | Udell |
| 2008/0025929 A1 | 1/2008 | Burton et al. |
| 2008/0031862 A1 | 2/2008 | Ghosal |
| 2008/0063674 A1 | 3/2008 | Vollhardt et al. |
| 2008/0069779 A1 | 3/2008 | Tamarkin et al. |
| 2008/0069898 A1 | 3/2008 | Smith et al. |
| 2008/0075684 A1 | 3/2008 | Barg et al. |
| 2008/0081034 A1 | 4/2008 | Zimmerman et al. |

(56) References Cited

U.S. PATENT DOCUMENTS

| | | |
|---|---|---|
| 2008/0081082 A1 | 4/2008 | Zimmerman et al. |
| 2008/0089852 A1 | 4/2008 | Hotz et al. |
| 2008/0089913 A1 | 4/2008 | Kallmayer et al. |
| 2008/0095719 A1 | 4/2008 | Herrmann et al. |
| 2008/0102313 A1 | 5/2008 | Nilsen et al. |
| 2008/0138326 A1 | 6/2008 | Fujii et al. |
| 2008/0207560 A1 | 8/2008 | Harada et al. |
| 2008/0219963 A1 | 9/2008 | Paolo et al. |
| 2008/0233183 A1 | 9/2008 | McCook et al. |
| 2008/0248095 A1* | 10/2008 | Giovanella et al. .......... 424/450 |
| 2008/0254017 A1 | 10/2008 | Kane et al. |
| 2008/0299049 A1 | 12/2008 | Stangl |
| 2008/0299100 A1 | 12/2008 | Hsia et al. |
| 2008/0312128 A1 | 12/2008 | Chaum et al. |
| 2009/0028931 A1* | 1/2009 | Wasan ................ A61K 9/1271 424/450 |
| 2009/0060891 A1 | 3/2009 | Harris et al. |
| 2009/0098200 A1 | 4/2009 | Temtsin Krayz et al. |
| 2009/0183554 A1 | 7/2009 | Grant et al. |
| 2009/0202509 A1 | 8/2009 | Leverve |
| 2009/0246186 A1 | 10/2009 | Shinagawa et al. |
| 2009/0280987 A1 | 11/2009 | Strobel |
| 2010/0047297 A1 | 2/2010 | Petersen |
| 2010/0061969 A1 | 3/2010 | Otsubo et al. |
| 2010/0062048 A1 | 3/2010 | Hsia et al. |
| 2010/0080762 A1 | 4/2010 | Goralczyk |
| 2010/0080785 A1 | 4/2010 | Berl |
| 2010/0098752 A1 | 4/2010 | Pinsky |
| 2010/0099775 A1 | 4/2010 | Schwarz et al. |
| 2010/0119589 A1 | 5/2010 | Selischeva et al. |
| 2010/0129431 A1 | 5/2010 | Schwarz et al. |
| 2010/0189596 A1 | 7/2010 | Deng et al. |
| 2010/0215725 A1 | 8/2010 | Schwarz et al. |
| 2011/0027247 A1 | 2/2011 | Narain et al. |
| 2011/0110914 A1 | 5/2011 | Narain et al. |
| 2011/0142914 A1 | 6/2011 | Persaud et al. |
| 2011/0229554 A1 | 9/2011 | Narain et al. |
| 2011/0318405 A1 | 12/2011 | Erwin |
| 2012/0064136 A1 | 3/2012 | Baker, Jr. et al. |
| 2012/0141446 A1 | 6/2012 | Patel |
| 2012/0141448 A1 | 6/2012 | De Ferra et al. |
| 2012/0164215 A1 | 6/2012 | Hsia et al. |
| 2012/0201801 A1 | 8/2012 | Hsia et al. |
| 2012/0244134 A1 | 9/2012 | Chen et al. |
| 2013/0019860 A1* | 1/2013 | Depla et al. ............. 128/200.14 |
| 2013/0202683 A1 | 8/2013 | McCook et al. |
| 2014/0239525 A1 | 8/2014 | McConville et al. |
| 2015/0023940 A1 | 1/2015 | Narain et al. |
| 2015/0150801 A1 | 6/2015 | Park et al. |
| 2015/0238429 A1 | 8/2015 | Fang et al. |

FOREIGN PATENT DOCUMENTS

| | | | |
|---|---|---|---|
| EP | 1404291 A1 | 4/2004 |
| EP | 1493437 A1 | 1/2005 |
| EP | 1849481 A1 | 10/2007 |
| EP | 1475083 B1 | 12/2007 |
| EP | 1476032 B1 | 4/2008 |
| EP | 1908459 A1 | 4/2008 |
| EP | 1957037 A1 | 8/2008 |
| EP | 1565163 B1 | 2/2012 |
| EP | 2567705 A2 | 3/2013 |
| WO | WO-198601714 A1 | 3/1986 |
| WO | WO-198801862 A1 | 3/1988 |
| WO | WO-9316704 A1 | 9/1993 |
| WO | WO-9617626 A2 | 6/1996 |
| WO | WO-9800111 A1 | 1/1998 |
| WO | WO-1999065469 A2 | 12/1999 |
| WO | 0044862 A1 | 8/2000 |
| WO | 0217879 A1 | 3/2002 |
| WO | WO-02078727 A1 | 10/2002 |
| WO | 2003075820 A1 | 9/2003 |
| WO | WO-2003090682 A2 | 11/2003 |
| WO | WO-2004003564 A2 | 1/2004 |
| WO | 2004035553 A1 | 4/2004 |
| WO | 2004039348 A1 | 5/2004 |
| WO | WO-2005069916 A2 | 8/2005 |
| WO | WO-2005112957 A1 | 12/2005 |
| WO | WO-2006073190 A1 | 7/2006 |
| WO | WO-2006108556 A2 | 10/2006 |
| WO | WO-2007131047 A2 | 11/2007 |
| WO | 2008023264 A2 | 2/2008 |
| WO | WO-2008024020 A1 | 2/2008 |
| WO | WO-2008063341 A2 | 5/2008 |
| WO | WO-2009005215 A1 | 1/2009 |
| WO | WO-2009012718 A1 | 1/2009 |
| WO | 2009/073843 * | 6/2009 |
| WO | WO-2009073843 A1 | 6/2009 |
| WO | WO-2009126764 A1 | 10/2009 |
| WO | WO-2011112900 A2 | 9/2011 |
| WO | 2012161562 A1 | 11/2012 |
| WO | 2013175266 A1 | 11/2013 |
| WO | 2014138922 A1 | 9/2014 |
| WO | 2015127537 A1 | 9/2015 |
| WO | 2015157455 A1 | 10/2015 |

OTHER PUBLICATIONS

Bliznakov et al., "Coenzymes Q: Stimulants of the Phagocytic Activity in Rats and Immune Response in Mice", Experientia, 26(9): 953-954 (Sep. 1970).

Hodges et al., "CoQ10: could it have a role in cancer management?", BioFactors, vol. 9, pp. 365-370 (1999).

International Preliminary Report on Patentability issued in PCT/US2008/085669 dated Jun. 17, 2010.

International Search Report from Application No. PCT/US2007/068052 dated Apr. 15, 2008.

International Search Report from Application No. PCT/US2008/057786 dated Oct. 23, 2008.

International Search Report issued in PCT/US2012/042999 dated Aug. 14, 2012.

International Search Report issued in PCT/US2012/043001 dated Oct. 17, 2012.

International Search Report of International Application No. PCT/US2010/034453 dated Jan. 31, 2011.

Johnson et al., "Aerosolization and Hygroscopic Growth Evaluation of Lyophilized Liposome Aerosols Under Controlled Temperature and Relative Humidity Conditions," Aerosol Science and Technology, 1996, vol. 25, (1): pp. 22-30.

Kokawa et al., "Coenzyme Q10 in cancer chemotherapy-experimental studies on augmentation of the effects of masked compounds, especially in the combined chemotherapy with immunopotentiators", Gan To Kagayu Ryoho. Cancer and Chemotherapy, Mar. 1993, vol. 10, No. 3, pp. 768-774. XP002473825, Abstract. (Article in Japanese).

Lockwood et al., "Apparent partial remission of breast cancer in 'high risk' patients supplemented with nutritional antioxidants, essential fatty acids and coenzyme Q10", Mol-Aspects-Med., vol. 15 Suppl. pp. 231-240 (1994) (Abstract Only).

Lockwood et al., "Partial and complete regression of breast cancer in patients in relation to dosage of coenzyme Q10", Biochem-Biophys-Res-Commun., 199(3), pp. 1504-1508 (1994) (Abstract Only).

Lockwood et al., "Progress on Therapy of Breast Cancer with Vitamin Q10 and the Regression of Metastases", Biochem-Biophys-Res-Commun. 212(1) pp. 172-177 (1995) (Abstract Only).

Mura et al., "Evaluation of transcutol as a clonazepam transdermal permeation enhancer from hydrophillic gel formulations," Eur. J. Pharm. Sci., 2000, 9: 365-372.

Panwar et al, "Preparation, characterization, and in vitro release study of albendazole-encapsulated nanosize liposomes. 2010, International Journal of Nanomedicine, 5: 101-108".

Rastogi, "Analytical control of preservative labelling on skin creams," Contact Dermatitis, 2000, 43: 339-343, Abstract.

Supplemental European Search Report issued in European Patent Application No. 08857192.2 dated Sep. 6, 2013.

Supplementary European Search Report from Application No. EP 05 71 1599 dated Apr. 10, 2008.

(56) References Cited

OTHER PUBLICATIONS

Zhang et al, Preparation and Physico-chemical Property of Coenzyme Q10 Submicroemulsion, 2007, China Pharmacy, 18 (19): 1476-1478.

Zucker et al., "Liposome drug's loading efficiency: a working model based on loading conditions and drug's physicochemical properties. 2009, Journal of Controlled Disease, 139: 73-80".

Owens, Donald E. III, et al., Opsonization, biodistribution, and pharmacokinetics of polymeric nanoparticles, International Journal of Pharmaceutics, 307(1):93-102, 2006.

Trosko, J.E., Mutation Research, 480-481, pp. 219-229, 2001.

International Search Report and Written Opinion of the International Searching Authority issued for PCT/US2011/028042, dated Nov. 24, 2011.

Gura, "Systems for identifying new drugs are often faulty," Science, 1997,278(5340): 1041-1042.

Frijohff et al., "Advances in Molecular Carcinogenesis: Current and Future Use of Mouse Models to Screen and Validate Molecularly Targeted Anticancer Drugs," Molecular Carcinogenesis, 2004, 39: 183-194.

Lesperance et al., "Mega-dose vitamins and minerals in the treatment of non-metastatic breast cancer: an historical cohort study," Breast Cancer Res. Treat., 2002, 76: 137-143, Abstract.

* cited by examiner

Vacuum Source

Laser beam

Air Sheath

Nebulizer output

↑ Suction airflow rate: 30 L/min
▫ Sheath airflow rate: 15 L/min
◌ Droplet of CoQ10 dispersion

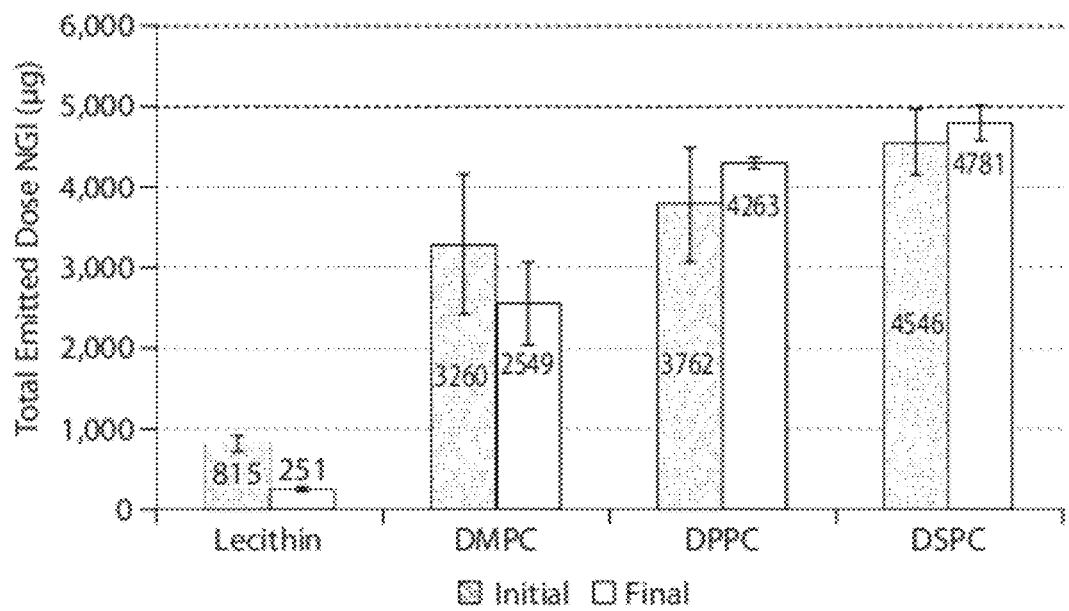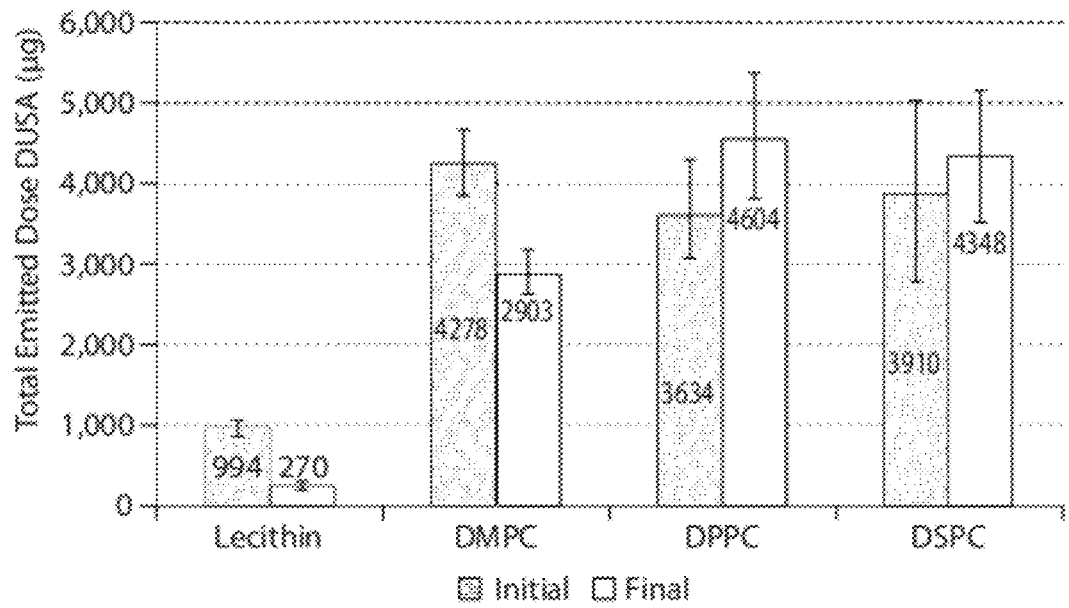
Fig. 29A

Table 1

| Formulation | Test | Phospholipids Type(s) | Hydration | Number of passes | Characterization |
|---|---|---|---|---|---|
| A | Number of passes; stability | Lecithin | ~1 hour, no stirring | 20, 50, 70 and 100 | Particle size distribution |
| B | Number of passes; type of phospholipids | Lecithin and DPPC | ~1 hour, no stirring | 10, 20, 30, 40 and 50 | Particle size distribution |
| C* | Nebulization performance | Lecithin | Overnight, stirring | 10, 30, and 50 | Particle size distribution, surface tension, rheology, zeta potential, and TAO. |

*0.9% w/v added to final formulation following processing with microfluidizer.
DPPC: dipalmitoylphosphatidylcholine; TAO: Total Aerosol Output.

Table 1

FIG. 42

| Manufacturing Process | $Dv_{(50)}$ (µm) | Span Value |
|---|---|---|
| Shear Force | 1.03 | 2.076 |
| Microfluidization | 0.63 | 0.367 |
| Ultrasonication | 0.71 | 0.459 |

Table 2

FIG. 43

| Formulation | $Dv_{(10)}$ (µm) | $Dv_{(50)}$ (µm) | $Dv_{(90)}$ (µm) |
|---|---|---|---|
| Lecithin | 0.24 ± 0.00 | 0.45 ± 0.00 | 0.81 ± 0.00 |
| DMPC | 0.21 ± 0.01* | 0.81 ± 0.14 | 37.84 ± 27.25 |
| DPPC | 0.22 ± 0.01 | 0.85 ± 0.10 | 36.30 ± 34.26 |
| DSPC | 0.25 ± 0.02* | 0.41 ± 1.93 | 97.24 ± 103.06 |

Results are expressed as means ± standard deviations (n = 3).
* $P>0.05$ following Tukey-Kramer test.

Table 3

FIG. 44

| Model | Equation |
|---|---|
| Cross | $\dfrac{\eta - \eta_\infty}{\eta_0 - \eta_\infty} = \dfrac{1}{(1 + (K \cdot \dot{\gamma})^m)}$ |
| Sisko | $\eta = \eta_\infty + K \cdot \dot{\gamma}^{n-1}$ |
| Williamson | $\eta = \dfrac{\eta_0}{(1 + (K \cdot \dot{\gamma})^n)}$ |

$\eta_0$ and $\eta_\infty$ are the asymptotic values of viscosity at very low (zero-rate viscosity) and very high (infinite-rate viscosity) shear rates; $K$ is the characteristic time (the lower the value, the further to the right the curve lies); $m$ is a dimensionless constant indicating rheological behavior (viscosity as a function of shear rate) in the shear thinning region where $m = 0$ refers to Newtonian behavior and increasing values tending to unity corresponds to increasing shear thinning behavior; $n$ is the power-law index and values below and above unity represent shear-thinning and shear thickening events, respectively; and $\dot{\gamma}$ is shear rate.

Table 4

FIG. 45

| Formulation | Model | Zero-rate viscosity (mPa.s)[§] | Infinite-rate viscosity (mPa.s) | Characteristic time (s) | Rate index (n) or Cross rate constant (m) | Thixotropy (Pa/s) | Normalized Thixotrpy (s⁻¹) |
|---|---|---|---|---|---|---|---|
| Lecithin | Sisko | N/A | 0.95 ± 0.01 | 8.60×10⁻⁴ ± 14.9×10⁻⁴ | 23.35 ± 1.90* | 85.48 ± 0.79* | 16.92×10⁻⁴ ± 0.31×10⁻⁴ |
| DMPC | Cross | 1.13 ± 0.01 | 3.66 ± 3.11 | 9.06×10⁻⁴ ± 5.38×10⁻⁴ | 2.59 ± 0.52 | Zero | Zero |
| DMPC | Cross | 5.31 ± 0.96 | 1.61 ± 0.01 | 0.51 ± 0.03 | 0.70 ± 0.05 | Zero | Zero |
| DSPC | Williamson | 621.17 ± 446.30 | N/A | 15.19 ± 11.12* | 0.54 ± 0.10 | Zero | Zero |

Results are expressed as means ± standard deviations (n = 3). N/A: not applicable when referred to this rheological model (compare to equations in table 2). § Groups are statistically different but post hoc test was unable to distinguish differences among groups. * P < 0.05 when compared to other formulations.

Table 5

FIG. 46

| Formulation | FPD$_{et}$ (mg) | FPD$_r$ (μg/min) |
|---|---|---|
| Lecithin | 24.84 | 1656 |
| DMPC | 126.30 | 8420 |
| DPPC | 168.36 | 11224 |
| DSPC | 173.79 | 11586 |

Table 6

FIG. 47

| Formulation | FPD$_r$ (mg/min) | Mouse weight (g) | RMV (mL/min) | Estimated Dose After 15 minutes of nebulization (mg) | Estimated Dose Normalized to body weight (mg/kg) |
|---|---|---|---|---|---|
| DMPC | 8.420 | 28.8 ± 1.4 | 38.50 | 4.787 | 166.2 |
| DPPC | 11.224 | 26.1 ± 1.5 | 36.07 | 5.980 | 229.1 |
| DSPC | 11.586 | 29.5 ± 2.0 | 39.11 | 6.693 | 226.9 |

Results of mouse weight are expressed as mean ± standard deviations (n = 36 per group). FPD$_r$ is the rate of delivery of the Fine Particle Dose (the amount of particles with aerodynamic cutoff diameter below 5.39 μm per minute) and RMV is the Rate Minute Volume calculated based on 10 mL/kg at 120 breaths per minute.[21]

Table 7

FIG. 48

| Pharmacokinetic Parameter | DMPC | DPPC | DSPC |
|---|---|---|---|
| $C_{max}$ (µg/g wet tissue) | 777.7 | 604.0 | 791.3 |
| $t_{max}$ (h) | 1 | 1 | 1 |
| $AUC_{0-48}$ (mg-h/g) | 28.228 | 21.144 | 26.830 |

Table 8

FIG. 49

| Number of passes | Lecithin (test run) | | DPPC (n=3) | |
|---|---|---|---|---|
| | APT (%) | TAO (%) | APT (%) | TAO (%) |
| 10 | 94.8 | 11 | 94.3 ± 1.8 | 50.0 ± 9.3 |
| 20 | 99.3 | 0 | 81.9 ± 1.4 | 69.6 ± 12.1 |
| 30 | 97.1 | 10.5 | 87.7 ± 1.0 | 70.4 ± 3.0 |
| 40 | 94.2 | 21 | 77.8 ± 3.2 | 76.4 ± 3.4 |
| 50 | 90 | 30 | 86.8 ± 1.1 | 78.0 ± 8.7 |

| Form. | Number of Cycles | Following Preparation | | After 7 days | |
|---|---|---|---|---|---|
| | | APT (%) | TAO (%) | APT (%) | TAO (%) |
| 1 | 20 | 97.1 ± 3.4 | 16.4 ± 15.2 | 85.4 ± 3.5** | 75.1 ± 9.0** |
| 2 | 50 | 77.9 ± 12.6 | 85.6 ± 15.1* | 89.1 ± 2.0 | 66.7 ± 5.3 |
| 3 | 70 | 85.8 ± 1.5* | 72.0 ± 4.4* | 91.5 ± 0.5** | 56.4 ± 0.4** |
| 4 | 100 | 86.8 ± 0.6* | 67.8 ± 1.0* | 91.7 ± 0.2** | 52.7 ± 1.8** |

Table 9

FIG. 50

INHALABLE PHARMACEUTICAL COMPOSITIONS

CROSS REFERENCE TO RELATED APPLICATIONS

This application claims benefit of priority to U.S. Provisional Application No. 61/498,505 filed Jun. 17, 2011, the disclosure of which is hereby incorporated by reference in its entirety.

FIELD OF THE INVENTION

The invention relates generally to inhalable pharmaceutical compositions, including methods for the manufacture and use thereof. The invention relates more particularly, in various embodiments, to inhalable pharmaceutical compositions having an aqueous dispersion of particles including a hydrophobic bioactive agent (e.g., CoQ10) and being suitable for continuous aerosolization. Due to their chemical composition and methods of manufacture, the pharmaceutical compositions exhibit distinctive physicochemical properties that provide advantageous aerosol transmission and output.

BACKGROUND OF THE INVENTION

Cancer is presently one of the leading causes of death in developed nations. Lung cancer is one example of a cancer with a high mortality rate and low long-term survival rate. Although research has vastly increased the understanding of many of the molecular mechanisms of tumorigenesis and has provided numerous new avenues for the treatment of cancer, including lung cancer, standard treatments for most malignancies remain gross resection, chemotherapy, and radiotherapy. While increasingly successful, each of these treatments can cause numerous undesirable side effects. For example, surgery can result in pain, traumatic injury to healthy tissue, and scarring. Radiotherapy and chemotherapy may cause nausea, immune suppression, gastric ulceration and secondary tumorigenesis. Furthermore, such extreme side effects can come without a correspondingly high survival rate.

Delivery of a therapeutic agent to the respiratory tract is one avenue for the treatment of numerous local and/or systemic diseases, including lung cancer. However, conventional techniques for delivery of agents to the lung can be ineffective, inefficient, and/or insufficient. For example, many known methods produce aerosols that have droplets that are two large to deliver a pharmaceutical to the lung, and/or that are too inconsistent to reliably deliver a specific dose. Particle formation technologies developed to address issues such as particle size, for example mechanical micronization processes and solution-based phase separation processes, can have additional limitations. Mechanical micronization methods such as milling can cause thermal and/or mechanical degredation of the pharmaceutical. Spray drying, another method used to micronize drug substances, can lead to difficulty in collecting small particles.

SUMMARY OF THE INVENTION

The invention provides inhalable pharmaceutical compositions having an aqueous dispersion of particles including a hydrophobic bioactive agent. Due to their chemical composition and methods of manufacture, the pharmaceutical compositions exhibit distinctive physicochemical properties that provide advantageous aerosol transmission and output, including continuous aerosolization. Accordingly, the invention provide improved methods for the treatment of diseases, including cancer, and compositions capable of delivering bioactive agents to aid in the treatment of diseases and other conditions, including by inhalation to the lungs.

Since a large amount of the available surface area of the lung is located in the deep lung, drug delivery can be facilitated by aerosol delivery of particles to the peripheral alveoli of the deep lung. In contrast, particles deposited in the upper respiratory tract can be rapidly removed by the mucociliary escalator, subsequently transported to the throat, and swallowed or removed by coughing. The invention, in various aspects and embodiments provides for the delivery of hydrophobic bioactive agents (e.g., including drugs that are strictly hydrophobic, lipophilic, and/or poorly water soluble), which are generally difficult to adequately aerosolize, to the deep lung (as well as other regions of the respiratory tract). In particular, the invention can provides for the continuous nebulization of nanodispersions of hydrophobic drugs for therapeutic use.

Other advantages of the various aspects and embodiments of the invention include, but are not limited to, high aerosol output (e.g., as measured by total aerosol output, TAO); high aerosol transmission (e.g., as measured by average percent transmission, APT); high total emitted dose (TED), continuous and stable aerosols (e.g., over a predetermined dosing event, not intermittent); consistent delivery (e.g., reproducible across different events); the capacity to deliver high doses (e.g., high mass fraction deposited and/or continuous delivery); the ability to meter doses (e.g., from small to large); the ability to deliver drug topically, locally, and/or systemically; high respirable fraction; and combinations thereof. Significantly, the invention can achieve such advantages with aqueous nanodispersions of hydrophobic drugs (e.g., as compared to prior art methods directed to simple, homogenous, drug solutions).

In one aspect, the invention features an inhalable pharmaceutical composition comprising a dispersion of liposomal particles suitable for continuous aerosolization. The composition includes a dispersion of liposomal particles having an average diameter between about 30 and 500 nm, each liposomal particle comprising a hydrophobic bioactive agent, a phospholipid, and an aqueous dispersion vehicle. The ratio of hydrophobic bioactive agent:phospholipid is between about 5:1 and about 1:5, the hydrophobic bioactive agent is between about 0.1 and 30% w/w of the composition, the phospholipid is between about 0.1 and 30% w/w of the composition, and the liposomal particles are dispersed within the aqueous dispersion vehicle. And, upon administration to a subject, the composition is characterized by continuous aerosolization sufficient to provide a therapeutic dose of the hydrophobic bioactive agent to the subject.

In another aspect, the invention features, an inhalable pharmaceutical composition comprising a dispersion of liposomal particles suitable for continuous aerosolization. The composition includes a dispersion of liposomal particles having an average diameter between about 30 and 500 nm, each liposomal particle comprising a hydrophobic bioactive agent, a phospholipid, and an aqueous dispersion vehicle. The ratio of hydrophobic bioactive agent:phospholipid is between about 5:1 and about 1:5, the hydrophobic bioactive agent is between about 0.1 and 30% w/w of the composition, the phospholipid is between about 0.1 and 30% w/w of the composition, and the liposomal particles are dispersed within the aqueous dispersion vehicle. And, upon continuous aerosolization, the composition is capable of achieving a bioactive agent concentration of at least about 500 µg/g wet lung tissue.

In another aspect, the invention features, an inhalable pharmaceutical composition comprising a dispersion of liposomal particles suitable for continuous aerosolization. The composition includes a dispersion of liposomal particles having an average diameter between about 30 and 500 nm, each liposomal particle comprising a hydrophobic bioactive agent, a phospholipid, and an aqueous dispersion vehicle. The ratio of hydrophobic bioactive agent:phospholipid is between about 5:1 and about 1:5, the hydrophobic bioactive agent is between about 0.1 and 30% w/w of the composition, the phospholipid is between about 0.1 and 30% w/w of the composition, and the liposomal particles are dispersed within the aqueous dispersion vehicle. And, upon continuous aerosolization, the composition is capable of achieving a total emitted dose (TED) of at least about 2,900 µg over 15 seconds.

In still another aspect, the invention features an inhalable pharmaceutical composition comprising a dispersion of liposomal particles suitable for continuous aerosolization. The composition includes a dispersion of liposomal particles having an average diameter between about 30 and 300 nm, each liposomal particle comprising CoQ10, dipalmitoyl phosphatidylcholine (DPPC), and an aqueous dispersion vehicle. The ratio of CoQ10:DPPC is between about 5:1 and about 1:5, the CoQ10 is between about 0.1 and 6% w/w of the composition, and the liposomal particles are dispersed within the aqueous dispersion vehicle. And, upon administration to a subject, the composition is characterized by continuous aerosolization sufficient to provide a therapeutic dose of the hydrophobic bioactive agent to the subject (or, alternatively, the composition can be characterized by another pharmacokinetic property such as being capable of achieving a bioactive agent concentration of at least about 500 µg/g wet lung tissue or a total emitted dose (TED) of at least about 2,900 µg over 15 seconds).

In yet another aspect, the invention features an inhalable pharmaceutical composition comprising a dispersion of liposomal particles suitable for continuous aerosolization. The composition includes a dispersion of liposomal particles having an average diameter between about 30 and 300 nm, each liposomal particle comprising CoQ10, distearoyl phosphatidylcholine (DSPC), and an aqueous dispersion vehicle. The ratio of CoQ10:DSPC is between about 5:1 and about 1:5, the CoQ10 is between about 0.1 and 6% w/w of the composition, and the liposomal particles are dispersed within the aqueous dispersion vehicle. And, upon administration to a subject, the composition is characterized by continuous aerosolization sufficient to provide a therapeutic dose of the hydrophobic bioactive agent to the subject (or, alternatively, the composition can be characterized by another pharmacokinetic property such as being capable of achieving a bioactive agent concentration of at least about 500 µg/g wet lung tissue or a total emitted dose (TED) of at least about 2,900 µg over 15 seconds).

In still yet another aspect, the invention features an inhalable pharmaceutical composition comprising a dispersion of liposomal particles suitable for continuous aerosolization. The composition includes a dispersion of liposomal particles having an average diameter between about 30 and 300 nm, each liposomal particle comprising CoQ10, dimyristoyl phosphatidylcholine (DMPC), and an aqueous dispersion vehicle. The ratio of CoQ10:DMPC is between about 5:1 and about 1:5, the CoQ10 is between about 0.1 and 6% w/w of the composition, and the liposomal particles are dispersed within the aqueous dispersion vehicle. And, upon administration to a subject, the composition is characterized by continuous aerosolization sufficient to provide a therapeutic dose of the hydrophobic bioactive agent to the subject (or, alternatively, the composition can be characterized by another pharmacokinetic property such as being capable of achieving a bioactive agent concentration of at least about 500 µg/g wet lung tissue or a total emitted dose (TED) of at least about 2,900 µg over 15 seconds).

In still another aspect, the invention features a method for preparing an inhalable pharmaceutical composition. The method includes the steps of: (i) hydrating a phospholipid, thereby forming a hydrated phospholipid; (ii) mixing the hydrated phospholipid, a hydrophobic bioactive agent, and an aqueous dispersion vehicle, thereby producing a mixture; and (iii) homogenizing the mixture, thereby producing a dispersion of liposomal particles comprising the phospholipid and hydrophobic bioactive agent dispersed within the aqueous dispersion vehicle and having an average diameter between about 30 and 500. The ratio of hydrophobic bioactive agent:phospholipid is between about 5:1 and about 1:5, the hydrophobic bioactive agent is between about 0.1 and 30% w/w of the composition, and the phospholipid is between about 0.1 and 30% w/w of the composition. And, upon administration to a subject, the composition is characterized by continuous aerosolization sufficient to provide a therapeutic dose of the hydrophobic bioactive agent to the subject (or, alternatively, the composition can be characterized by another pharmacokinetic property such as being capable of achieving a bioactive agent concentration of at least about 500 µg/g wet lung tissue or a total emitted dose (TED) of at least about 2,900 µg over 15 seconds).

In yet another aspect, the invention features a method for administering an inhalable pharmaceutical composition. The method includes the steps of: (i) aerosolizing a dispersion of liposomal particles, thereby forming a respirable aerosol comprising a plurality of droplets having a mass median aerodynamic diameter (MMAD) between about 1 and 5 µm, and (ii) delivering a therapeutically effective amount of the hydrophobic bioactive agent to a lung of a subject in need of treatment. The dispersion of liposomal particles has an average diameter between about 30 and 500 nm, each liposomal particle comprising a hydrophobic bioactive agent and a phospholipid dispersed within an aqueous dispersion vehicle. The ratio of hydrophobic bioactive agent:phospholipid is between about 5:1 and about 1:5, the hydrophobic bioactive agent is between about 0.1 and 30% w/w of the composition, and the phospholipid is between about 0.1 and 30% w/w of the composition. And, upon administration to a subject, the composition is characterized by continuous aerosolization sufficient to provide a therapeutic dose of the hydrophobic bioactive agent to the subject (or, alternatively, the composition can be characterized by another pharmacokinetic property such as being capable of achieving a bioactive agent concentration of at least about 500 µg/g wet lung tissue or a total emitted dose (TED) of at least about 2,900 µg over 15 seconds).

In still yet another aspect, the invention features an inhalable pharmaceutical composition prepared by a process including the steps of: (i) hydrating a phospholipid, thereby forming a hydrated phospholipid; (ii) mixing the hydrated phospholipid, a hydrophobic bioactive agent, and an aqueous dispersion vehicle, thereby producing a mixture; and homogenizing the mixture, thereby producing a dispersion of liposomal particles comprising the phospholipid and hydrophobic bioactive agent dispersed within the aqueous dispersion vehicle and having an average diameter between about 30 and 500, where the ratio of hydrophobic bioactive agent:phospholipid is between about 5:1 and about 1:5, the hydrophobic bioactive agent is between about 0.1 and 30% w/w of the composition, and the phospholipid is between about 0.1 and 30% w/w of the composition. And, upon administration to a subject, the composition is characterized by continuous aerosolization sufficient to provide a therapeutic dose of the hydrophobic bioactive agent to the subject (or, alternatively, the composition can be characterized by another pharmacokinetic property such as being capable of achieving a bioactive agent concentration of at least about 500 µg/g wet lung tissue or a total emitted dose (TED) of at least about 2,900 µg over 15 seconds).

In still another aspect, the invention features a method for adapting a laser diffraction particle size system for continuously measuring a continuous aerosol. The method includes the steps of: (i) providing a laser diffraction particle size system comprising a nebulizer reservoir, membrane, laser beam, lens, and air suction source; (ii) positioning the nebulizer reservoir with the membrane above the upper edge of the laser beam and at a distance between the lens and the center of an aerosol cloud chamber; and (iii) positioning the air suction source beneath the laser beam. The adapted system avoids fogging of the lens by continuously exhausting the aerosol cloud chamber while continuously measuring transmission of the aerosol during continuous aerosolization.

In yet another aspect, the invention features a laser diffraction particle size system for continuously measuring a continuous aerosol. The system includes (i) a nebulizer reservoir positioned with a membrane above an upper edge of a laser beam and at a distance between a lens and the center of an aerosol cloud chamber; and (ii) an air suction source positioned beneath the laser beam. The system avoids fogging of the lens by continuously exhausting the aerosol cloud while continuously measuring transmission of the aerosol during continuous aerosolization.

In still yet another aspect, the invention features a method for continuously measuring a continuous aerosol. The method includes the steps of: (i) providing a continuous aerosol to a laser diffraction particle size system, the system comprising a nebulizer reservoir positioned with a membrane above an upper edge of a laser beam and at a distance between a lens and the center of an aerosol cloud chamber, and an air suction source positioned beneath the laser beam; and (ii) continuously measuring transmission of the aerosol while the system avoids fogging of the lens by continuously exhausting the aerosol cloud chamber.

In still yet another aspect, the invention features a method for manufacturing and verifying the average percent transmission (APT) of an inhalable pharmaceutical composition. The method includes the steps of: (i) hydrating a phospholipid, thereby forming a hydrated phospholipid; (ii) mixing the hydrated phospholipid, a hydrophobic bioactive agent, and an aqueous dispersion vehicle, thereby producing a mixture; (iii) homogenizing the mixture, thereby producing a dispersion of liposomal particles comprising the phospholipid and hydrophobic bioactive agent dispersed within the aqueous dispersion vehicle and having an average diameter between about 30 and 500, wherein the ratio of hydrophobic bioactive agent:phospholipid is between about 5:1 and about 1:5, the hydrophobic bioactive agent is between about 0.1 and 30% w/w of the composition, and the phospholipid is between about 0.1 and 30% w/w of the composition; (iv) aerosolizing the dispersion of liposomal particles, thereby forming a respirable aerosol comprising a plurality of droplets, each droplet comprising a dispersion of liposomal particles and having a mass median aerodynamic diameter (MMAD) between about 1 and 5 µm; (v) providing the respirable aerosol to a laser diffraction particle size system, the system comprising a nebulizer reservoir positioned with a membrane above an upper edge of a laser beam and at a distance between a lens and the center of an aerosol cloud chamber, and an air suction source positioned beneath the laser beam; and (vi) continuously measuring transmission of aerosol with the laser diffraction particle size system, thereby determining if the composition is characterized by a predetermined APT value.

In different embodiments, any of the above aspects can be combined with any one or more or the features below, as well as any one or more of the features in the detailed description and examples.

In various embodiments, the aqueous dispersion vehicle comprises water or an aqueous salt solution. The aqueous dispersion vehicle can be a buffer such as phosphate buffered saline.

In some embodiments, the dispersion of liposomal particles is in the form of a continuous respirable aerosol comprising a plurality of aqueous droplets containing a dispersion of liposomal particles and having a mass median aerodynamic diameter (MMAD) between about 1 and 5 µm.

In certain embodiments, the composition is characterized by an APT between about 50 and 100% over at least 15 minutes of continuous aerosolization. The composition can be characterized by an APT between about 50 and 100%, between about 60 and 100%, between about 70 and 100%, between about 80 and 100%, between about 90 and 100%, between about 50 and 95%, between about 60 and 95%, between about 70 and 95%, between about 80 and 95%, between about 90 and 95%, between about 50 and 90%, between about 60 and 90%, between about 70 and 90%, between about 80 and 90%, less than about 50%, less than about 55%, less than about 65%, less than about 70%, less than about 75%, less than about 80%, less than about 85%, less than about 90%, less than about 95%, less than about 100%, or any sub-range or value therebetween. The continuous aerosolization can have a duration of about 1, 2, 3, 4, 5, 6, 7, 8, 9, 10, 11, 12, 13, 14, 15, 20, 25, 30, 35, 40, 50, or 60 minutes. The plurality of droplets can have a MMAD between about 1 and 5 µm over at least 15 minutes of continuous aerosolization.

In various embodiments, the composition is characterized by an APT between about 50 and 100% and after at least seven days of storage. The liposomal particles have an average diameter between about 30 and 500 nm after at least seven days of storage. Storage can be at ambient conditions or other controlled conditions (e.g., in a refrigerator).

In some embodiments, the composition can be characterized by one or more physicochemical property. The composition can have a flow index of about 0.4, 0.5, 0.6, 0.7, 0.8, 0.9, 1.0, 1.1, 1.2, or 1.3. The composition can have a viscosity of about 0.1, 0.15, 0.2, 1, 100, or 110 cP. The composition can have a zeta potential of about 2.5, 1.5, −2.5, −10, −50, −55, or −60 mV. The composition can have a surface tension of about 25, 30, 35, 40, 45, or 50 mN/m. The composition can have a yield stress of about 11, 12, 13, 14, 15, 16, 17, or 18 mPa. The dispersion of liposomal particles can have an average diameter between about 30 and 100 nm, 50 and 150 nm, 30 and 300 nm, 100 and 400 nm, or 200 and 300 nm. The composition can have a polydispersivity index (PDI) of about 0.1, 0.2, 0.3, 0.4, 0.5, 0.6, or 0.7. The composition can have a TAO of at least about 40, 45, 50, 55, 60, 65, 70, 75, 80, 85, 90, 95, or 100%. The composition can have a TED of at least about 3,600, 3,900, 4,300, or 4,600

µg over 15 seconds (e.g., as measured by DUSA, see Example 2). The composition can be characterized by non-Newtonian fluid behavior.

In various embodiments, the plurality of droplets can have a mass median aerodynamic diameter (MMAD) of about 1, 2, 3, 4, or 5 µm. The plurality of droplets can have a geometric standard deviation (GSD) of less than about 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, or 0.5.

In some embodiment, the hydrophobic bioactive agent includes one or more analgesics, anti-inflammatory agents, anthelmintics, anti-arrhythmic agents, antibacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-Blockers, cardiac inotropic agents, corticosteroids, diuretics, anti-parkinsonian agents, gastro-intestinal agents, histamine receptor antagonists, keratolytics, lipid regulating agents, anti-anginal agents, cox-2 inhibitors, leucotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and combinations thereof. The hydrophobic bioactive agent can include one or more hydrophobic anti-inflammatory steroid, NSAID agent, antibacterial agent, antifungal agent, chemotherapeutic agent, vasoldilator, or a combination thereof.

In certain embodiments, the hydrophobic bioactive agent includes one or more of acutretin, albendazole, albuterol, aminogluthemide, amiodarone, amlodipine, amphetamine, amphotericin B, atorvastatin, atovaquone, azithromycin, baclofen, beclomethsone, benezepril, benzonatate, betamethasone, bicalutanide, budesonide, bupropion, busulphan, butenafine, calcifediol, calciprotiene, calcitriol, camptothecan, candesartan, capsaicin, carbamezepine, carotenes, celecoxib, cerivistatin, cetrizine, chlorpheniramine, cholecalciferol, cilostazol, cimetidine, cinnarizine, ciprofloxacin, cisapride, clarithromycin, clemastine, clomiphene, clomipramine, clopidrogel, codeine, coenzyme Q10, cyclobenzaprine, cyclosporine, danazol, dantrolene, dexchlorpheniramine, diclofenac, dicoumarol, digoxin, dihydroepiandrosterone, dihydroergotamine, dihydrotachysterol, dirithromycin, donepezil, efavirenz, eposartan, ergocalciferol, ergotamine, essential fatty acid sources, etodolac, etoposide, famotidine, fenofibrate, fentanyl, fexofenadine, finasteride, flucanazole, flurbiprofen, fluvastatin, fosphenylion, frovatriptan, furazolidone, gabapentin, gemfibrozil, glibenclamide, glipizide, glyburide, glymepride, griseofulvin, halofantrine, ibuprofen, irbesartan, irinotecan, isosorbide dinitrate, isotreinoin, itraconazole, ivermectin, ketoconazole, ketorolac, lamotrigine, lanosprazole, leflunomide, lisinopril, loperamide, loratadine, lovastatin, L-thryroxine, lutein, lycopene, medroxyprogesterone, mefepristone, mefloquine, megesterol acetate, methadone, methoxsalen, metronidazole, miconazole, midazolam, miglitol, minoxidil, mitoxantrone, montelukast, nabumetone, nalbuphine, naratiptan, nelfinavir, nifedipine, nilsolidipine, nilutanide, nitrofurantoin, nizatidine, omeprazole, oprevelkin, osterodiol, oxaprozin, paclitaxel, paricalcitol, paroxetine, pentazocine, pioglitazone, pizofetin, pravastatin, prednisolone, probucol, progesterone, pseudoephedrine, pyridostigmine, rabeprazole, raloxifene, refocoxib, repaglinide, rifabutine, rifapentine, rimexolone, ritanovir, rizatriptan, rosigiltazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terzosin, tetrahydrocannabinol, tiagabine, ticlidopine, tirofibran, tizanidine, topiramate, topotecan, toremifene, tramadol, tretinoin, troglitazone, trovafloxacin, valsartan, venlafaxine, vertoporfin, vigabatrin, vitamin A, vitamin D, vitamin E, vitamin K, zafirlukast, zileuton, zolmitriptan, zolpidem, zopiclone, and combinations thereof.

In various embodiments, the hydrophobic bioactive agent also includes an additive selected from the group consisting of deoxyglucoses, deoxyglucose salts, dihydroxy acetone, succinates, pyruvates, citrates, fumarates, malates, malonates, lactates, glutarates, and combinations thereof. The additive can be 2-deoxyglucose, 2-deoxyglucose phosphate, 6-deoxyglucose, 6-deoxyglucose phosphate, dihydroxy acetone, and combinations thereof.

In some embodiments, the hydrophobic bioactive agent includes CoQ10. The CoQ10 can substituted by an additive at the 1 position, the 4 position, or combinations thereof.

In certain embodiments, the hydrophobic bioactive agent is about 4% w/w or less of the composition. The hydrophobic bioactive agent can be about 6, 5, 4, 3, 2, or 1% w/w or less of the composition.

In various embodiments, the phospholipid includes one or more of lecithin, lysolecithin, phosphatidylcholine, phosphatidylethanolamine, phosphatidylinositol, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, and combinations thereof. The phospholipid can include DPPC, DSPC, DMPC, or a combination thereof. The phospholipid can be a substantially pure phospholipid. The phospholipid can be about 3% w/w or less of the composition.

In some embodiments, the ratio of hydrophobic bioactive agent:phospholipid is about 1:1, 4:3, or 4:2.5. The ratio of hydrophobic bioactive agent:phospholipid can be about 5:1, 4:1, 3:1, 2:1, 1:1, 1:2, 1:3, 1:4, 1:5, or any value therebetween.

In certain embodiments, the phospholipid is in combination with one or more absorbents, antifoaming agents, acidifiers, alkalizers, buffers, antimicrobial agents, antioxidants, binders, solubilizing agents, solvents, viscosity modifiers, humectants, thickening agents, and combinations thereof. Alternatively, the composition can consist essentially of the hydrophobic bioactive agent, phospholipid, and aqueous dispersion vehicle.

In various embodiments, the composition includes sodium chloride in an amount less than about 1.0% w/v of the composition. The composition can include a salt in an amount making the composition essentially isosmotic with the human lung.

In some embodiments, the dispersion is suspension, nanosuspension, emulsion, or microemulsion.

In certain embodiments, the method also includes aerosolizing the dispersion of liposomal particles, thereby forming a respirable aerosol comprising a plurality of droplets, each droplet comprising a dispersion of liposomal particles and having a mass median aerodynamic diameter (MMAD) between about 1 and 5 µm.

In various embodiments, mixing includes high shear mixing for up to about 5 minutes at about 10,000 to 20,000 rpm and at about 50 to 65° C. Mixing can last for up to about 1, 2, 3, 4, or 5 minutes. Mixing can be at about 10,000, 11,000, 12,000, 13,000, 14,000, 15,000, 16,000, 17,000, 18,000, 19,000, or 20,000 rpm. Mixing can take place at about 50, 55, 60, or 65° C. Temperature can vary depending upon the melting point of the hydrophobic bioactive agent used.

In some embodiments, homogenizing includes microfluidization. Homoginization can include ultrasonic homogenization. Homogenizing can include high pressure homogenization for about 1-50 passes at about 30,000 psi and at about 50 to 65° C. Homoginization can be for about 1, 2, 3, 4, 5, 10, 15, 20, 25, 30, 35, 40, 45, or 50 passes. The pressure can be about 25,000, 26,000, 27,000, 28,000, 29,000, 30,000, 31,000, 32,000, 33,000, 34,000, or 35,000 psi. The temperature can be about 50, 55, 60, or 65° C. Temperature can vary depending upon the melting point of the hydrophobic bioactive agent used.

In certain embodiments, aerosolization includes vibrating mesh nebulization. Any suitable method for continuous nebulization can be adapted for use with the present invention.

In various embodiments, delivery achieves a mass fraction deposited of at least about 1, 2, 3, 4, 5, 6, 7, 8, 9, 10, 15, or 20%.

In some embodiments, delivery achieves local delivery to the lung substantially without systemic delivery.

In certain embodiments, delivery achieves an elevated amount of the hydrophobic bioactive agent in the lung for at least 48 hours after administration.

In various embodiments, upon continuous aerosolization, the composition is capable of achieving a bioactive agent concentration of at least about 900, 800, 700, 600, 500, 400, 300, 200, or 100 µg/g wet lung tissue. It will be understood that the archived wet lung tissue concentration will be effected by the subject, method of administration, and formulation, among other things. Therefore, in various embodiments, the bioactive agent concentration can be a therapeutically adequate or therapeutically desirable amount of the particular bioactive agent being used.

In some embodiments, delivering a therapeutically effective amount of the hydrophobic bioactive agent comprises metering a dose of the bioactive agent.

In certain embodiments, the subject has cancer. The cancer can be lung cancer. More generally, the subject can have any one or more afflictions affecting the respiratory tract including, but not limited to, one or more of asthma, allergies, chronic obstructive pulmonary disease, chronic bronchitis, acute bronchitis, emphysema, cystic fibrosis, pneumonia, tuberculosis, pulmonary edema, acute respiratory distress syndrome, pneumoconiosis, interstitial lung disease, pulmonary edema, pulmonary embolism, pulmonary hypertension, pleural effusion, pneumothorax, mesothelioma, amyotrophic lateral sclerosis, myasthenia gravis, and lung disease.

In various embodiments, the composition does not include an opsonization reducer (e.g., an opsonization reducer that interferes with aerosolization). For example, the composition can specifically exclude a polyoxyethylene polyoxypropylene block polymer such as a Poloxamer (e.g., poloxymer 188), Pluronic, Lutrol, and Superonic. In another example, the composition can specifically exclude polyethylene glycol (PEG) of various chain lengths, polysaccharides, other PEG-containing copolymers, poloxamines, and the like. Alternatively, formulations in accordance with the invention can include one or more opsonization enhancers in an amount that does not substantially interfere with aerosolizlation, for example, if the amount opsonization enhancer imparts an otherwise desirable property on the formulation. In one embodiment, the composition includes a polyoxypropylene-poloxyethylene block polymer at 0.001-5% by weight of the total composition.

The present invention is described in further detail by the figures and examples below, which are used only for illustration purposes and are not limiting.

DESCRIPTION OF THE DRAWINGS

FIG. 9A shows a Malvern Spraytec® coupled with inhalation cell. FIG. 9B shows a schematic diagram of Malvern Spraytec® with inhalation cell in horizontal position.

FIG. 29A shows the TED NGI and TED DUSA values for the studied formulations.

FIG. 43 shows Table 2.
FIG. 44 shows Table 3.
FIG. 45 shows Table 4.
FIG. 46 shows Table 5.
FIG. 47 shows Table 6.
FIG. 48 shows Table 7.
FIG. 49 shows Table 8.
FIG. 50 shows Table 9.

DETAILED DESCRIPTION OF THE INVENTION

Figure 1A:
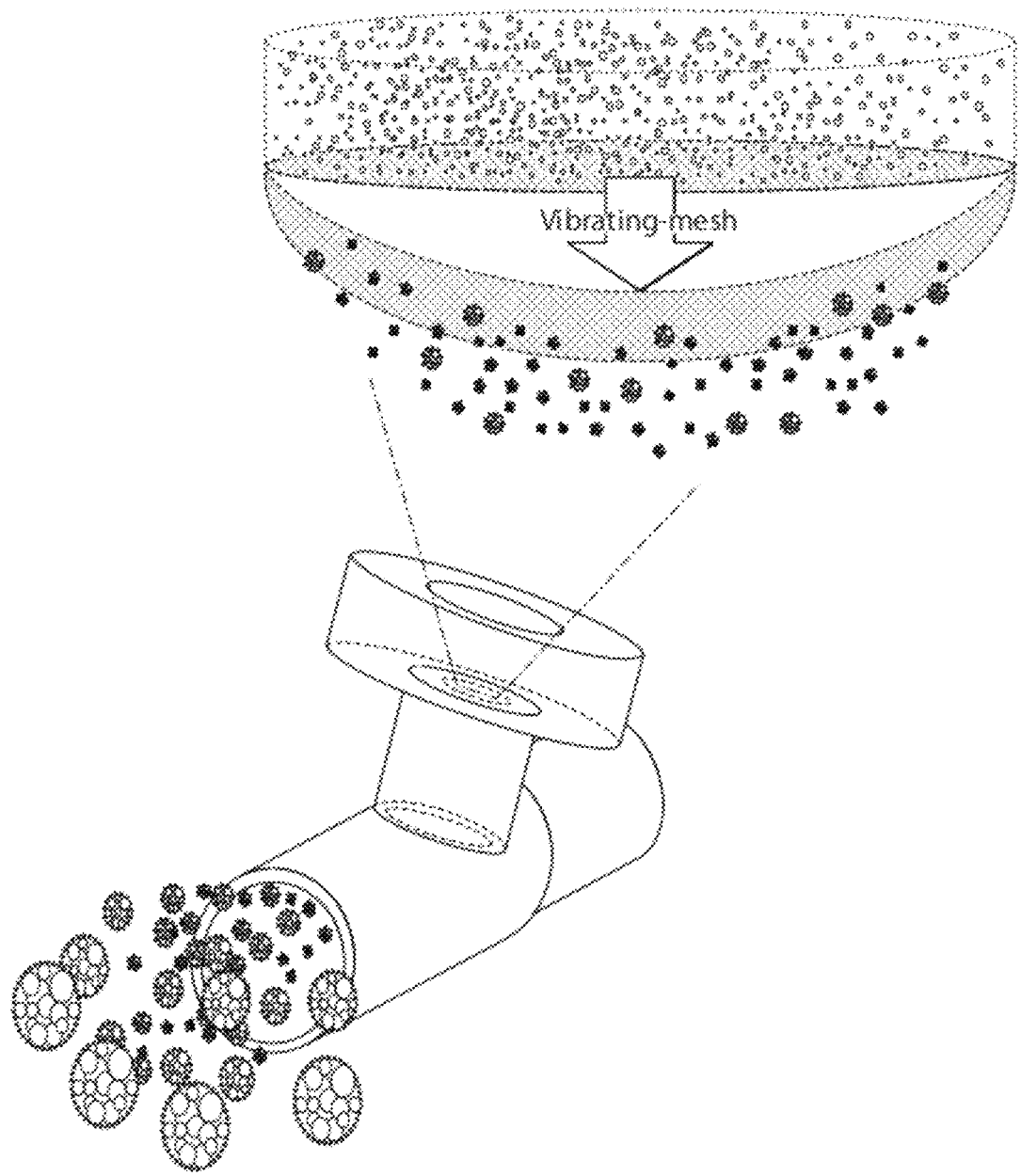
FIG. 1A shows a schematic diagram of aerosolization of drug dispersions using a vibrating mesh nebulizer.

As discussed above, the invention provides inhalable pharmaceutical compositions having an aqueous dispersion of particles including a hydrophobic bioactive agent. Due to their chemical composition and methods of manufacture, the pharmaceutical compositions exhibit distinctive physicochemical properties that provide advantageous aerosol transmission and output, including stable and continuous aerosolization.

CoQ10 was used as an exemplary hydrophobic bioactive agent. Coenzyme Q10, also known as CoQ10, ubiquinone or ubidecarenone, occurs naturally in the body. CoQ10 participates in electron transport and proton transfer in mitochondrial respiration. Therefore, altering the levels of this antioxidant may have an impact on biological activities such as aging, neurodegenerative and cardiovascular diseases, and cancer.

CoQ10 is a poorly-water soluble compound presented as a yellow or orange crystalline powder. The highest plasma concentration of CoQ10 reported in the literature is 10.7 µmol/L (approximately 9 µg/mL), which was obtained by administration of a solubilized oral formulations (e.g., commercially available dietary supplement or "nutraceutical"). Nevertheless, the maximum tolerated dose (MTD) has yet to be determined. The present invention provides formulations of CoQ10 for pulmonary delivery with advantageous pharmacokinetic profiles that will improve the pharmacodynamic responses for treating respiratory system malignancies. By delivering a high amount of drug to the disease site, a lower dose can be used (as compared to intravenous or oral administration).

The following description provides further detail regarding the inventive compositions (including the hydrophobic bioactive agents, phospholipids, aqueous dispersion vehicles, and other components), methods of manufacture (including mixing, homogenization, and aerosolization), and methods of treatment (including pharmacokinetics, pharmacodynamics, and indications). Finally, the detailed description provides illustrative examples of the invention, including Example 1: Development and Characterization of Phospholipid-Stabilized Submicron Aqueous Dispersions of CoQ10 Adapted for Continuous Nebulization; Example 2: Prediction of In Vitro Aerosolization Profiles Based on Rheological Behaviors of Aqueous Dispersions of CoQ10; Example 3: Pulmonary Deposition and Systemic Distribution in Mice of Inhalable Formulations of CoQ10; Example 4: Low Concentration Range Determination of Hydrophobic Drugs Using HPLC; Example 5: Determination of Suitable Hydrophobic Drug Concentrations in Phospholipid Nanodispersions Suitable for Continuous Nebulization; and Example 6: Measuring Inflamatory Reponse to Pulmonary Administration of Dispersions of Phospholipid Encapsulated Hydrophobic Bioactive Agents.

Compositions

In various embodiments, inhalable pharmaceutical compositions according to the invention include aqueous dispersion of particles suitable for continuous aerosolization. The particles each include a hydrophobic bioactive agent and a phospholipid, and are dispersed within an aqueous dispersion vehicle. In some embodiments, the particles are liposomal particles, or include a fraction of liposomal particles. In some embodiments, the composition can consist essentially of the hydrophobic bioactive agent, phospholipid, and aqueous dispersion vehicle. However, other embodiments including one or more additional components are possible. Various components for inclusion in the inventive compositions are discussed, in turn, below.

Hydrophobic Bioactive Agents

In various embodiments, one or more hydrophobic bioactive agents (also known as lipophilic bioactive agents) can be prepared in inhalable pharmaceutical compositions. Hydrophobic bioactive agents are relatively insoluble in water. For example, a hydrophobic bioactive agent can have a solubility in water of less than about 1 part of bioactive agent in about 1000 parts of water.

Suitable lipophilic bioactive agents can include, but are not limited to, analgesics, anti-inflammatory agents, anthelmintics, anti-arrhythmic agents, antibacterial agents, antiviral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-Blockers, cardiac inotropic agents, corticosteroids, diuretics, anti-parkinsonian agents, gastro-intestinal agents, histamine receptor antagonists, keratolytics, lipid regulating agents, anti-anginal agents, cox-2 inhibitors, leucotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, combinations thereof, and the like.

Non-limiting examples of suitable hydrophobic active agents include, but are not limited to, acutretin, albendazole, albuterol, aminogluthemide, amiodarone, amlodipine, amphetamine, amphotericin B, atorvastatin, atovaquone, azithromycin, baclofen, beclomethsone, benezepril, benzonatate, betamethasone, bicalutanide, budesonide, bupropion, busulphan, butenafine, calcifediol, calciprotiene, calcitriol, camptothecan, candesartan, capsaicin, carbamezepine, carotenes, celecoxib, cerivistatin, cetrizine, chlorpheniramine, cholecalciferol, cilostazol, cimetidine, cinnarizine, ciprofloxacin, cisapride, clarithromycin, clemastine, clomiphene, clomipramine, clopidrogel, codeine, coenzyme Q10, cyclobenzaprine, cyclosporine, danazol, dantrolene, dexchlorpheniramine, diclofenac, dicoumarol, digoxin, dihydro epiandrosterone, dihydroergotamine, dihydrotachysterol, dirithromycin, donepezil, efavirenz, eposartan, ergocalciferol, ergotamine, essential fatty acid sources, etodolac, etoposide, famotidine, fenofibrate, fentanyl, fexofenadine, finasteride, flucanazole, flurbiprofen, fluvastatin, fosphenylion, frovatriptan, furazolidone, gabapentin, gemfibrozil, glibenclamide, glipizide, glyburide, glymcpride, griseofulvin, halofantrine, ibuprofen, irbesartan, irinotecan, isosorbide dinitrate, isotreinoin, itraconazole, ivermectin, ketoconazole, ketorolac, lamotrigine, lanosprazole, leflunomide, lisinopril, loperamide, loratadine, lovastatin, L-thryroxine, lutein, lycopene, medroxyprogesterone, mefepristone, mefloquine, megesterol acetate, methadone, methoxsalen, metronidazole, miconazole, midazolam, miglitol, minoxidil, mitoxantrone, montelukast, nabumetone, nalbuphine, naratiptan, nelfinavir, nifedipine, nilsolidipine, nilutanide, nitrofurantoin, nizatidine, omeprazole, oprevelkin, osteradiol, oxaprozin, paclitaxel, paricalcitol, paroxetine, pentazocine, pioglitazone, pizofetin, pravastatin, prednisolone, probucol, progesterone, pseudoephedrine, pyridostigmine, rabeprazole, raloxifene, refocoxib, repaglinide, rifabutine, rifapentine, rimexolone, ritanovir, rizatriptan, rosigiltazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terzosin, tetrahydrocannabinol, tiagabine, ticlidopine, tirofibran, tizanidine, topiramate, topotecan, toremifene, tramadol, tretinoin, troglitazone, trovatloxacin, valsartan, venlafaxine, vertoporfin, vigabatrin, vitamin A, vitamin D, vitamin E, vitamin K, zafirlukast, zileuton, zolmitriptan, zolpidem, zopiclone, combinations thereof, and the like. Salts, isomers and/or other derivatives of the above-listed bioactive agents can also be used, as well as combinations thereof.

In various embodiments, CoQ10 can be the hydrophobic bioactive agent (e.g., alone, or in combination with one or more additional bioactive agents). CoQ10, sometimes referred to herein as CoQ10 or ubidccarenone, is a popular nutritional supplement and can be found in capsule form in nutritional stores, health food stores, pharmacies, and the like as a vitamin-like supplement that is hypothesized to help protect the immune system through the antioxidant properties of ubiquinol, the reduced form of CoQ10 (ubiquinone). As used herein, CoQ10 can also include derivatives thereof, including, for example, ubiquinol. Similarly CoQ10 can also include analogues of ubiquinone and ubiquinol, and precursor compounds as well and combinations thereof.

In various embodiments, the lipophilic bioactive agent, such as coenzyme Q10, can be combined with other bioactive agents or compounds for administration in vivo. Likewise, any bioactive agent can be combined with additional additives and/or excipients. The other bioactive agents, additives, and/or excipients can be hydrophobic or hydrophilic.

Combinations of bioactive agents can be utilized in accordance with the present disclosure for the treatment of cancers including, but not limited to, lung cancer. For example, a lipophilic bioactive agent, such as CoQ10, can be combined with deoxyglucoses, including 2-deoxyglucose and/or 2-deoxyglucose salts, 6-deoxyglucose and/or 6-deoxyglucose salts, as a mixture or blend and administered to a patient in vivo. Suitable salts can include phosphates, lactates, pyruvates, hydroxybutyrates, combinations thereof, and the like. In some embodiments the salt can be a phosphate such as 2-deoxyglucose phosphate, 6-deoxyglucose phosphate, combinations thereof, and the like. In other embodiments, the quinone or quinol ring of ubiquinone or ubiquinol can be substituted at the 1 position, the 4 position, or both, by the deoxyglucose or salts thereof, such as 2-deoxyglucose or 6-deoxyglucose or salts thereof, including 2-deoxyglucose phosphate or 6-deoxyglucose phosphate, with the substituted ubiquinone or ubiquinol then administered to a patient.

Similarly, dihydroxy acetone can be combined with CoQ10 as a mixture or blend and administered to a patient in vivo. In such embodiments, the quinone or quinol ring of ubiquinone or ubiquinol can be substituted at the 1 position, the 4 position, or both, with the dihydroxy acetone, with the substituted ubiquinone or ubiquinol then administered to a patient. In other embodiments, compounds which can be administered with the lipophilic bioactive agent, such as coenzyme Q10, include succinates, pyruvates, citrates, fumarates, malates, malonates, lactates, glutarates, combinations thereof, and the like, with specific examples including, but not limited to, sodium succinate, potassium succinate, combinations thereof, and the like.

Phospholipids

In various embodiments, the bioactive agent is comprised within a liposome and/or otherwise stabilized together with a phospholipid. Liposomes can be formed from one or more liposome-forming compounds such as phospholipids. Similarly, the bioactive agent and phospholipid can form other physical arrangement such as mixtures and dispersions. Compositions in accordance with the invention can include predominantly liposomal arrangement, a fraction of liposomes together with other arrangements, or can be essentially devoid of liposomes. Although various compounds and combinations thereof, are possible, the final composition must ultimately exhibit the distinctive physicochemical properties of the invention, which provide advantageous aerosol transmission and output, pharmacokinetics, and/or pharmacodynamics.

Suitable phospholipids and/or phospholipid derivatives/analogs for forming liposomes include, but are not limited to, lecithin, lysolecithin, phosphatidylcholine (e.g. dipalmitoyl phosphatidylcholine (DPPC) or dimyristoyl phosphatidylcholine (DMPC), phosphatidylethanolamine, phosphatidylinositol, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, combinations thereof, and the like.

In one embodiment, the phospholipid is a lecithin. Lecithin can be derived from egg or soybean. Such lecithins include those commercially available as PHOSPHOLIPON® 8SG, PHOSPHOLIPON® 90G, and PHOSPHOLIPON® 90H (the fully hydrogenated version of PHOSPHOLIPON® 90G) from American Lecithin Company, Oxford, Conn. (part of Lipo Chemicals, Inc.—the Lipo phospholipid catalog lists other potentially suitable phospholipids, for example those suitable for parenteral use). Other suitable lecithins include LECINOL 5-10® lecithin available, for example, from Nikko Chemicals, NOF (Japan), Lipo Chemicals, Inc., and Genzyme Corporation, as well as other commercial suppliers. Alternatively, in some embodiments it can be advantageious to select one or more phospholipids that are less hydrophilic than lecithin.

Phospholipids can be selected to confer a negative surface charge to the resulting liposome vesicles, which can reduce processing time and process energy, and which can aid in the formation of stable liposomes and aerosolization. For example, a high phosphatidylcholine content lecithin (e.g., dipalmitoyl phosphatidylcholine or dimyristoyl phosphatidylcholine) can be utilized to form a liposome. An example high phosphatidylcholine lecithin is PHOSPHOLIPON® 85G, which contains a minimum of 85% of alinoleic acid based-phosphatidylcholine. This lecithin is easy to use and is able to produce submicron liposomes at low process temperatures (from about 20° C. to about 55° C.) without the addition of any other special additives. PHOSPHOLIPON®

85G contains, in addition to phosphatidylcholine, approximately 5-7% phosphatidic acid.

Aqueous Dispersion Vehicles

An aqueous medium, for example water, is required in order to form an aqueous dispersion according to the present invention. Example aqueous dispersion vehicles include water, saline (e.g., iso-osmotic saline, a saline solution that will make the final formulation iso-osmotic with a subject's lung), and aqueous buffers (e.g., phosphate buffered saline). Other suitable aqueous dispersion vehicles can include other aqueous solutions that are compatible with the desired chemical composition, manufacturing method, and/or medical use.

Additional Components

Pharmaceutical compositions in accordance with the invention can include one or more additional components in addition to the one or more bioactive agent, one or more phospholipid, and one or more aqueous dispersion vehicle. Additional components can be used, for example, to enhance formulation of the liposomes possessing a lipophilic bioactive agent, to improve overall rheological and processing properties of the liposomes, and to insure microbiological integrity of the resulting liposomal concentrate during storage. Such components include, without limitation, absorbents, antifoaming agents, acidifiers, alkalizers, buffers, antimicrobial agents, antioxidants (for example ascorbates, tocopherols, butylated hydroxytoluene (BHT), polyphenols, phytic acid), binders, biological additives, chelating agents (for example, disodium ethylenediamine tetra acetic acid (EDTA), tetrasodium EDTA, sodium metasilicate, and the like), denaturants, external analgesics (for example aspirin, nonsteroidal anti-inflammatories and the like), steroidal anti-inflammatory drugs (such as hydrocortisone and the like), preservatives (for example imidazolidinyl urea, diazolidinyl urea, phenoxycthanol, methylparaben, ethylparaben, propylparaben, and the like), reducing agents, solubilizing agents, solvents, viscosity modifiers, humectants, thickening agents, surfactants, fillers, stabilizers, polymers, protease inhibitors, antioxidants, absorption enhancers, and combinations thereof. Such additional components can be present in an amount from about 0.001% by weight to about 10% by weight of the dispersion.

The excipients and adjuvants that can be used in the present disclosure, while potentially having some activity in their own right, for example, as antioxidants, generally include compounds that enhance the efficiency and/or efficacy of the active agents. It is also possible to have more than one excipient, adjuvant, or even active agents in a given respirable aggregate.

Excipients can be selected and added either before or after the drug or bioactive age particles are formed, in order to enable the drug or bioactive age particles to be homogeneously admixed for appropriate administration. Excipients can include those items described above as suitable for formation of liposomes. Other suitable excipients include polymers, absorption enhancers, solubility enhancing agents, dissolution rate enhancing agents, stability enhancing agents, bioadhesive agents, controlled release agents, flow aids and processing aids. In some embodiments, suitable excipients include cellulose ethers, acrylic acid polymers, bile salts, and combinations thereof. Other suitable excipients include those described in detail in the Handbook of Pharmaceutical Excipients, published jointly by the American Pharmaceutical Association and The Pharmaceutical Society of Great Britain, the Pharmaceutical Press, 1986, relevant portions of which are incorporated by reference herein. Such excipients are commercially available and/or can be prepared by techniques within the purview of those skilled in the art.

Excipients can also be chosen alone or in combination to modify the intended function of the effective ingredients by improving flow, or bioavailability, or to control or delay the release of the active agent. Specific non-limiting examples of excipients include: SPAN 80, TWEEN 80, BRIJ 35, BRIJ 98, PLURONICS, SUCROESTER 7, SUCROESTER II, SUCROESTER 15, sodium lauryl sulfate, oleic acid, laureth-9, laureth-8, lauric acid, vitamin E, TPGS, GELUCIRE 50/13, GELUCIRE 53/1 0, LABRAFIL, dipalmitoyl phosphadityl choline, glycolic acid and salts, deoxycholic acid and salts, sodium fusidate, cyclodextrins, polyethylene glycols, labrasol, polyvinyl alcohols, polyvinyl pyrrolidones, tyloxapol, cellulose derivatives, polyethoxylated castor oil derivatives, combinations thereof, and the like.

Examples of suitable humectants include, but are not limited to, polyols and polyol derivatives, including glycerol, diglycerol, triglycerol, ethylene glycol, propylene glycol, butylene glycol, pentylene glycol (sometimes referred to herein as 1,2-pentane diol), isopreneglycol (1,4-pentane diol), 1,5-pentane diol, hexylene glycol, erythritol, 1,2,6-hexanetriol, polyethylene glycols ("PEG") such as PEG-4, PEG-6, PEG-7, PEG-8, PEG-9, PEG-IO, PEG-12, PEG-14, PEG-I 6, PEG-18, PEG-20, and combinations thereof, sugars and sugar derivatives (including, inter alia, fructose, glucose, maltose, maltitol, mannitol, inositol, sorbitol, sorbityl silanediol, sucrose, trehalose, xylose, xylitol, glucuronic acid and salts thereof), ethoxylated sorbitol (Sorbeth-6, Sorbeth-20, Sorbeth-30, Sorbeth-40), combinations thereof, and the like. In other embodiments, glycols such as butylene glycol, 1,2-pentane diol, glycerin, 1,5-pentane diol, combinations thereof, and the like, can be utilized as a humectant. Where utilized, any of the above humectants, including combinations thereof, can be present in amounts from about 0.1% by weight to about 20% by weight of the second dispersion, in embodiments from about 1% by weight to about 5% by weight of the second dispersion.

In some embodiments, a preservative such as phenoxycthanol and a humectant such as propylene glycol can both be included in the formulation. The propylene glycol can provide humectant activity and assist in the preservation of the concentrate when combined with phenoxyethanol. The phenoxyethanol and propylene glycol mix can be water soluble and non-volatile. This embodiment is in contrast with the use of ethanol for preservation, which is often utilized by suppliers of liposomal dispersions. Where present, such preservatives can be present in amounts from about 0.01% by weight to about 3% by weight of the formulation.

Certain embodiments can include a dispersion stabilizing agent. Example dispersion stabilizing agents include Polyethoxylated (a/k/a pegylated) castor oil (Cremophor® EL), Polyethoxylated hydrogenated castor oil (Cremophor® RH 40), Tocopherol polyethylene glycol succinate (Pegylated vitamin E, Vitamin E TPGS), Polysorbates (Tweens®), Sorbitan fatty acid esters (Spans®), Bile acids and bile-acid salts and DMPC.

Certain embodiments can exclude opsonization reducers (e.g., opsonization reducers that can interfere with aerosolization). For example, the composition can specifically exclude a polyoxyethylene polyoxypropylene block polymer such as a Poloxamer (e.g., poloxymer 188), Pluronic, Lutrol, and Superonic. In another example, the composition can specifically exclude polyethylene glycol (PEG) of various chain lengths, polysaccharides, other PEG-containing copolymers, poloxamines, and the like. Alternatively, formulations in accordance with the invention can include one or more opsonization enhancers in an amount or kind (e.g., suitable HLB) that does not substantially interfere with aerosolizlation, for example, if the amount opsonization enhancer imparts an otherwise desirable property on the formulation. In one embodiment, the composition includes a polyoxypropylene-poloxyethylene block polymer at 0.001-5% by weight of the total composition. In another embodiment, the formulation includes a relatively small amount of one or more hydrophilic polymers, to improve stability and increase TAO while maintaining effective and continuous aerosolization.

Formulations can include pulmonary surfactants and/or mucolytic agents. Suitable pulmonary surfactants include, but are not limited to, pulmonary surfactant preparations having the function of natural pulmonary surfactant. These can include both natural and synthetic pulmonary surfactants. In various embodiments, compositions which contain phospholipids and/or pulmonary surfactant proteins can be utilized.

Exemplary phospholipids that can be used as pulmonary surfactants include dipalmitoylphosphatidylcholine (DPPC), palmitoyloleylphosphatidylglycerol (POPG) and/or phosphatidylglycerol (PG). Other suitable phospholipids include mixtures of various phospholipids, for example, mixtures of dipalmitoylphosphatidyicholine (DPPC) and palmitoyloleylphosphatidylglycerol (POPG) at a ratio of from about 7 to about 3 to from about 3 to about 7.

Commercial products that can be used as pulmonary surfactants include CUROSURF® (INN: PORACTANT ALFA) (Serono, Pharma GmbH, Unterschleipheim), a natural surfactant from homogenized porcine lungs; SURVANTA® (INN: BERACTANT) (Abbott GmbH, Wiesbaden), extract of bovine lungs; ALVEOFACT® (INN: BOVACTANT) (Boehringer Ingelheim), extract of bovine lungs; EXOSURF® (INN: COLFOSCERIL PALMITATE) (GlaxoSmithKline), a synthetic phospholipid containing excipients; SURFACTEN® (INN: SURFACTANT-TA) (Mitsubishi Pharma Corporation), a pulmonary surfactant extracted from bovine lungs; INFASURF® (INN: CALFACTANT) (Forest Pharmaceuticals), a surfactant extracted from calf lungs; ALEC® (INN: PUMACTANT) (Britannia Pharmaceuticals), an artificial surfactant of DPPC and PO; and BLES® (BLES Biochemical Inc.), a bovine lipid extract surfactant.

Suitable pulmonary surfactant proteins include both proteins obtained from natural sources, such as pulmonary lavage or extraction from amniotic fluid, and proteins prepared by genetic engineering or chemical synthesis. Pulmonary surfactant proteins designated by SP-B (Surfactant Protein-B) and SP-C (Surfactant Protein-C) and their modified derivatives, including recombinant forms of the proteins, can be utilized in some embodiments.

Suitable mucolytic agents include, but are not limited to, guaifenesin, iodinated glycerol, glyceryl guaiacolate, terpin hydrate, ammonium chloride, N-acetylcysteine, bromhexine, ambroxol, iodide, their pharmaceutically acceptable salts, and combinations thereof.

In some embodiments, the amount of preservatives utilized in a composition of the present disclosure including a lipophilic bioactive agent in liposomes can also be reduced by the inclusion of additional additives. For example, the amount of preservatives can be reduced in a composition of the present disclosure by the addition of multifunctional diols including, but not limited to, 1,2-pentane diol, 1,4-pentane diol, hexylene glycol, propylene glycol, 1,3-butylene glycol, glycerol or diglycerol, combinations thereof, and the like, and by lowering the water activity, Aw, via the addition of humectants described above and through the addition of the soluble ingredients. Other examples include soluble ingredients such as pH adjusting and buffering agents, tonicity adjusting agents, wetting agents and the like, for example, sodium acetate, sodium chloride, potassium chloride, calcium chloride, sorbitan monolaurate, triethanolamine oleate, and the like. Other buffers that can be added include sodium hydroxide, potassium hydroxide, ammonium hydroxide, monoethanolamine, diethanolamine, triethanolamine, diisopropanolamine, aminomethylpropanol, tromethamine, tetrahydroxypropyl ethylenediamine, citric acid, acetic acid, lactic acid, and salts of lactic acid including sodium lactate, potassium lactate, lithium lactate, calcium lactate, magnesium lactate, barium lactate, aluminum lactate, zinc lactate, sodium citrate, sodium acetate, silver lactate, copper lactate, iron lactate, manganese lactate, ammonium lactate, combinations thereof, and the like.

In some embodiments, solubilization of a lipophilic bioactive agent such as CoQ10 in a material that has both lipophilic and hydrophilic properties can assist in liposome formulation by forming water-dispersible CoQ10 for encapsulation by a high phosphatidylcholine lecithin, such as PHOSPHOLIPON® 85G.

Suitable solubilizing agents for the lipophilic bioactive agent include, for example, polyoxyalkylene dextrans, fatty acid esters of saccharose, fatty alcohol ethers of oligoglucosides (e.g., the alkylpolyglucosides such as TRITON™), fatty acid esters of glycerol (e.g., glycerol mono/distearate or glycerol monolaurate), and polyoxyethylene type compounds (e.g., polyoxyethylene, polyethylene glycol, polyethylene oxide, SOLUTOL™ CREOMOPHOR™, MACROGOL™, CARBOWAX™, POLYOXYL™) Suitable solubilizers also include polyethoxylated fatty acid esters of sorbitan (e.g., Polysorbates, such as TWEEN™, SPAN™, including Polysorbate 20 and Polysorbate 80), fatty acid esters of poly(ethylene oxide) (e.g., polyoxyethylene stearates), fatty alcohol ethers of poly(ethylene oxide) (e.g., polyoxyethylated lauryl ether, polyoxyethylene 20 oleyl ether (BRIJ 98)), alkylphenol ethers of poly(ethylene oxide) (e.g., polyethoxylated octylphenol), polyoxyethylene-polyoxypropylene block copolymers (also known as poloxamers, such as "PLURONICS", including PLURONIC F-127, a poloxamer 407 stabilizer), and ethoxylated fats and oils (e.g., ethoxylated castor oil, or polyoxyethylated castor oil, also known as polyethylene glycol-glyceryl triricinoleate), as well as combinations thereof.

In some embodiments, suitable solubilizing agents include Polysorbates, e.g. those sold under the brand name TWEEN™. Examples of such Polysorbates include Polysorbate 80 (TWEEN™ 80), Polysorbate 20 (TWEEN™ 20), Polysorbate 60 (TWEEN™ 60), Polysorbate 65 (TWEEN™ 65), Polysorbate 85 (TWEEN™ 85), and the like, and combinations including these materials with other similar surfactants, including ARLACEL® surfactants, as long as the HLB (Hydrophile-Lipophile Balance) of the surfactant and surfactant mixture favors the formation of an O/W type emulsion system.

In some embodiments the active agent(s) can be in solution with one or more organic solvents, or a combination thereof. The organic solvents can be water miscible or water immiscible. Suitable organic solvents include, but are not limited to, ethanol, methanol, tetrahydrofuran, acetonitrile, acetone, tert-butyl alcohol, dimethyl sulfoxide, N,N-dimethyl formamide, diethyl ether, methylene chloride, ethyl acetate, isopropyl acetate, butyl acetate, propyl acetate, toluene, hexane, heptane, pentane, 1,3-dioxolane, isopropanol, n-propanol, propionaldehyde, combinations thereof, and the like.

Methods of Manufacture

Methods for preparing inhalable pharmaceutical compositions in accordance with the invention include (i) hydrating a phospholipid, thereby forming a hydrated phospholipid; (ii) mixing the hydrated phospholipid, a hydrophobic bioactive agent, and an aqueous dispersion vehicle, thereby producing a mixture; and (iii) homogenizing the mixture, thereby producing a dispersion of liposomal particles comprising the phospholipid and hydrophobic bioactive agent dispersed within the aqueous dispersion vehicle and having an average diameter between about 30 and 500 nm. The ratio of hydrophobic bioactive agent:phospholipid is between about 5:1 and about 1:5, the hydrophobic bioactive agent is between about 0.1 and 30% w/w of the composition, and the phospholipid is between about 0.1 and 30% w/w of the composition. As a result of the specific formulation and method of manufacture, the composition is characterized by advantageous properties, for example, an average percent transmission (APT) between about 50 and 100% upon continuous aerosolization. Alternatively, the composition can be characterized by other pharmacokinetic properties, such as that, upon continuous aerosolization, the composition is capable of achieving a bioactive agent concentration of at least about 500 µg/g wet lung tissue or a total emitted dose (TED) of at least about 2,900 µg over 15 seconds.

Although specific embodiments are discussed herein, the dispersions and aerosols of the invention can be produced using various techniques within the purview of those skilled in the art. Such methods include fast freezing methods, precipitation methods, emulsion methods and high pressure homogenization methods, for example, as described in PCT/US2008/085669, the entire contents of which are hereby incorporated herein by reference. Aqueous dispersions according to the present invention can be prepared using any suitable method (e.g., microfluidization) such as those described in U.S. patent applications U.S. 61/313,605, U.S. 61/313,632, U.S. 61/385,194 and U.S. 61/385,107, the entire contents of each of which are hereby incorporated herein by reference.

Prior to mixing and homogenization, it can be helpful to use a solubilizer and/or heating, to help solubilize the lipophilic bioactive agent. The temperature of heating and time of heating can depend upon the specific lipophilic bioactive agent, the intrinsic thermal stability of the bioactive agent, and solubilizer utilized. For example, in some embodiments the lipophilic bioactive agent and solubilizer can be heated to a temperature of from about 40° C. to about 65° C., or from about 50° C. to about 60° C., or from about 50° C. to about 55° C., for a period of time from about 1 minute to about 60 minutes, or about 15 minutes to about 45 minutes, or about 20 minutes to about 30 minutes. The weight ratio of lipophilic bioactive agent to solubilizer may be about 1:1, in embodiments from about 1:1 to about 4:2, in other embodiments from about 1:2 to about 3:2.

For example, a solubilizer such as Polysorbate 80 can be capable of dissolving a lipophilic bioactive agent, in embodiments CoQ10, at high levels, with the lipophilic bioactive agent completely soluble in the solubilizer at a ratio of from about 1:2 to about 3:2, when heated to a temperature of from about 50° C. to about 55° C., a temperature which exceeds the melting point of CoQ10 (which is from about 47° C. to about 48° C.).

As noted above, the amount of solubilizer added to a lipophilic bioactive agent can depend upon the solubilizer, the lipophilic bioactive agent, and the phospholipids utilized to form the liposomes. In some embodiments, the solubilizer can be present in an amount from about 0.2% to 12% by weight, or about 1.5% to 6.5% by weight.

The solution of lipophilic bioactive agent and solubilizer can then be combined with a phospholipid (e.g., to form liposomes) which are in turn formed into a dispersion with an aqueous dispersion vehicle. To prepare the dispersion, the phospholipids and aqueous dispersion vehicle can be mixed together and heated, to approximately 50° C. to 60° C., e.g., 55° C., for between about 1-24 hours or for between about 1-8 hours, e.g., about 1 hour.

Suitable fast freezing methods for forming aerosolized particles include those referred to herein as spray freezing into liquid (SFL), as described in U.S. Pat. No. 6,862,890, the entire disclosure of which is incorporated by reference herein, and ultra-rapid freezing (URF), as described in U.S. Patent Application Publication No. 2004/0137070, the entire disclosure of which is incorporated by reference herein. In some embodiments, a suitable SFL method can include mixing an active agent with a solution agent, and spraying the effective ingredient-solution agent mixture through an insulating nozzle located at, or below, the level of a cryogenic liquid, so that the spray generates frozen particles. In some embodiments, a suitable URF method can include contacting a solution including an active agent and at least one freezable organic solvent with a cold surface so as to freeze the solution, and removing the organic solvent.

Suitable precipitation methods for forming aerosolized particles include those referred to herein as evaporative precipitation into aqueous solution (EPAS), as described in U.S. Pat. No. 6,756,062, the entire disclosure of which is incorporated by reference herein, and controlled precipitation (CP), as described in U.S. Patent Application Publication No. 2003/0049323, the entire disclosure of which is incorporated by reference herein. In some embodiments, a suitable EPAS method can include dissolving a drug or other active agent in at least one organic solvent to form a drug/organic mixture, spraying the drug/organic mixture into an aqueous solution, while concurrently evaporating the organic solvent in the presence of the aqueous solution to form an aqueous dispersion of the drug particles. In some embodiments, a suitable CP method can include recirculating an anti-solvent through a mixing zone, dissolving a drug or other active agent in a solvent to form a solution, adding the solution to the mixing zone to form a particle slurry in the anti-solvent, and recirculating at least a portion of the particle slurry back through the mixing zone.

Suitable emulsion methods for forming aerosolized particles include those referred to herein as HIPE (high internal phase emulsions), as described in U.S. Pat. Nos. 5,539,021 and 5,688,842, the entire disclosures of each of which are incorporated by reference herein. In some embodiments, a suitable HIPE method can include continuously merging into a disperser, in the presence of an emulsifying and stabilizing amount of a surfactant, a continuous phase liquid stream having a flow rate RJ, and a disperse phase liquid stream having a flow rate R2, and mixing the merged streams with a sufficient amount of shear with R2:R1 sufficiently constant, to form a high internal phase ratio emulsion without phase inversion or stepwise distribution of an internal phase into an external phase.

Suitable high pressure homogenization methods for forming aerosolized particles include those using homogenizer and microfluidizer, for example, as described in U.S. patent applications U.S. 61/313,605, U.S. 61/313,632, U.S. 61/385, 194 and U.S. 61/385,107.

The above methods can produce particles and aerosolized particles that are crystalline or amorphous in morphology. Advantageously, none of these methods require mechanical milling or other similar unit operations that can cause thermal degradation of the active agent.

One or more of the formulations components (e.g., the hydrophobic bioactive agent, phospholipid, and/or aqueous dispersion vehicle) can be homogenized by mixing at high shear to form a liposomal concentrate utilizing homogenizers, mixers, blenders and similar apparatus within the purview of those skilled in the art. In some embodiments, commercially available homogenizers including an Ultra-Turrax TP 18/10 Homogenizer or similar types of stator/rotor homogenizers made by Gifford-Wood, Frain, IKA and others as well as multi-stage homogenizers, colloid mills, sonolators or other types of homogenizers can be used to produce submicron liposomal dispersions of the lipophilic bioactive agent. The stator/rotor type homogenizers described above have an operational range of from about 100 rpm to about 15,000 rpm and can be supplied with a range of low shear, standard shear, and high shear head screens.

Homogenization can be carried out by mixing the two phases at suitable speeds of, for example, from about 5,000 rpm to about 15,000 rpm, in some embodiments about 5,000, 7,500, 10,000, 12,500, or 15,000 rpm or and value or range therebetween.

The shear rate of the homogenizer can also be increased or decreased independent of the speed of the homogenizing shaft by increasing or decreasing the size of the processing screen surrounding the homogenizer head.

In some embodiments, liposomes can be produced with both a standard emulsification screen and a high shear screen supplied for the Silverson L4RT homogenizer. Mixing can occur for a suitable period of time of less than about 90 minutes, in embodiments from about 2 minutes to about 60 minutes, in embodiments from about 5 minutes to about 45 minutes. In one embodiment, mixing may occur for up to almost 5 minutes. The resulting liposomes can have a particle size of from about 30 nm to about 500 nm, 50 nm to about 200 nm, from about 50 nm to about 150 nm, from about 50 nm to about 100 nm, from about 50 nm to about 75 nm, from about 75 nm to about 100 nm, from about 100 nm to about 150 nm.

In embodiments, the components being mixed can be heated to a temperature between about 45° C. to about 65° C., in embodiments from about 50° C. to about 55° C., and mixed with high shear homogenization at speeds and for periods of time described above to form submicron liposomes of CoQ10. Where the lipophilic bioactive agent is CoQ10, the processing temperature for the CoQ10 phase, the water/phospholipid phase, and the combined phases should not exceed about 65° C. in order to avoid oxidative degradation of the CoQ10. However, processing the mixture at a temperature from about 50° C. to about 60° C. can be desirable to obtain a desired viscosity of the concentrate of from about 5,000 cP to about 100,000 cP, in embodiments from about 15,000 cP to about 40,000 cP at from about 35° C. to about 45° C. In some embodiments, processing for extended periods, e.g., for up to about 60 minutes at the speeds noted above within this temperature range, should not adversely impact the integrity of the resulting liposomes.

The particle size of the lipophilic bioactive agent dispersion can be reduced by utilizing mechanical devices, such as, e.g., milling, application of ultrasonic energy, forming colloidal-sized droplets in a spray system, or by shearing the particles in a liquid flowing at high velocity in a restricted passage. Significant energy can be required to cleave bulk particles. The smaller particles increase the interfacial area of the active agent. In some embodiments, surfactants are used to reduce the interfacial energy, thereby stabilizing the dispersion. The particle size determines the total interfacial area and, thus, the interfacial energy that must be accommodated to achieve a stable system. As the particle size decreases, increasing energy is required to produce the particle, and since the total surface area increases, the surfactant must accommodate a greater interfacial energy.

In a preferred embodiment, the particle size of the bioactive agent dispersion is reduced by using a Microfluidizer. In some embodiments, in reducing the dispersion particle size, it can be desirable for the CoQ10 mixture to pass through several cycles in a Microfluidizer to obtain the desired particle size. For example, a phospholipid dispersion of a bioactive agent (e.g., CoQ10) of the invention can be passed through at least 5, 10, 20, 30, 40, 50, 60, 70, 80, 90 or 100 or more cycles in a Microfluidizer. Preferably, the phospholipid dispersion of a bioactive agent (e.g., CoQ10) is passed through a sufficient number of cycles in a Microfluidizer to obtain a preferred particle size, e.g., a particle size suitable for intranasal delivery, e.g., via a nebulizer.

Suitable Microfluidizers for use with the invention include, for example, the M1101P which is available through Microfluidics, Inc. (MFI). The M110P has a 75-μm passage and a F12Y interaction chamber. In processing M3, the Microfluidizer has an inlet pressure of 25,000 psi. Numerous other Microfluidizers are commonly known in the art and are contemplated as being suitable for use in the methods of the invention. Microfluidizers using in the invention can have an inlet pressure of at least about 20,000 psi, at least about 25,000 psi, and preferably at least about 30,000 psi.

In the examples provided herein, after a minimum of 10 cycles through M110P Microfluidizer with an F12Y interaction chamber with 75-μm passages, particles of less than 160 nm mean diameter were produced with lecithin and particles of about 110 nm were produced with DPPC. One of ordinary skill in the art will understand that the relative amounts of the liophilic bioactive agent (e.g., CoQ10), phospholipids (e.g., lecithin, DPPC or DMPC) and aqueous dispersion vehicle can be adjusted based upon desired properties such as the desired therapeutic use, aerosolization, pharmacokinetics, and/or pharmacodynamics. In the examples provided herein, the Microfluidizer operated at a pressure of about 30,000 PSI, although other pressures can be used in other embodiments.

Aerosolization

Methods in accordance with the invention can include aerosolizing the dispersion of liposomal particles, thereby forming a respirable aerosol comprising a plurality of droplets, each droplet comprising a dispersion of liposomal particles and having a mass median aerodynamic diameter (MMAD) between about 1 and 5 μm. Though, in some embodiments, particles can have diameters less than 1 μm and/or greater than 5 μm.

Figure 1B:
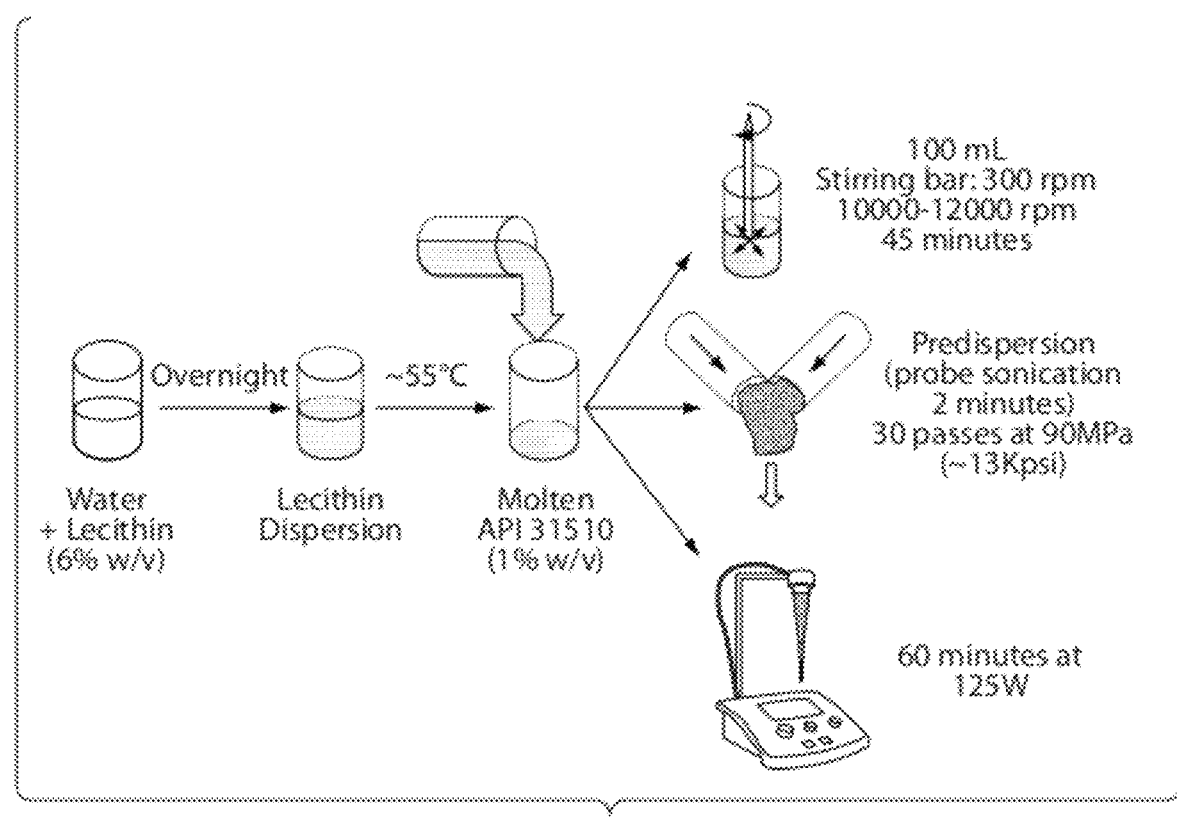
FIG. 1B shows a schematic of several manufacturing processes.
Figure 5:
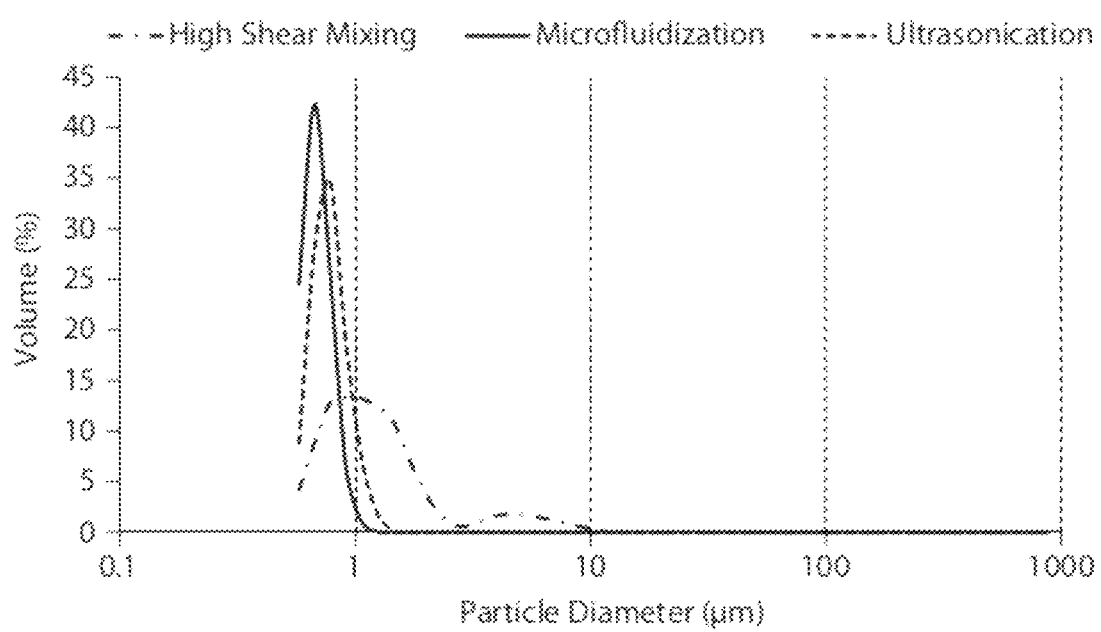
FIG. 5 shows particle size distributions of CoQ10 dispersions prepared using different manufacturing processes.

FIG. 1A shows a schematic of pulmonary delivery of an aqueous liposomal dispersion of a hydrophobic bioactive agent in accordance with the invention. The bulk drug is formulated into a phospholipid-stabilized aqueous dispersion with small (drug) particle size that is aerosolized using the vibrating-mesh nebulizer into droplets containing small drug particles. For definition purposes, "particle" is referring the internal phase of the aqueous dispersion and "droplet" is referring the result of becoming aerosol generated. In various embodiments, each droplet contains a certain number of drug particles. FIG. 1B shows three different tested manufacturing processes for obtaining an aqueous dispersion with a small drug particle size. For the purposes of FIG. 1B, a phospholipid dispersion containing 6% w/w of lecithin in water was added to the molten CoQ10 (1% w/w) at 55° C. The formulation was then processed as follows (1) High Shear Mixing (Ultra-Turrax® TP 18/10 Homogenizer with 8 mm rotor blade, IKA-Werke, Staufen, Germany): 100 mL of formulation was stirred at 300 rpm and high shear mixed at 10-12 thousands rpm for 45 minutes; (2) Microfluidization (M-110Y High Pressure Pneumatic Microfluidizer®, Microfluidics, Newton, Mass. USA): This process works by having two jet streams in opposite directions. Each pass represents one chance that the drug particles have to collide against each other during this process, breaking apart and becoming smaller. The formulation was predispersed using probe sonication for 2 minutes, followed by 30 passes at approximately 13 Kpsi; or (3) Ultrasonication (Omni Sonic Ruptor-250® Ultrasonic Homogenizer with 5/32" (3.9 mm) Micro-Tip Probe, Omni International, Kennesaw, Ga., USA): at 125 W for 60 minutes. A comparison of the results of these different manufacturing methodologies are shown in FIG. 5 and discussed in further detail below.

Production and delivery of aerosols in accordance with the present invention can be achieved through any suitable delivery means for continuous nebulization or aqueous liposomal dispersions, including nebulizers. The most suitable delivery means will depend upon the active agent to be delivered to the lung, the other components of the formulation, the desired effective amount for that active agent, and characteristics specific to a given patient. Given the present disclosure, the details of selecting and operating such devices are within the purview of those skilled in the art.

In various embodiments, aerosols in accordance with the invention can be delivered by an ultrasonic wave nebulizer, a jet nebulizer, a soft mist inhaler, an ultrasonic vibrating mesh nebulizer or other nebulizer utilizing vibrating mesh technology. For example, suitable ultrasonic wave nebulizers include Omron NE-U17 available from Omron Corporation of Japan and Beurer Nebulizer IH30 available from Beurer GmbH of Germany. Suitable jet nebulizers include, for example, AquaTower available from A&H Products, Inc. of Oklahoma. Suitable soft mist nebulizers include, for example, Respimat Soft Mist available from Boehringer Ingelheim GmbH of Germany. Suitable vibrating mesh nebulizers include, for example, Pari eFlow available from Pari Pharma GmbH of Germany, Respironics i-Neb available from Respironics Inc. of Pittsburg, Pa., Omron MicroAir available from Omron Corporation of Japan, Beurer Nebulizer IHSO available from Beurer GmbH of Germany, and Aerogen Aeroneb available from Aerogen Ltd. of Ireland. With respect to the present invention, a nebulizer is selected for inhalation therapy over pressurized Metered Dose Inhalers (pMDIs) and Dry Powder Inhalers (DPIs) by virtue of their capability of delivering high amounts of drugs via passive breathing. Therefore, patients with impaired pulmonary function (e.g. lung cancer patients) are not expected to experience difficulty during administration of the drug.

While the instant disclosure has discussed inhalation formulations in some detail, depending on the specific conditions being treated, the lipophilic bioactive agents, described above can also be formulated and administered by other systemic and/or local routes. For example, aerosols can be delivered selectively to one or more regions of the respiratory tract, mouth, trachea, lungs, nose, mucosa, sinuses, or a combination thereof. Delivery can achieve one or more of topical, local, or systemic delivery, or a combination thereof. Alternatively, aerosols can also be used for non-inhalation delivery. Compositions of the present invention can also be administered in vitro to a cell (for example, to induce apoptosis in a cancer cell in an in vitro culture or for scientific, clinical, or pre-clinical experimentation) by simply adding the composition to the fluid in which the cell is contained.

Methods of Treatment

Compositions of the present disclosure can be utilized to administer lipophilic bioactive agents for the treatment of any disease or condition which may benefit from the application of the lipophilic bioactive agent, including those disclosed in International Publication No. WO 2005/069916, the entire disclosure of which is incorporated by reference herein.

Method for administering an inhalable pharmaceutical composition in accordance with the present invention can include the steps of: (i) aerosolizing a dispersion of liposomal particles, thereby forming a respirable aerosol comprising a plurality of droplets having a mass median aerodynamic diameter (MMAD) between about 1 and 5 µm and (ii) delivering a therapeutically effective amount of the hydrophobic bioactive agent to a lung of a subject in need of treatment. Further, the dispersion of liposomal particles has an average diameter between about 30 and 500 nm, each liposomal particle comprising a hydrophobic bioactive agent and a phospholipid dispersed within an aqueous dispersion vehicle. Furthermore, the ratio of hydrophobic bioactive agent:phospholipid is between about 5:1 and about 1:5, the hydrophobic bioactive agent is between about 0.1 and 30% w/w of the composition, and the phospholipid is between about 0.1 and 30% w/w of the composition.

As a result of the specific formulation and method of manufacture, the composition is characterized by advantageous properties, for example, an average percent transmission (APT) between about 50 and 100% upon continuous aerosolization. Alternatively, the composition can be characterized by other pharmacokinetic properties, such as that, upon continuous aerosolization, the composition is capable of achieving a bioactive agent concentration of at least about 600 µg/g wet lung tissue or a total emitted dose (TED) of at least about 2,900 µg over 15 seconds.

Other pharmacokinetic properties can include mass fraction deposited, amount of drug and/or formulation delivered to the target, and residence time at the target. In some embodiments, the invention can be used to deposit a mass fraction of at least about 1, 5, 10, 15, or 20%. The invention can also be used to facilitate delivery of over 0.25 µg/g of an active agent to the deep lung. In certain embodiments delivery to the lung can be of at least about 1, 5, 10, 15, 20, 25, 30, 50, 100, 200, 300, 400, or 500 µg/g of bioactive agent in lung tissue. Furthermore, the formulations can remain in the lungs (e.g., "residence time") for a period of at least about 2, 4, 6, 8, 10, 12, 24, or 48 hours.

The terms "pharmaceutically effective amount" and "therapeutically effective amount" as used herein include a quantity or a concentration of a bioactive agent or drug that produces a desired pharmacological or therapeutic effect when administered to an animal subject, including a human. The amount of active agent or drug that includes a pharmaceutically effective amount or a therapeutically effective amount can vary according to factors such as the type of drug utilized, the potency of the particular drug, the route of administration of the formulation, the system used to administer the formulation, combinations thereof, and the like.

The terms "treatment" or "treating" herein include any treatment of a disease in a mammal, including: (i) preventing the disease, that is, causing the clinical symptoms of the disease not to develop; (ii) inhibiting the disease, that is, arresting the development of clinical symptoms; and/or (iii) relieving the disease, that is, causing regression of the clinical symptoms.

In some embodiments, compositions of the present disclosure can be utilized in the treatment of cancer. As used herein, "cancer" refers to all types of cancer or neoplasm or malignant tumors found in mammals, including, but not limited to: leukemias, lymphomas, melanomas, carcinomas and sarcomas. As used herein, the terms "cancer," "neoplasm," and "tumor," are used interchangeably and in either the singular or plural form, refer to cells that have undergone a malignant transformation that makes them pathological to the host organism.

Primary cancer cells (that is, cells obtained from near the site of malignant transformation) can be readily distinguished from non-cancerous cells by well-established techniques, including histological examination. The definition of a cancer cell, as used herein, includes not only a primary cancer cell, but any cell derived from a cancer cell ancestor. This includes metastasized cancer cells, and in vitro cultures and cell lines derived from cancer cells.

When referring to a type of cancer that normally manifests as a solid tumor, a "clinically detectable" tumor is one that is detectable on the basis of tumor mass, e.g., by procedures such as CAT scan, MR imaging, X-ray, ultrasound or palpation, and/or which is detectable because of the expression of one or more cancer-specific antigens in a sample obtainable from a patient.

Examples of cancers include cancer of the brain, breast, pancreas, cervix, colon, head and neck, kidney, lung, non-small cell lung, melanoma, mesothelioma, ovary, sarcoma, stomach, uterus and Medulloblastoma.

The term "sarcoma" generally refers to a tumor which is made up of a substance like the embryonic connective tissue and is generally composed of closely packed cells embedded in a fibrillar or homogeneous substance. Examples of sarcomas which can be treated with compositions including aerosolized particles of the present disclosure, and optionally a potentiator and/or chemotherapeutic agent include, but not limited to, a chondrosarcoma, fibrosarcoma, lymphosarcoma, melanosarcoma, myxosarcoma, osteosarcoma, adipose sarcoma, liposarcoma, alveolar soft part sarcoma, ameloblastic sarcoma, botryoid sarcoma, chloroma sarcoma, chorine carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectatic sarcoma.

The term "melanoma" includes a tumor arising from the melanocytic system of the skin and other organs. Melanomas which can be treated with compositions including aerosolized particles of the present disclosure include, but are not limited to, acral-lentiginous melanoma, amelanotic melanoma, benign juvenile I melanoma, Cloudman's melanoma, 891 melanoma, Harding-Passey melanoma, juvenile melanoma, lentigo maligna melanoma, malignant melanoma, nodular melanoma, subungual melanoma, and superficial spreading melanoma.

The term "carcinoma" refers to a malignant new growth made up of epithelial cells tending to infiltrate the surrounding tissues and give rise to metastases. Carcinomas which can be treated with compositions including aerosolized particles of the disclosure include, but are not limited to, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lyrnphoepithelial carcinoma, carcinoma medullare, medullary carcinoma, melanotic carcinoma, carcinoma moue, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solenoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and the like.

Additional cancers which can be treated with compositions including aerosolized particles of the present disclosure include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary; bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

Although various cancers have been discussed in detail, the compositions and methods of the invention are applicable to other respiratory, oral, nasal, sinus, and pulmonary pathologies including, but not limited to, asthma, allergies, chronic obstructive pulmonary disease, chronic bronchitis, acute bronchitis, emphysema, cystic fibrosis, pneumonia, tuberculosis, pulmonary edema, acute respiratory distress syndrome, pneumoconiosis, interstitial lung disease, pulmonary edema, pulmonary embolism, pulmonary hypertension, pleural effusion, pneumothorax, mesothelioma, amyotrophic lateral sclerosis, myasthenia gravis, and lung disease.

EXAMPLES

The following Examples are intended to be illustrative only and are not intended to limit the scope of the invention.

Example 1

Development and Characterization of Phospholipid-Stabilized Submicron Aqueous Dispersions of CoQ10 Adapted for Continuous Nebulization This example provides methods for developing suitable formulations for pulmonary delivery of hydrophobic drugs using CoQ10 as a case study. Excipients (e.g., phospholipids) and an aerosolization device (e.g., Aeroneb Pro® vibrating-mesh nebulizer) were selected after an initial study (data not shown). Initial characterization of the bulk drug using X-ray diffraction (XRD), Differential Scanning calorimetry (DSC), Laser Diffractometry (LD) and Scanning Electron Microscopy (SEM) was performed. High shear mixing, high pressure homogenization or ultrasonication was then evaluated as feasible manufacturing processes to obtain small particle size dispersions of CoQ10. Following selection of an appropriate process, parameters affecting drug particle size were studied. Using LD and gravimetrical analysis, nebulization was evaluated to assess the performance of the drug-excipients-device combination. CoQ10 powder studied was crystalline with a melting point approximately at 51° C. with a particle size of 30 μm. Therefore, particle downsizing was deemed necessary for pulmonary delivery. Microfluidization was found to be a suitable method to prepare submicron drug particles in aqueous dispersions. The number of passes and type of phospholipids (lecithin or Dipalmitoyl Phosphatidylcholine—DPPC) used affected final drug particle size of the dispersions. Nebulization performance of lecithin-stabilized CoQ10 dispersions varied according to number of passes in the microfluidizer. Furthermore, the rheology of these dispersions appeared to play a role in the aerosol generation from the active vibrating mesh nebulizer used. In conclusion, aqueous dispersions of CoQ10 were adequately produced using a microfluidizer with characteristics that were suitable for pulmonary delivery with a nebulizer.

Materials and Methods

Materials:

Coenzyme Q10 was supplied by Asahi Kasei Corp. (Tokyo, Japan). Lecithin (granular, NF) was purchased from Spectrum Chemical Mfg. Corp. (Gardena, Calif., USA). Genzyme Pharmaceuticals (Liestal, Switzerland) provided 1,2-dipalmitoyl-sn-glycero-3phosphocholine (DPPC). Sodium chloride (crystalline, certified ACS) was acquired from Fisher Chemical (Fisher Scientific, Fair lawn, NJ, USA) and the deionized water was obtained from a central reverse osmosis/demineralizer system commonly found in research laboratories. The dispersant 1,3-propanediol (98%) was purchased from Sigma-Aldrich (St. Louis, Mo., USA). Ethanol 200 proof USP was purchased from Decon Laboratories (King of Prussia, Pa., USA).

Bulk Characterization of CoQ10

X-Ray Diffraction (XRD):

Testing was performed using a Philips Model 1710 X-ray diffractometer (Philips Electronic Instruments Inc., Mahwah, N.J., USA) with primary monochromated radiation (CuKα1, $\lambda$=1.54056 Å) emitting at an accelerating voltage of 40 kV and 30 mA. The CoQ10 powder was placed into a stage and the sample was scanned for diffraction patterns from 5° to 50° at 0.05° intervals of 2θ angles, with dwell time of 3 seconds.

Differential Scanning Calorimetry (DSC):

DSC testing was performed using a 2920 Modulated DSC (TA Instruments, New Castle, Del., USA) and analyzed using TA Universal Analysis 2000 Software. Powder of CoQ10 was weighed (10.5 mg) into aluminum pan (kit 02190041, Perkin-Elmer Instruments, Norwalk, Conn., USA) and crimped. At a heating rate of 10° C./min, the thermal behavior of the sample was analyzed from 10 to 120° C.

Laser Diffraction (LD):

Bulk CoQ10 powder was dispersed in 20% (v/v) 1,3-propanediol in deionized water for analysis of particle size distribution. This dispersed sample was then added to a small cell apparatus in a Malvern Mastersizer S® instrument (Malvern Instruments, Worcestershire, UK) equipped with a 300 mm lens until 5-10% obscuration was attained. The internal phase and dispersant refractive indexes were 1.45 and 1.33, respectively.

Scanning Electron Microscopy (SEM):

Analysis of physical appearance and estimation of particle size of bulk CoQ10 were performed using an SEM. An aluminum stage with adhesive carbon tape held the powder sample. Coating was carried out in a rotary-planetary-tilt stage with platinum-iridium using a Cressington Sputter Coater 208 HR (Cressington Scientific Instruments, Watford, England) under argon atmosphere. The SEM pictures were captured using SmartSEM® graphical user interface software in a Carl Zeiss Supra® 40VP Scanning Electron Microscope (Carl Zeiss AG, Oberkochen, Germany) operated at a working distance of 19 mm and at 5 kV of Electron High Tension (EHT).

Development of a Manufacturing Methodology

Three different manufacturing processes were tested in the present example in order to obtain an aqueous dispersion CoQ10 with a small drug particle size. Similar methods can be adapted to further optimize CoQ10 formulations and to provide formulations for other hydrophobic drugs. A phospholipid dispersion containing 6% w/w of lecithin (as the example phospholipid) in water was added to the molten CoQ10 (1% w/w) at 55° C. The phospholipid concentration was above the critical micellar concentration (e.g., for lecithin, depending on the source and processing method, CMC varies from 1.3 to 5.5 mg/mL). The formulation was then processed as follows.

High Shear Mixing:

One hundred milliliters of formulation was stirred at 300 rpm and high shear mixed at 10,000-12,000 rpm for 45 minutes using an Ultra-Turrax® TP 18/10 Homogenizer with 8 mm rotor blade (IKA-Werke, Staufen, Germany).

High Pressure Homogenization:

High pressure homogenization was achieved using a microfluidization process. Each pass represents an opportunity for the drug particles to collide against each other, thereby breaking apart and becoming smaller. The formulation was predispersed using probe sonication for 2 minutes, followed by 30 passes at approximately 30,000 psi using an M-110Y High Pressure Pneumatic Microfluidizer® (Microfluidics, Newton, Mass. USA).

Ultrasonication:

The formulation was ultrasonicated at 125 W for 60 minutes using an Omni Sonic Ruptor-250® Ultrasonic Homogenizer with 5/32 inch (3.9 mm) with a micro-tip probe (Omni International, Kennesaw, Ga., USA).

Formulation Development

After selection of the manufacturing process, formulations were prepared with high pressure homogenization to determine the effect of the selected parameters and type of phospholipid on the particle size distribution of the drug dispersion. During preliminary studies, it was observed that the high solute concentration of formulations containing 6% w/w of lecithin did not produce aerosol from the Aeroneb Pro® vibrating-mesh micropump nebulizer. Further preliminary studies also showed that formulations containing a reduced concentration of lecithin (1% w/w, at 1:1 drug-to-lipid ratio) have presented sufficient stability for evaluation of nebulization performance following preparation. Therefore, reduction of phospholipid concentration was necessary while simultaneously keeping the concentration of CoQ10 constant at an adequate drug-to-lipid ratio.

Following hydration, a phospholipid dispersion containing 1% w/w of phospholipid (lecithin or DPPC) in water was added to the molten CoQ10 (1% w/w) at 55° C. The formulation was then predispersed using high shear mixing (Ultra-Turrax® TP 18/10 Homogenizer with 8 mm rotor blade, IKA-Werke, Staufen, Germany) for up to 5 minutes at 20,000 rpm. Subsequently, the formulation was passed through an M-110P Bench-top Microfluidizer® (Microfluidics, Newton, Mass. USA) up to 100 times at approximately 30,000 psi while maintaining the temperature between 50 and 60° C.

In testing the effects that the type of phospholipid and number of passes have on particle size distribution of the formulations, phospholipid dispersions were hydrated for approximately 1 hour without stirring (Table 1, Formulations A and B). Formulations were then passed through a microfluidizer 10, 20, 30, 40 and 50 times when comparing different phospholipids; 20, 50, 70 and 100 times when evaluating the effect from number of passes (Table 9). For nebulization performance tests, the phospholipid dispersions were hydrated overnight with stirring and 0.9% w/v of sodium chloride was added to the final formulation (Table 1, Formulation C)."

The particle size distributions of the formulations were then analyzed using Laser Diffraction (LD) and/or Dynamic Light Scattering (DLS). The surface tension, zeta potential and rheology were also evaluated. For nebulization performance, aerosol output was performed using LD and gravimetrical analysis.

Characterization of Formulations

Particle Size Distribution:

Particle size distribution testing of the dispersed formulations was performed with LD using a wet sample dispersion unit stirring at 1,000 rpm coupled to a Malvern Spraytec® (Malvern Instruments, Worcestershire, UK) equipped with a 300 mm lens. The dispersed formulations were added to distilled water (dispersant) until approximately 5% laser obscuration was attained. The internal phase and dispersant refractive indexes were set as 1.45 and 1.33, respectively. A timed measurement was performed for 45 seconds with 1 second sampling periods (a total of 45 measurements). Results are presented as Dv(X) and span, where X is the cumulative percentile of particles under the referred size (e.g. Dv(50) corresponds to the median volume of the particles). Span is a measurement of particle size distribution calculated as [Dv(90)−(10)]/Dv(50)]. A higher span indicates a more polydisperse particle size distribution.

In addition, the nanoparticle hydrodynamic diameter of the dispersed formulations was characterized with DLS using a Malvern Zetasizer Nano S® (Malvern Instruments, Worcestershire, UK) at 25° C. and pre-equilibrated for 2 minutes. The intercept of the correlation function was between 0.5 and 1.0. The dispersion was diluted with distilled water.

Surface Tension:

Surface tension testing was performed using a TA.XT.plus Texture Analyzer (Texture Technologies, Scarsdale, N.Y., USA) from the maximum pull on a disk as described in the previous chapter. Briefly, the container and glass disk probe were thoroughly degreased, cleaned with ethanol and allowed to dry. The probe was attached to the texture analyzer arm, and lowered until the bottom surface of the probe contacted the surface of the liquid formulation contained in the reservoir. The temperature of the liquid was measured and recorded. At the start of testing, the probe was raised from the surface of the liquid at a constant speed (0.05 mm/s) for 10 mm, while the texture analyzer registered at 5 points per second the force exerted as a function of either time or distance. Using the maximum (detachment) force the surface tension was calculated using Equation 1 below:

$$x/k=0.0408687+6.20312*(x\hat{}2/v)-0.0240752(x\hat{}2/v)\hat{}2 \quad \text{(Equation 1)}$$

Where x is probe radius, v is volume and k is the meniscus coefficient. The density values used to calculate surface tension were assumed to be the same as the density of water at the measurement temperature.

Zeta Potential:

Electrophoretic light scattering was used to perform zeta potential testing with a ZetaPlus Zeta Potential Analyzer (Brookhaven Instruments Corp., Holtsville, N.Y., USA). The samples were analyzed at a constant temperature of 25° C. and constant (neutral) pH. Samples were diluted with distilled water to conductance values of 300 to 550 μS. Each sample was subjected to 10 runs each, with a 5 second interval between measurements.

Rheology:

Rheological behavior of the dispersed formulations were tested using a AR-G2 rheometer (TA Instruments, New Castle, Del., USA) equipped with a cone-and-plate geometry (cone diameter: 40 mm; truncation: 54 μm). Zero-gap and rotational mapping, respectively, were performed prior to testing. All measurements were executed with fresh sample dispersion at a constant temperature of 25° C. with no pre-shear. Excess sample around the edge of the probe was trimmed and water added to the solvent trap compartment. The samples were measured at steady state flow step over a range of shear rates (300 to 10 $s^{-1}$) decreasing logarithmically (10 points per decade). The upper limit of shear rate was determined by hydrodynamic limitations (high probe speed will cause the liquid sample to spill away from the measurement zone). The sample period was 10 seconds and considered in equilibrium after 2 consecutive analyses within 5% tolerance, not exceeding a maximum point time of 2 minutes. The results were evaluated using Rheology Advantage Data Analysis software (TA Instruments, New Castle, Del., USA).

Nebulization Performance:

Based on previous experience, the performance of vibrating-mesh nebulizers can be affected by mesh clogging, resulting in variable aerosol emission (e.g., intermittent mist), since this formulation is a dispersed system. To analyze the nebulization performance of these formulations, we evaluate the changes in transmission over time from LD technique measurements. The nebulization performance of the dispersions was evaluated using the "open bench" method with a Malvern Spraytec® instrument (Malvern Instruments, Worcestershire, UK) equipped with 300 mm lens. The nebulizer reservoir was positioned with the membrane at 25 mm above the upper edge of the laser beam and a distance of 25 mm between the lens and the center of the aerosol cloud. Air suction was positioned 10 cm beneath the laser beam. The device and air suction apparatus positions were maintained still throughout the whole measurement period. The internal phase and dispersant refractive indexes were 1.33 (water) and 1.00 (air), respectively. Formulation (10 mL) was added to the nebulizer reservoir. At the start of nebulization, aerosol characteristics were continuously measured every second for 15 minutes. The slope of the transmission-time curves (transmittograms) were considered when comparing the different phospholipid formulations.

In addition, the Total Aerosol Output (TAO) was gravimetrically measured for each of the formulations studied. Before aerosolization, the nebulizer was weighed after each formulation was dispensed into the reservoir. The remaining formulation in the nebulizer reservoir was re-weighed after undergoing 15 minutes of nebulization. The difference in weight before and after nebulization results in the calculated TAO. The weight of the nebulizer mouthpiece was not considered during the measurements.

Importantly, neither transmittogram nor TAO provide information regarding drug output from the nebulizer. Information is limited solely to total mass output (droplets emitted over time). In the aerosolization of these dispersions, droplets not containing drug particles (empty droplets) are potentially generated. However, our purpose with this test is to investigate the capability of a nebulizer such as the Aeroneb Pro® nebulizer to continuously and steadily aerosolize the aqueous dispersions of Coenzyme Q10 over time. Intermittent mist can be identified in the transmittograms while TAO elucidates the magnitude of total mass being aerosolized. Saline solution (12 mL of 0.9% w/v NaCl in water) was used as the control.

Statistical Analysis:

The data is expressed as mean±standard deviation with the exception of surface tension and zeta potential results, which were expressed as mean±standard error. For rheology studies, standard errors were provided by the software used to analyze the best fit of the results to the rheological models. Samples were analyzed at least in triplicate and evaluated for statistical differences with One-Way ANOVA for significance when p<0.05 using NCSS/PASS software Dawson edition. Post hoc comparisons were performed to identify statistically significant differences among groups using Tukey-Kramer method. A paired t-test was performed to analyze statistical differences (p<0.05) within the same formulation for stability of drug particle size over time and to analyze the effect of different phospholipids processed at the same microfluidization conditions.

Results and Discussion

This example demonstrates the feasibility of the development of a suitable formulation of hydrophobic drugs (e.g., CoQ10) for pulmonary delivery. In particular, the example demonstrates how to different physicochemical properties of drug dispersions can influence the nebulization performance. The example also demonstrates how, transmission data from LD and gravimetrical analysis of nebulizer output can be used to evaluate steady aerosolization as a function of time.

Figure 2:
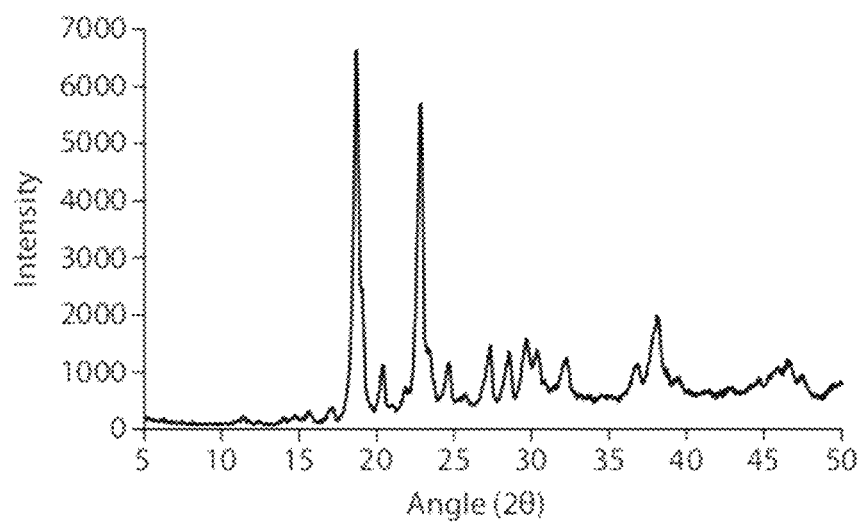
FIG. 2 shows an X-Ray diffraction pattern of bulk powdered CoQ10.
Figure 3:
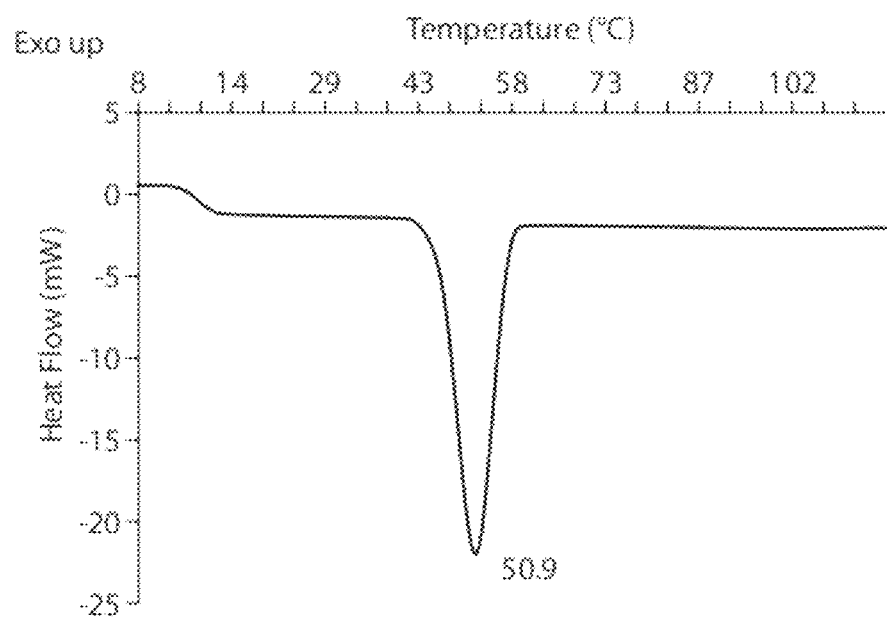
FIG. 3 shows a differential scanning calorimetry thermogram of bulk powdered CoQ10.
Figure 4:
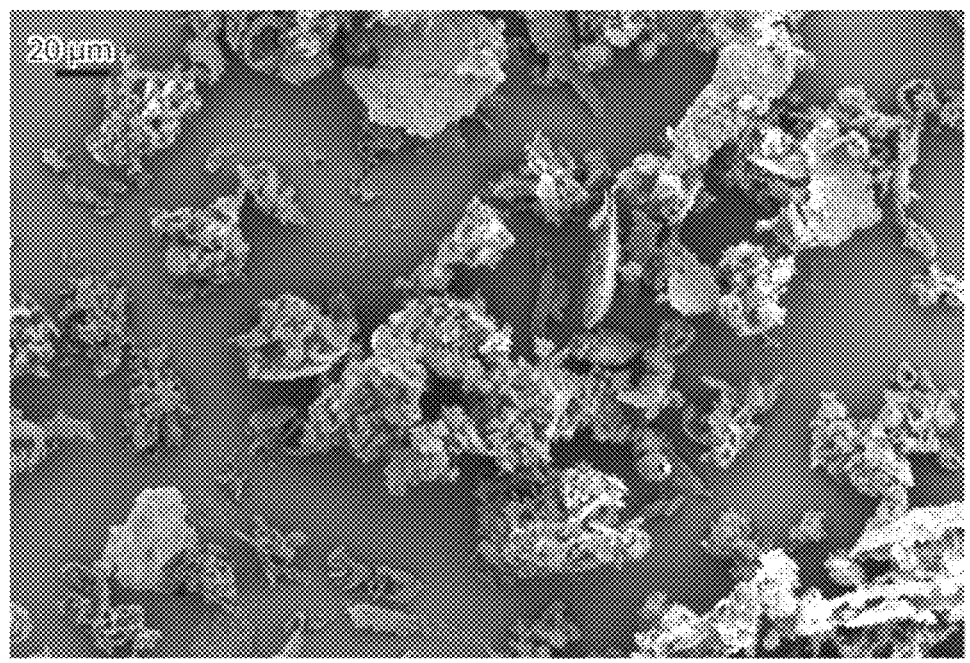
FIG. 4 shows a Scanning Electron Microscopy (SEM) picture of bulk powdered CoQ10.

The XRD pattern of bulk CoQ10 shows two high intensity peaks (2θ) at approximately 18.65 and 22.80, indicating the crystalline structure of CoQ10 (FIG. 2). An endothermic peak at approximately 51° C. in the DSC thermogram indicates the low melting point of this compound (FIG. 3). The CoQ10 drug particles are unsuitable for pulmonary delivery as bulk material, with Dv(50) of 29.87 µm and span value of 2.051. The magnitude of the particle dimensions were also confirmed by SEM pictures (FIG. 4). The first approach to reduce particle size was performed with ball milling for 18 hours, which was unsuccessful because the CoQ10 turned into a cluster of drug mass. This visual observation was confirmed by an increased particle size (Dv(50)=29.87 µm, span=2.282). Due to the low melting point of CoQ10, heat generated during the process and mechanical impact may have both contributed to this outcome. Similar results were found when bulk powder was cryomilled (data not shown).

Therefore, an alternative approach to engineering CoQ10 particles for pulmonary delivery was required. High shear mixing, high pressure homogenization and ultrasonication were tested. The results shown in FIG. 5 indicate that formulations prepared using shear force presented drug particles in dispersion with nearly a bimodal distribution, confirmed by a higher span value and Dv(50) around 1 µm (Table 2). Both microfluidization and ultrasonication presented a monodisperse, unimodal distribution with a Dv(50) value in the submicron range, so each method is capable of preparing a formulation with small drug particle size, to varying degrees and with varying size distributions.

Figure 6:
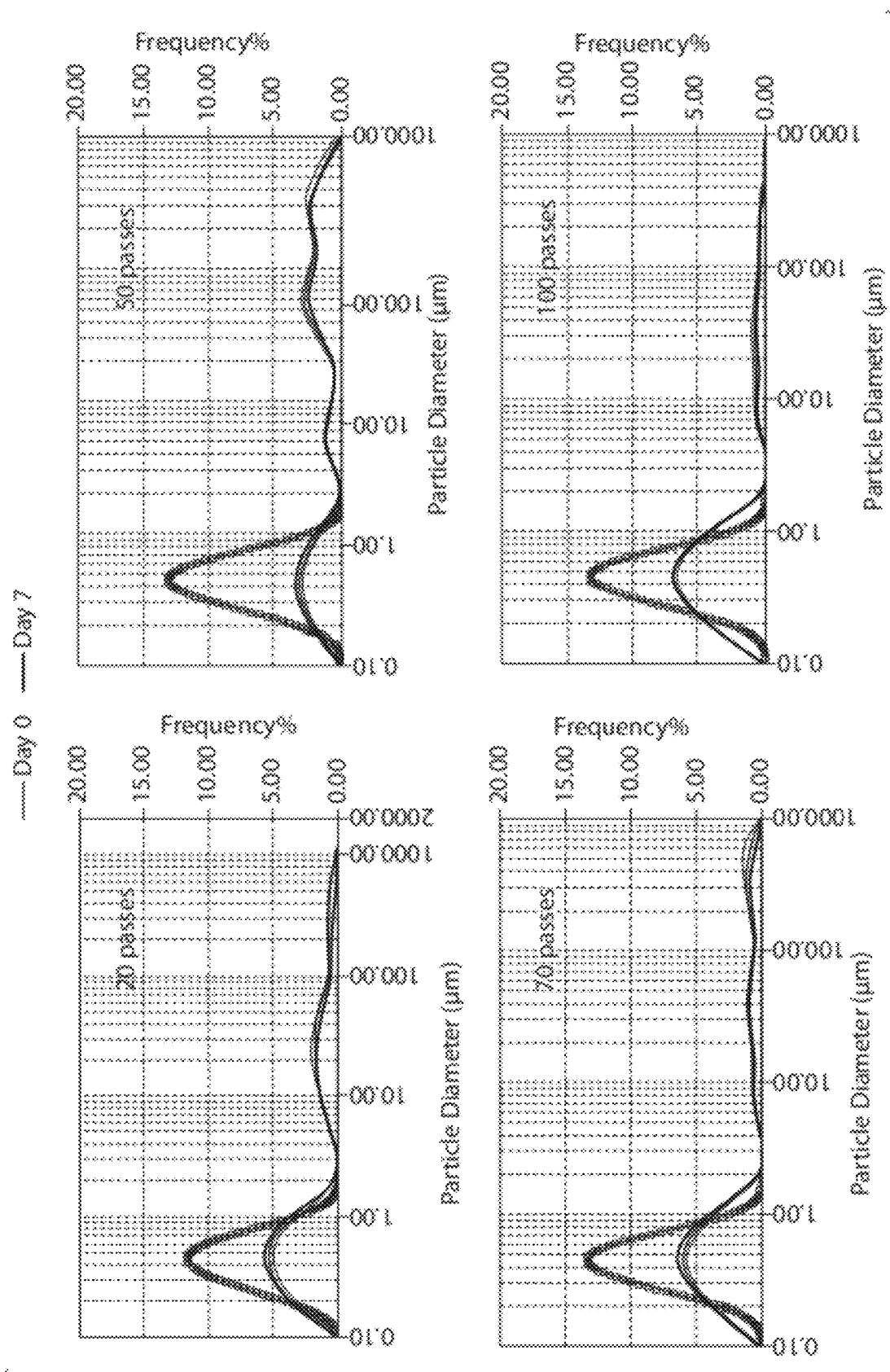
FIG. 6 shows particle size distributions, obtained by Laser Diffraction (LD), of aqueous dispersions of CoQ10 following preparation in the microfluidizer and after 7 days (Formulation A, Table 1).
Figure 7:
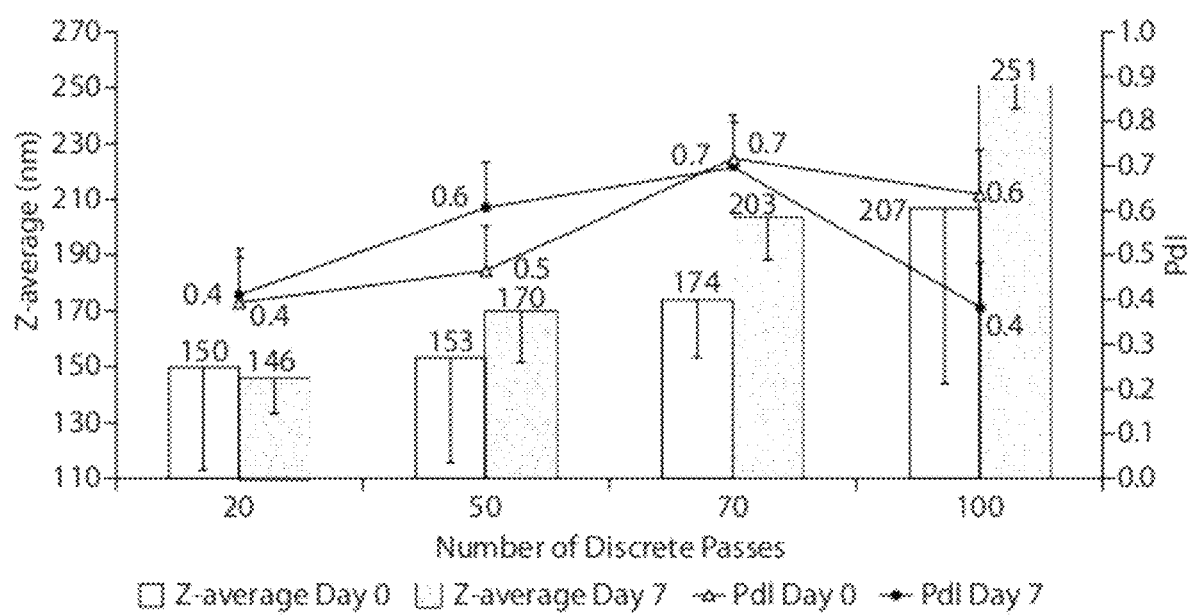
FIG. 7 shows Z-average and PdI values of aqueous dispersions of CoQ10 following preparation in the microfluidizer and after 7 days (Formulation A, Table 1). Statistical differences were not found for drug particle size distribution characteristics (Z-average and PdI) neither in formulations prepared with different number of microfluidization passes and analysed following preparation nor when the same formulations were compared at days 0 and 7.

After selecting a process, Formulation A was processed to determine the influence relating the number of passes in the microfluidizer to drug particle size stability (Table 1). The LD results show that, following preparation, all formulations presented particle size distribution in the submicron range (FIG. 6). After 7 days, the formulations presented larger particles, as compared to the size immediately after preparation, regardless of the number of passes. The DLS results indicate that increasing the number of passes above 50 does not appear to provide smaller hydrodynamic diameters or more monodisperse systems (FIG. 7). A trough in particle size as function of number of passes has been previously reported and attributed to a secondary particle growth due to fusion or Ostwald ripening during repeated homogenization. Nevertheless, no statistical difference was found for drug particle sizes between days 0 and 7 for any individual preparation with any different number of passes.

Figure 8:
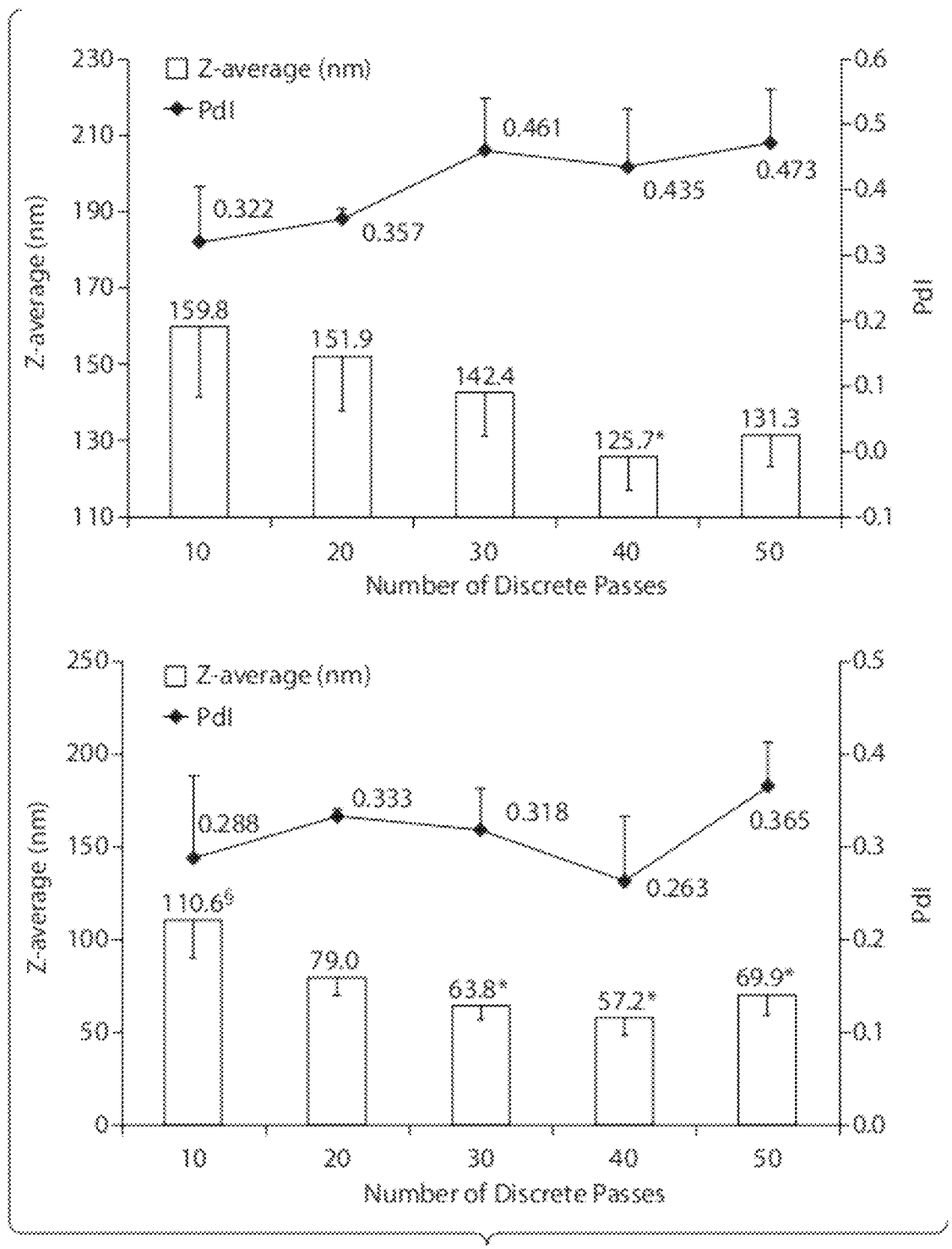
FIG. 8 shows hydrodynamic diameters and polydispersity of aqueous dispersions of CoQ10 (Formulation B, Table 1) following preparation in the microfluidizer using lecithin (top) or DPPC (bottom). (*$P<0.05$ when compared to 10 passes; § Not statistically different when compared to the lecithin dispersion prepared with same number of microfluidization passes).

Reduction in number of passes and evaluation of different phospholipids were investigated using Formulation B (Table 1). DLS analysis shows that drug particle size decrease for increased number of microfluidization passes (e.g., up to 50 passes) for both lecithin and DPPC dispersions of CoQ10 (FIG. 8). The DPPC formulation presented smaller particle sizes than the lecithin dispersions of CoQ10 at the same microfluidization conditions (e.g. number of discrete passes), with Z-averages in the ranges of 50-120 nm and 120-170 nm, respectively. Although the DPPC colloidal dispersion presented smaller PdI values than lecithin-stabilized formulations, both presented high polydispersity (PdI>0.2). This result indicates that no more than 50 passes are needed to obtain formulations with small particle sizes; the final colloidal system will depend on the phospholipid utilized.

After it was shown that small drug particle dispersion of CoQ10 can be prepared, ability to steadily nebulize these formulations was studied, along with the physicochemical properties influencing nebulization performance. Intermittent mist, which is undesirable, can occur when vibrating-mesh nebulizers generate aerosols from suspended dosage forms. Therefore, formulations were evaluated for a lack of intermittent mist, indicating aerosolization continuity throughout the nebulization event.

In this example, a Malvern Spraytec® was used to analyze transmission as a function of time, to select dispersed formulations that continuously aerosolize in an Aeroneb Pro® nebulizer. Alternative method for evaluating changes in nebulized droplet concentration over time are described in General Chapter <1601> of the United States Pharmacopoeia (USP) on the characterization of nebulizer products.

Figure 9C:
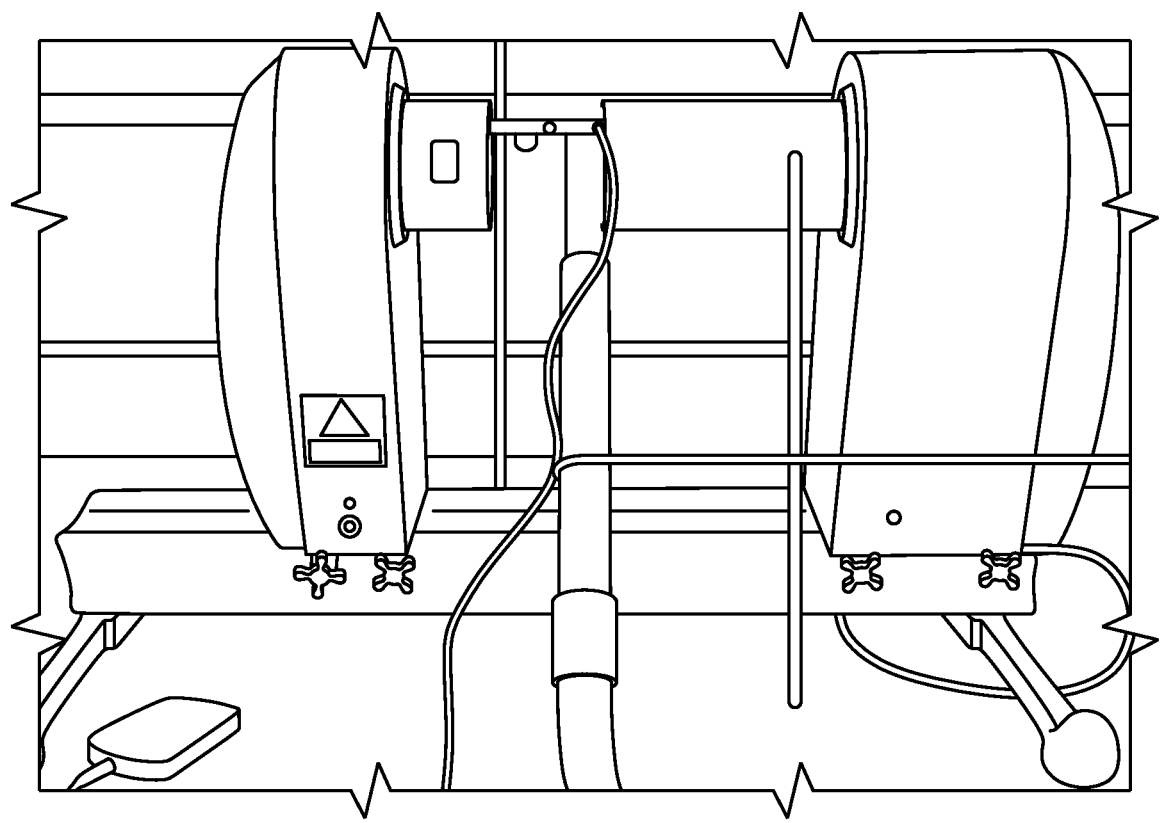
FIG. 9C shows a schematic diagram of the "open bench" method discussed in connection with the Examples below (distances: between membrane and upper edge of laser beam: 25 mm; between lens and center of aerosol cloud: 25 mm; air suction beneath laser beam: 10 cm).

Prior to setting up the Malvern Spraytec® with the "open bench" method, numerous attempts were made to perform tests using the Malvern-provide inhalation cell accessory (FIG. 9). In this system, a laser beam is projected from the left side of the instrument towards a detector positioned at the right side. The laser beam crosses the inhalation cell coupled to the Spraytec®. A nebulizer is positioned in front of the inhalation cell and a vacuum line is connected at the back of the cell. An air sheath provide by tubes in the middle of the cell helps direct aerosol droplets from the nebulizer towards the vacuum source. To evaluate nebulizer output, this setup was arranged with the inhalation cell in the horizontal position (90° angle) to measure aerosol generation as close as possible to the vibrating-mesh. The suction airflow rate was set to 30 L/min and the sheath airflow rate was set to 15 L/min (30–15 L/min=15 L/min) to obtain a final airflow rate of 15 L/min. This airflow rate was selected to match that required to analyze nebulizer formulations in the Next Generation Impactor (NGI) for comparison reasons.

An experimental artifact due to an inefficient air sheath in the Malvern Spraytec® was observed, causing the aerosol cloud to invade the detector lens compartment, causing continuously increasing obscuration and consequently reducing transmission. During operation of the inhalation cell a 0.45 μm HEPA membrane filter was positioned in-line with the vacuum source, to avoid damage to the vacuum source and to prevent exposure to the operator. However, the formulation gradually clogged the filter pores, which created back pressure that overcomes the air sheath and directs the droplets towards the detection lens chamber. After the inhalation cell windows fog, transmission values do not return to 100% and inaccurate data provides the appearance of uninterrupted nebulizer operation. Therefore, a feasible measurement using this setup was not possible. Without wishing to be bound by any particular theory, it is believed that this was due to the fact that the amount of aerosol produced during each 15-minutes nebulization event was enormous compared to pMDI and DPI devices, which the inhalation cell was primarily designed for. Therefore, while such known accessories are useful in characterizing aerosol generation from those other devices, they were not useful for continuous nebulizers according to the present invention.

Figure 10:
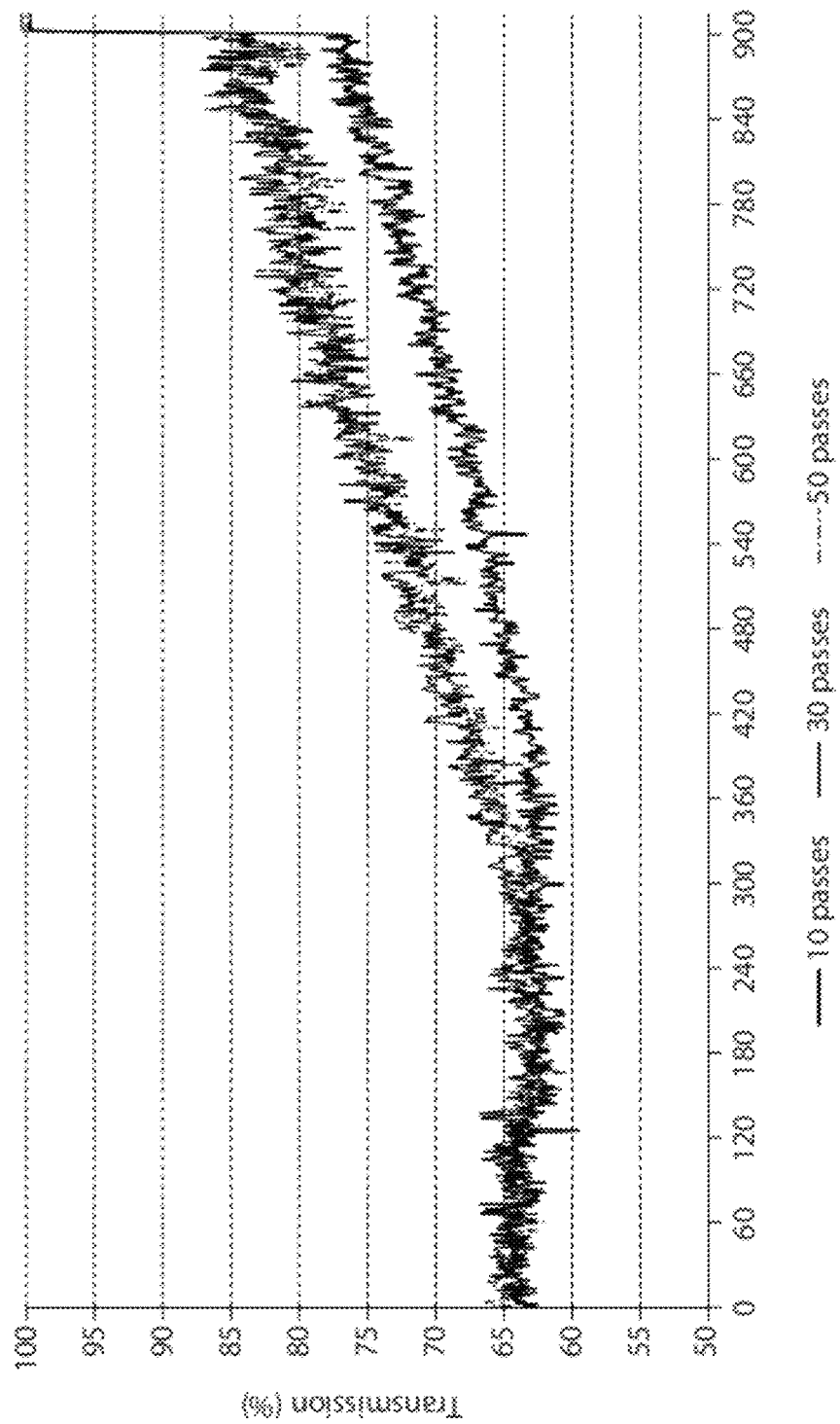
FIG. 10 shows transmittograms of lecithin dispersions of CoQ10 (Formulation C, Table 1). Results are expressed as means (n=3) of percentage transmission relative to nebulization of CoQ10 dispersions for 15 minutes. The slope values from the linear regression analysis of the curves are evaluated as measurement of steadiness in aerosol production.

To overcome this artifact, an "open bench" method was developed. The position of the nebulizer reservoir was selected to avoid vignetting (wide angle scattered light misses the detector field) while also avoiding recirculating droplets by positioning the air suction source properly for a continuous exhaustion of the generated droplets. The transmittograms presented in FIG. 10 show a nebulization event of 15 minutes for Formulation C (Table 1). At the end of this duration the transmission values go back up to 100% for all formulations, indicating that the measurement was properly performed with no fogging of the detector lens. The three formulations presented a steady nebulization for the initial 5 minutes. After this time point, the transmission related to the formulation of the 10 pass runs were increased at a different rate than formulations of the 30 and 50 pass runs. To evaluate the nebulization performance of these formulations, the transmittogram was fitted to a linear regression in order to analyze the slopes of the rate curves. By comparing their slopes, the stability of nebulization can be determined.

Figure 11:
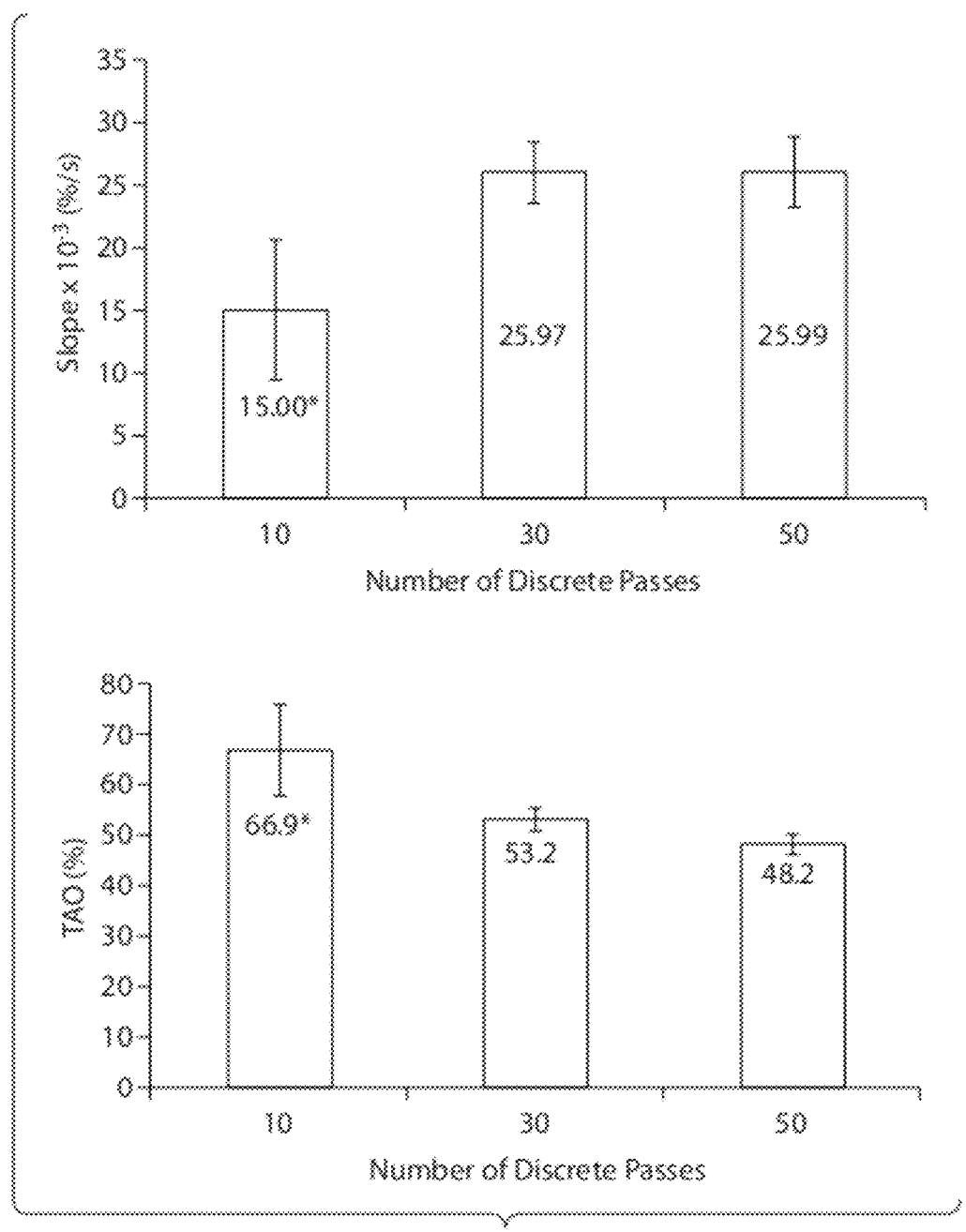
FIG. 11 shows the slope of transmittograms (top) and Total Aerosol Output (TAO—bottom) for nebulization of lecithin dispersions of CoQ10 (Formulation C, Table 1) during 15 minute nebulization events. (*$P<0.05$ compared to other formulations).

The slope values and TAO of Formulation C (Table 1) with different numbers of passes in the microfluidizer are presented in FIG. 11. A lower slope value for formulations that were run at 10 passes was observed, as compared to 30 and 50 passes. This observation agrees with the relative TAO values. These data indicate that Formulation C (processed with 10 passes in the microfluidizer) presented steadier nebulization over time than the same formulations prepared with increased processing.

Figure 12:
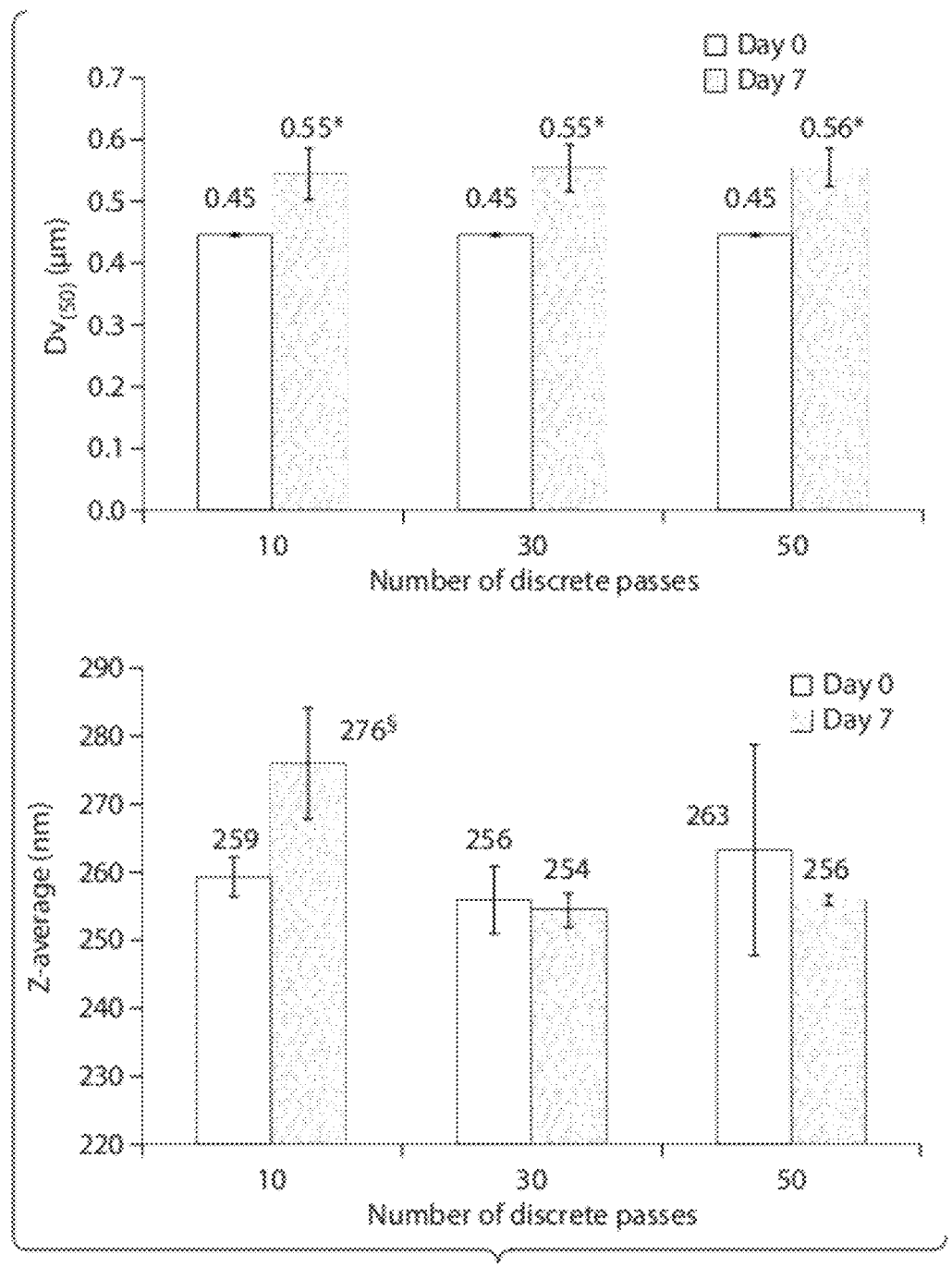
FIG. 12 shows a particle size distributions analyses of aqueous dispersions of CoQ10 (Formulation C, Table 1) following preparation in the microfluidizer using laser diffraction (left) and dynamic light scattering (right). (*$P<0.05$ compared to formulations analysed following preparation; § $P<0.05$ compared to other formulations at day 7).

Next, the physicochemical properties of Formulation C prepared with 10, 30 and 50 passes were studied to identify how processing influences nebulization performance. By analyzing hydrodynamic size in the dispersions (FIG. 12), it was we observed from LD results that the particle size appeared to be increasing slightly over time with most particles remaining in the nanometer range. When comparing formulations analyzed at day 0 for LD and DLS, we conclude that LD is not a suitable technique for the same reasons described above, based on the Fraunhofer theory. The DLS results show that all formulations presented a Z-average of approximately 260 nm. After 7 days, Dv(50) is still below range of measurement for LD technique whereas Z-average did not vary significantly for the 30 and 50 passes. From the particle size distribution results we can conclude that the formulations with the higher number of passes were stable for about 1 week. PdI was between 0.2 and 0.3 following preparation and showed some level of polydispersity after 7 days.

The results indicate that a greater hydrodynamic diameter was formed for these lecithin dispersions (approximately 260 nm) than was formed with the previous formulation analyzed (Formulation B: 120-170 nm). These differences can be explained, at least in part, by the difference in electrolyte concentrations of the formulations. Addition of 0.9% w/v of sodium chloride to Formulation C serves two purposes: to provide normal physiological osmolarity and to reduce variability in aerosol generation from this active vibrating-mesh nebulizer. Solutions with such low ionic concentrations, have a reduced variability factor, increased aerosol output, and smaller droplet sizes. Without wishing to be bound by any particular theory, low electrolyte content is believed to help to overcome drop detachment resistance from the vibrating-mesh due to an improved electrical conductivity that suppresses the high electrostatic charge of water, which in turn favors aerosol generation.

However, the addition of sodium chloride can also cause colloid instability, according to the Derjaguin-Landau-Verwey-Overbeek (DLVO) theory of interactions of electrolytes on phospholipid surfaces. In this case, a nonspecific adsorption based solely on electrostatic forces (no chemical interactions) can be caused by monovalent cations (e.g., Na+). A decrease in zeta potential caused by such cations can increase the flocculation rate (e.g., as analyzed by turbidimetry). The addition of the aforementioned salt following microfluidization was observed to change the dispersion color from dark orange to bright yellow. Despite extensive discussion concerning the mechanism of this colloid stability, current theories in colloid science are unable to fully explain this phenomenon. Drug particle size distribution of the aqueous dispersion alone does not appear to control nebulization performance because these dispersions had similar diameters (following preparation), but different aerosolization behavior.

Figure 13:
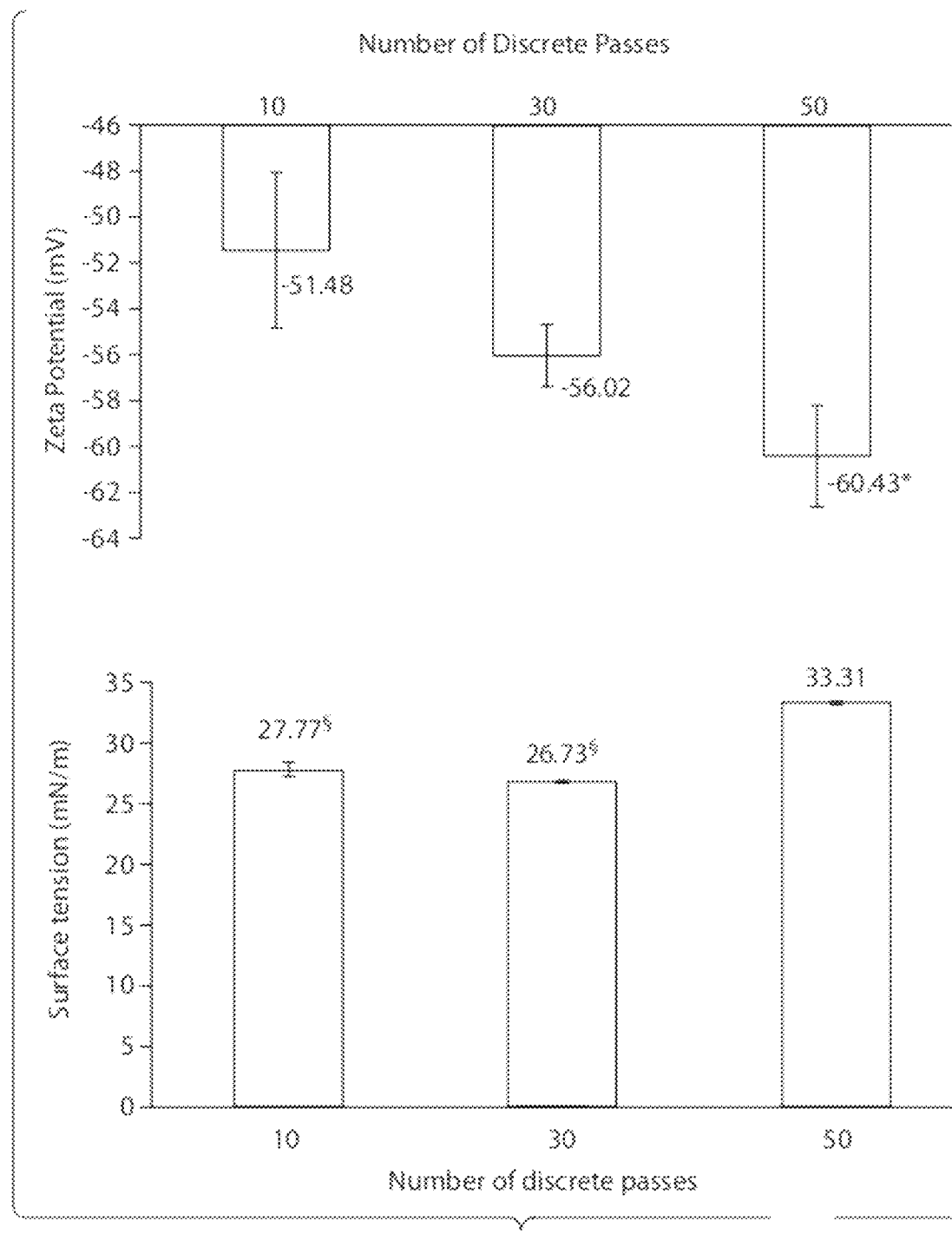
FIG. 13 shows Zeta potential and surface tension values related to formulations of CoQ10 processed at different number of microfluidization passes (Formulation C, Table 1). Columns and error bars represent means and standard errors, respectively (n=10 for zeta potential and n=5 for surface tension). The temperature during surface tension measurement was 25° C. (*P≤0.05 when compared to 10 passes, § Not statistically different).

Increasing the number of microfluidization passes increases both the surface tension and the zeta potential (statistically significant when comparing formulations processed with 10 or 50 passes, see FIG. 13). It has been hypothesized that a higher number of passes aids encapsulation. However, the role of surface tension in aerosol generation from active vibrating-mesh nebulizers is not well understood. The present example did not identify a correlation between the Formulation C zeta potential and surface tension that correlates the different number of microfluidizer passes and respective nebulization performance.

Figure 14A:
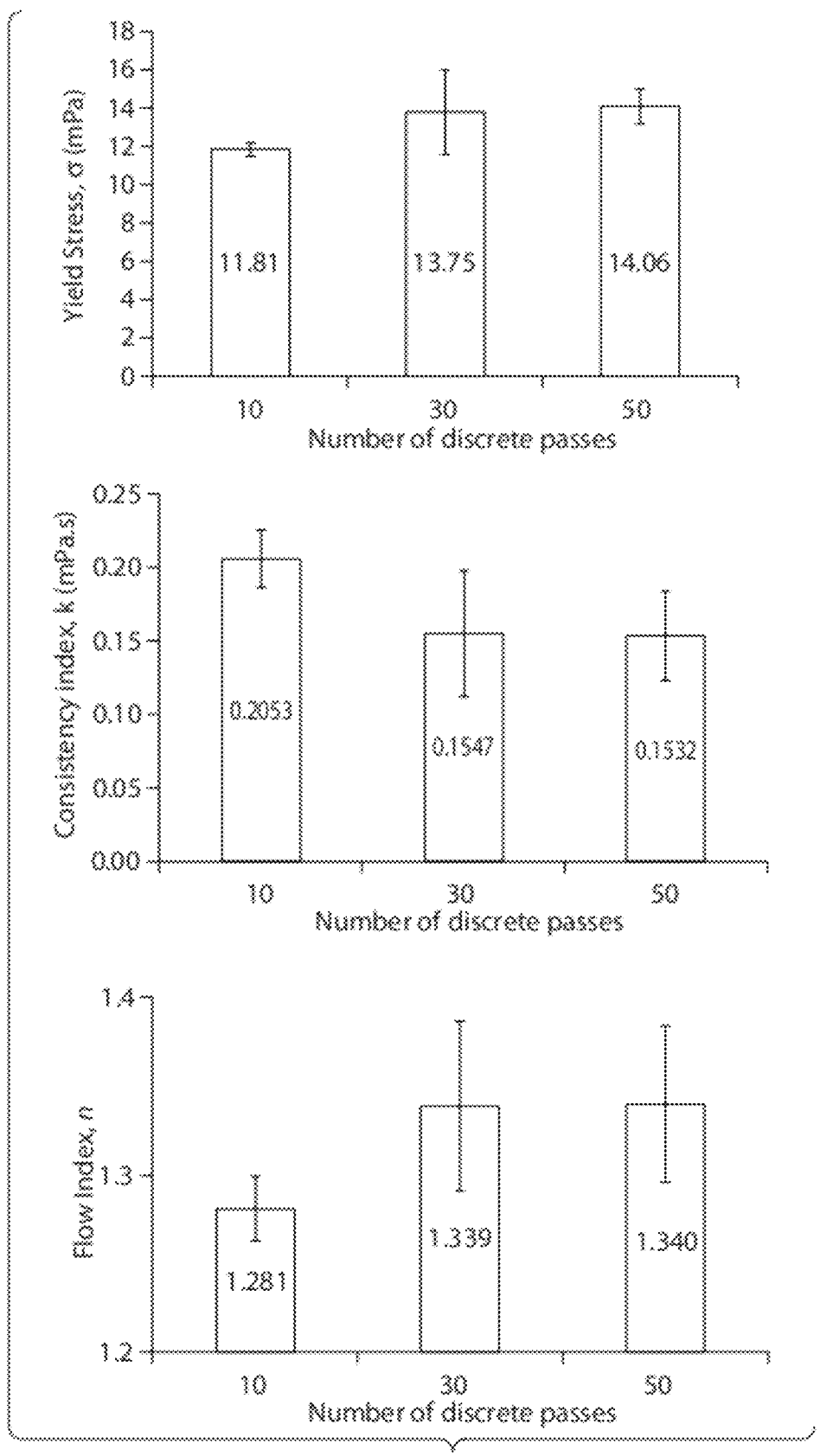
FIG. 14A and FIG. 14B shows elements of the Herschel-Bulkley model for aqueous dispersions of CoQ10 processed at different number of microfluidization passes (Formulation C, Table 1). No statistical differences were found.
Figure 14B:
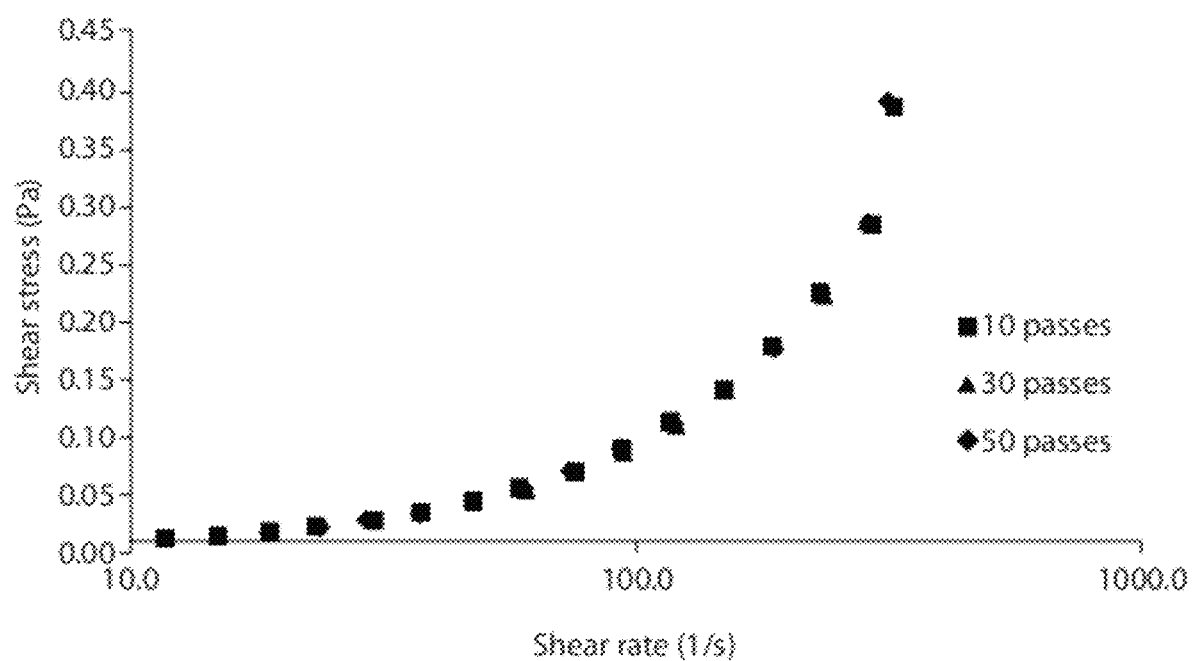

The rheology of the dispersions was studied by plotting the shear stress as a function of shear rate. The Herschel-Bulkley model, Equation 2, best represented the behavior of these three formulations:

$$\sigma = \sigma y + \kappa * \gamma'n \qquad \text{(Equation 2)}$$

Where $\sigma$ is shear stress, $\sigma y$ is yield stress, $\kappa$ is consistency index or viscosity, $\gamma$ is shear rate and n is flow index (n=1: Newtonian fluid; n<1: shear-thinning; n>1: shear-thickening). Standard errors are 32.74±3.58, 31.62±2.04, 35.92±3.57 for dispersions of CoQ10 prepared with 10, 30 and 50 microfluidization passes, respectively. The three elements of the Herschel-Bulkley model are presented in FIG. 14. Although the values of each element are not statistically different by this metric, the similarity between the rheology results and the results of nebulization performance is evident. Formulations of 30 and 50 passes presented a similar rheological behavior and nebulization performance, which were different from formulations of 10 passes. Interestingly, all formulations presented shear-thickening behavior (n>1). Characteristics like size, size distribution, shape, charge, and the interactions between particles and the surrounding fluid play significant roles in the rheological behavior of these systems. Therefore, it is not surprising that the rheological behavior of the formulations influence nebulization performance, which is a function of the interaction of all the physicochemical characteristics.

The invention provide the first known study investigating the capability of vibrating-mesh nebulizers to steadily nebulize dispersions in which fluid rheology is analyzed as opposed to performing simpler kinematic viscosity measurements (e.g., the viscosity of the dispersion media per se, without considering the interactions between the dispersed particles with the surrounding fluid).

Example 2

Prediction of In Vitro Aerosolization Profiles Based on Rheological Behaviors of Aqueous Dispersions of CoQ10

Aerosolization of dispersed formulations can generate droplets containing variable drug concentration due to the heterogeneous nature of the dosage form. Therefore, it can be important to characterize formulations for in vitro drug deposition, which can be performed with cascade impactors. Laser diffractometry (LD) can also be used for this purpose, but LD's usefulness is generally limited to solution dosage forms. The nonhomogeneity of dispersions create droplets with heterogeneous concentrations of drug particles, rendering LD unsuitable. The United States Pharmacopoeia (USP) recommends the Next Generation Impactor (NGI) be used for this testing.

Human alveolar surfactant includes about 90% phospholipids and 10% neutral lipids. Among the phospholipids, phosphatidylcholine (PC) is predominant (76%), with DPPC being the main component (81% of PC) and dimyristoyl phosphatidylcholine (DMPC) and distearoyl phosphatidylcholine (DSPC) each comprising 3% of PCs. DPPC and DSPC are also present in the mixture of phospholipids that comprise the excipient soybean lecithin, but their concentration varies widely depending on the lecithin source and extraction method.

The present example provides methods and data for selecting phospholipids formulations in accordance with the invention. The present example also provides, more particularly, methods and data for using synthetic phospholipids to prepare formulations of CoQ10 having improved nebulization performance, and which have the potential to deliver a desirable Fine Particle Dose (FPD) of CoQ10. The example studied three synthetic phospholipids: DMPC, DPPC, and DSPC, which have 14, 16 and 18 carbons in their saturated fatty acid chains and molecular weights of 678, 734, and 790 g/mol, respectively.

In addition to the tests described in connection with Example 1, the synthetic phospholipid formulations were further characterized for in vitro drug deposition using NGI and Total Emitted Dose (TED) using both NGI and a Dose Uniformity Sampling Apparatus (DUSA) for Dry Powder Inhalers (DPIs) adapted for nebulizers. The results were analyzed in conjunction with the nebulization performance tests for continuous aerosolization and for identifying the physicochemical properties governing the mechanism of aerosol generation of dispersed systems of CoQ10 from the micropump nebulizer. The results of Example 1 were also further validated by demonstrating that the rheology of the dispersions plays a role in the hydrodynamics of aerosol production using active vibrating-mesh nebulizer.

Materials and Methods

Materials:

CoQ10 was supplied by Asahi Kasei Corp. (Tokyo, Japan). Lecithin (granular, NF) was purchased from Spectrum Chemical Mfg. Corp. (Gardena, Calif., USA). Genzyme Pharmaceuticals (Liestal, Switzerland) provided 1,2-dimyristoyl-sn-glycero-3phosphocholine (DMPC), 1,2-dipalmitoyl-sn-glycero-3-phosphocholine (DPPC), and 1,2-distearoyl-sn-glycero-3-phosphocholine (DSPC). DMPC was also purchased from Lipoid GmbH (Ludswighafen, Germany). Sodium chloride (crystalline, certified ACS) was acquired from Fisher Chemical (Fisher Scientific, Fair lawn, NJ, USA) and the deionized water was obtained from a central reverse osmosis/demineralizer system. Hexane and ethanol 200 proof were purchased from Sigma-Aldrich (St. Louis, Mo., USA) and methanol from Fisher Chemical (Fisher Scientific, Fair lawn, NJ, USA), all of which were from HPLC grade. The external filter for NGI testing (glass fiber, GC50, 75 mm) and the filter for DUSA (glass fiber, AP40, 47 mm) testing were purchased from Advantec MFS Inc. (Dublin, Calif., USA) and from Millipore (Billerica, Mass., USA), respectively. Syringes (1 mL) and syringe filters (hyperclean, 17 mm, 0.45 µm, PTFE) were obtained from Becton Dickinson (Franklin Lakes, N.J., USA) and Thermo Scientific (Bellefonte, Pa., USA), respectively.

Formulation:

Formulations (100 mL) were prepared using hot high pressure homogenization to determine the effect of the type of phospholipid on the aerosolization profile—nebulization performance and in vitro drug deposition of particles for pulmonary delivery. 2.5% w/w was selected as the maximum phospholipid concentration. During preliminary studies (see Example 5), it was found that the maximum nominal drug loading that could be achieved for CoQ10 with formulations not presenting intermittent mist within a 15-minute nebulization event using the Aeroneb Pro® nebulizer was 4% w/w. Therefore, formulations with synthetic phospholipids were prepared at a drug-to-lipid ratio of 4:2.5.

Following overnight hydration while stirring, a phospholipid dispersion containing 2.5% w/w of phospholipid (DMPC, DPPC, or DSPC) in water was added to the molten CoQ10 (4% w/w) at 55° C. The formulation was then predispersed using high shear mixing with an Ultra-Turrax® TP 18/10 Homogenizer with 8 mm rotor blade (IKA-Werke GmbH, Staufen, Germany) for 5 minutes at 20,000 rpm. Subsequently, each formulation was passed 50 times through an M-110P Bench-top Microfluidizer® (Microfluidics, Newton, Mass., USA) at approximately 30,000 psi while maintaining a temperature between 55 and 65° C. Following microfluidization, 0.9% w/v of sodium chloride was added to the final formulation for reasons outlined in the previous example.

The particle size distributions of the formulations were then analyzed using Laser Diffraction (LD) and/or Dynamic Light Scattering (DLS). The surface tension, zeta potential and rheology were also evaluated. For nebulization performance, aerosol output generated from an Aeroneb Pro® nebulizer (Aerogen, Galway, Ireland) was analyzed using LD and gravimetrical analysis. In vitro drug deposition was evaluated using a NGI while the TED was analyzed from both the NGI results and from measurement using a Dose Uniformity Sampling Apparatus (DUSA). In addition to the characterization and nebulization performance presented in Example 1, the in vitro drug deposition of lecithin dispersion of CoQ10 (drug-to-lipid ratio: 1:1) passed 50 times through the Microfluidizer® was prepared and analyzed. This was evaluated against the synthetic phospholipid formulations (DMPC, DPPC, or DSPC dispersions of CoQ10). Details of the preparation, characterization and evaluation of nebulization performance of the lecithin dispersion are presented in Example 1. Testing was performed immediately following preparation, except for stability of drug particle size in the dispersions in which the samples were tested 7 days after preparation.

Characterization

Particle Size Distribution:

Particle size distribution testing of the dispersed formulations was performed with LD using a wet sample dispersion unit stirring at 1,000 rpm coupled to a Malvern Spraytec® (Malvern Instruments, Worcestershire, UK) equipped with a 300 mm lens. The dispersed formulations were added to distilled water (dispersant) until approximately 5% obscuration was attained. The internal phase and dispersant refractive indexes were 1.45 and 1.33, respectively. A timed measurement was performed for 45 seconds with 1 second sampling periods (a total of 45 data acquisition periods). Results are presented as Dv(X) and span, where X is the cumulative percentile of particles under the referred size (e.g. Dv(50) corresponds to the median volume of the particles). Span is the measurement of particle size distribution calculated as [Dv(90)–Dv(10)]/Dv(50)]. A higher span indicates a more polydisperse particle size distribution.

The nanoparticle hydrodynamic diameter of the dispersed formulations was also characterized with DLS using a Malvern Zetasizer Nano ZS® (Malvern Instruments, Worcestershire, UK) at 25° C. and pre-equilibrated for 2 minutes. The intercept of the correlation function was between 0.5 and 1.0. Distilled water was used for dilution of the dispersions where needed.

Surface Tension:

Surface tension testing was performed using a TA.XT.plus Texture Analyzer (Texture Technologies, Scarsdale, N.Y., USA). The container and glass disk probe were thoroughly degreased, cleaned with ethanol and allowed to dry. The probe was attached to the texture analyzer arm, and lowered until the bottom surface of the probe contacted the surface of the liquid formulation contained in the reservoir. The temperature of the liquid was measured and recorded. At the start of testing, the probe was raised from the surface of the liquid at a constant speed (0.05 mm/s) for 10 mm, while the texture analyzer registered at 5 points per second the force exerted as a function of either time or distance. Using the maximum (detachment) force the surface tension was calculated using Equation 3 below:

$$X/k=0.0408687+6.20312*(X^2/V)-0.0240752*(X^2/V)^2 \quad \text{(Equation 3)}$$

Where X is probe radius, V is volume and k is the meniscus coefficient. The density values used to calculate surface tension were assumed to be the same as the density of water at the measurement temperature.

Zeta Potential:

Electrophoretic light scattering was used to perform zeta potential testing with a Malvern Zetasizer Nano ZS® (Malvern Instruments, Worcestershire, UK). The samples were analyzed at a constant temperature of 25° C. and constant (neutral) pH. Samples were diluted with distilled water, obtaining conductivity values ranging from 400 to 1400 μS/cm. Each sample was analyzed in triplicate and subjected to 10 to 100 runs each measurement, with automatic optimization of attenuation and voltage selection.

Rheology:

Rheological behavior of the dispersed formulations were tested using a AR-G2 rheometer (TA Instruments, New Castle, Del., USA) equipped with a cone-and-plate geometry (cone diameter: 40 mm; truncation: 54 μm). Zero-gap and rotational mapping were performed prior to testing. All measurements were executed with fresh sample dispersion at a constant temperature of 25° C. with no pre-shear. Excess sample around the edge of the probe was trimmed and water was added to the solvent trap compartment. The samples were measured at the steady state flow step over a range of shear rates (from 1000 to as low as 0.01 $s^{-1}$) decreasing logarithmically (5 points per decade). The lower and upper limits of shear rate were determined, respectively, by the instrument sensitivity and hydrodynamic limitations (high probe speed will cause the liquid sample to spill away from the measurement zone) for each formulation. The sample period was 20 seconds and considered in equilibrium after 2 consecutive analyses within 5% tolerance, not exceeding a maximum measurement time of 2 minutes. The results were evaluated using Rheology Advantage Data Analysis software (TA Instruments, New Castle, Del., USA).

Nebulization Performance:

The performance of vibrating-mesh nebulizers with dispersion formulations can be affected by mesh clogging, resulting in variable aerosol emission (e.g., intermittent mist). To analyze the nebulization performance of the synthetic phospholipid formulations, the changes in transmission over time were evaluated from LD technique measurements. The nebulization performance of the dispersions was evaluated using the "open bench" method with a Malvern Spraytec® (Malvern Instruments, Worcestershire, UK) equipped with 300 mm lens. The nebulizer reservoir was positioned with the vibrating mesh located 25 mm above the upper edge of the laser beam at a distance of 25 mm between the lens and the center of the aerosol cloud. Air suction was positioned 10 cm beneath the laser beam. The device and air suction apparatus positions were not disturbed throughout the entire measurement period. The internal phase and dispersant refractive indexes were 1.33 (water) and 1.00 (air), respectively. Formulation (10 mL) was added to the nebulizer reservoir. At the start of nebulization, aerosol characteristics were continuously measured every second for 15 minutes. The slope of the transmission-time curves (transmittograms) were considered when comparing the different phospholipid formulations.

In addition, the Total Aerosol Output (TAO) was gravimetrically measured for each of the formulations studied. Before aerosolization, the nebulizer was weighed after each formulation was dispensed into the reservoir. The remaining formulation in the nebulizer reservoir was re-weighed after undergoing 15 minutes of nebulization. The difference in weight before and after nebulization results in the calculated TAO. The weight of the nebulizer mouthpiece was not considered during the measurements.

Importantly, neither transmittogram nor TAO alone provide complete information regarding drug output from the nebulizer. Information is limited solely to total mass output (droplets emitted over time). In the aerosolization of these dispersions, droplets not containing drug particles (empty droplets) are potentially generated. Intermittent mist can be identified in the transmittograms while TAO elucidates the magnitude of total mass being aerosolized. Saline solution (12 mL of 0.9% w/v NaCl in water) was used as the control.

In Vitro Aerodynamic Deposition:

To evaluate in vitro aerosol deposition, within a 15-minute nebulization event, the first and last 15 seconds (herein called initial and final sections or phases) of aerosol generation were collected using NGI or DUSA for DPI (both from Copley Scientific, Nottingham, UK). This design helps in determining whether the slope in transmission, previously observed for lecithin formulations and related to TAO (Chapter 4, Section 4.3), translates into similar drug mass output.

To measure the aerodynamic properties of the formulations, the NGI was set up with airflow of 15 L/min and the drug collected from the induction port, the seven stages of the cascade impactor, the micro-orifice collector (MOC) and the external filter was analyzed using High Performance Liquid Chromatography (HPLC). The sum of the masses in each of the mentioned compartments of the NGI hardware setup provides the TED measured from the NGI. The mass deposited in each stage is also used to determine the deposition pattern and to calculate the Mass Median Aerodynamic Diameter (MMAD) as described in the General Chapter <601> of the USP. This parameter is the equivalent droplet size in which half (50%) of the droplets are smaller and the other half are larger than the specified cutoff diameter, based on the drug amount deposited in different stages of the NGI. The Geometric Standard Deviation (GSD) can be used to indicate the droplet size distribution around the MMAD. The FPD was calculated from the sum of drug mass deposited on impaction Stages 3 through 7, MOC and external filter (aerodynamic cutoff diameter below 5.39 µm).

Figure 15:
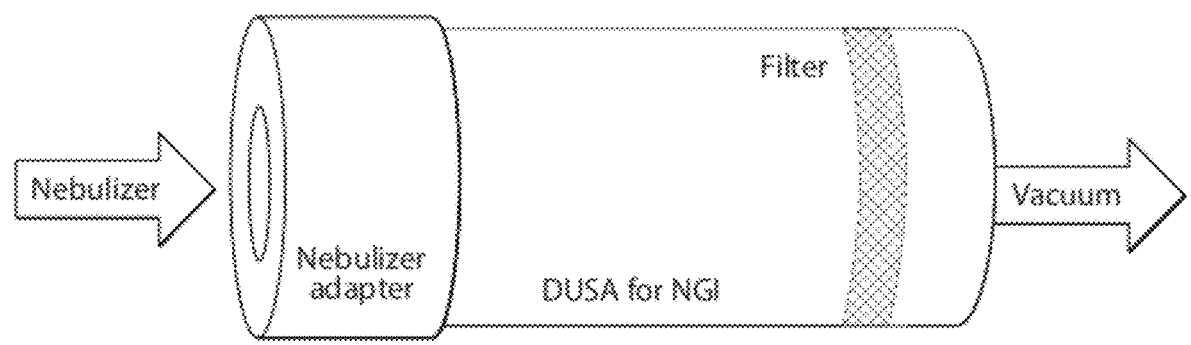
FIG. 15 shows a schematic diagram of Dose Uniformity Sampling Apparatus (DUSA) for Dry Powder Inhalers (DPIs) adapted for nebulizers.

Losses can occur during the NGI analysis drug collection due to deposition in the nebulizer mouthpiece and/or inner compartments between stages of the cascade impactor. Mass balance can be performed to ascertain the extent of such losses. During preliminary studies, it was observed that a 15-minute aerosol generation from dispersions prepared with synthetic phospholipids caused high amounts of formulation to accumulate in the nebulizer mouthpiece. TED was evaluated from an adapted DUSA to confirm that acceptable mass recovery was being achieved during the analysis (FIG. 15). During DUSA testing, the aerosol was deposited directly onto a glass fiber filter, positioned on one end of the DUSA, which was connected to a vacuum pump. The nebulizer mouthpiece was positioned on the opposite end, and directly connected to the DUSA using a silicone adapter. TED was determined from the drug amount collected in the glass fiber filter and from the internal walls of the DUSA, which was analyzed using HPLC generated data following a timed nebulization.

To further analyze the dose, FPD results were extrapolated from 15-second measurements to calculate an estimated total delivered drug (estimated total FPD or FPDet) within a 15-minute period in accordance with Equation 4:

$$FPD_{et} = \sum_{i=2}^{n} FPD_{i-1} + \left(\frac{FPD_N - FPD_{i-j}}{n-1}\right) \quad \text{(Equation 4)}$$

Where i is an integer number representing 15-second intervals (time duration of NGI and TED analyses). The j value is the subsequent integer number smaller than i, and n is the number of 15-second fractions within a 15-minute nebulization period (n=60). Fine Particle Dose (FPDr) was also calculated based upon FPDet.

HPLC Analysis of CoQ10:

This method was adapted from the previously developed method presented in Example 4. A Waters HPLC and column system (Waters Co., Milford, Mass., USA) connected to a UV detection utilized a 1525 binary pump, a 717 autosampler, a 2487 dual λ absorbance detector, set at 275 nm, and a Symmetry® RP-C8 column (3.9×150 mm, 5 µm) connected to Symmetry® C8 guard column (3.9×20 mm, 5 µm). A methanol:hexane mobile phase at 97:3 (v/v) and was eluted at a flow rate of 1.0 mL/min. Stock solution of CoQ10 was initially dissolved in hexane:ethanol at a ratio of 2:1 (v/v) and then diluted with the mobile phase to obtain the desired concentrations. The linearity range was determined by injecting 50 µL of samples at a controlled temperature of 40° C. Chromatogram peaks were acquired within run time of 9 minutes and the peak areas were used to determine curve linearity.

All samples were collected from NGI and DUSA testing with ethanol, with the exception of drug collection from the NGI plates (Stages 1 through 7 and MOC) for analysis of lecithin dispersions. Due to the low solubility of the formulation in ethanol, a mixture of hexane:ethanol 2:1 v/v was utilized. The samples collected in glass fiber filters (external filter in NGI and filter from DUSA) were vortexed for 30 seconds prior to filtering with 0.45 µm syringe filters. Mobile phase was used for sample dilution.

Statistical Analysis:

The data is expressed as mean±standard deviation with the exception of surface tension, which was expressed as mean±standard error. For rheology studies, standard errors were provided by the software used to analyze the best fit of the results to the rheological models. Samples were analyzed at least in triplicate and evaluated for statistical differences with One-Way ANOVA for significance when p<0.05 using NCSS/PASS software Dawson edition. Post hoc comparisons were performed to identify statistically significant differences among groups using Tukey-Kramer method. A paired t-test was performed to analyze statistical differences (p<0.05) within the same nebulization event for different formulations and to compare TED methods.

Results and Discussion

Synthetic phospholipids (DMPC, DPPC, and DSPC) were used to prepare CoQ10 formulations and compared the results with lecithin formulation analyzed in Example 1. Because CoQ10 delivery is achieved via a dispersion, aerosolization can generate droplets containing differing amounts of drug. Therefore, the aerodynamic properties of the formulation were analyzed using a cascade impactor, based on the drug amount deposited in each stage of the NGI apparatus. Furthermore, TED was analyzed based on drug collected in a filter delivered directly from the nebulizer mouthpiece. Nebulization performance combined with the aerodynamic properties of the dispersion can provide a basis for the comparison of the inhalable potential of the formulations. These characteristics also for the identification of physicochemical properties favoring effective drug emission of drug dispersions from a nebulizer.

Figure 16:
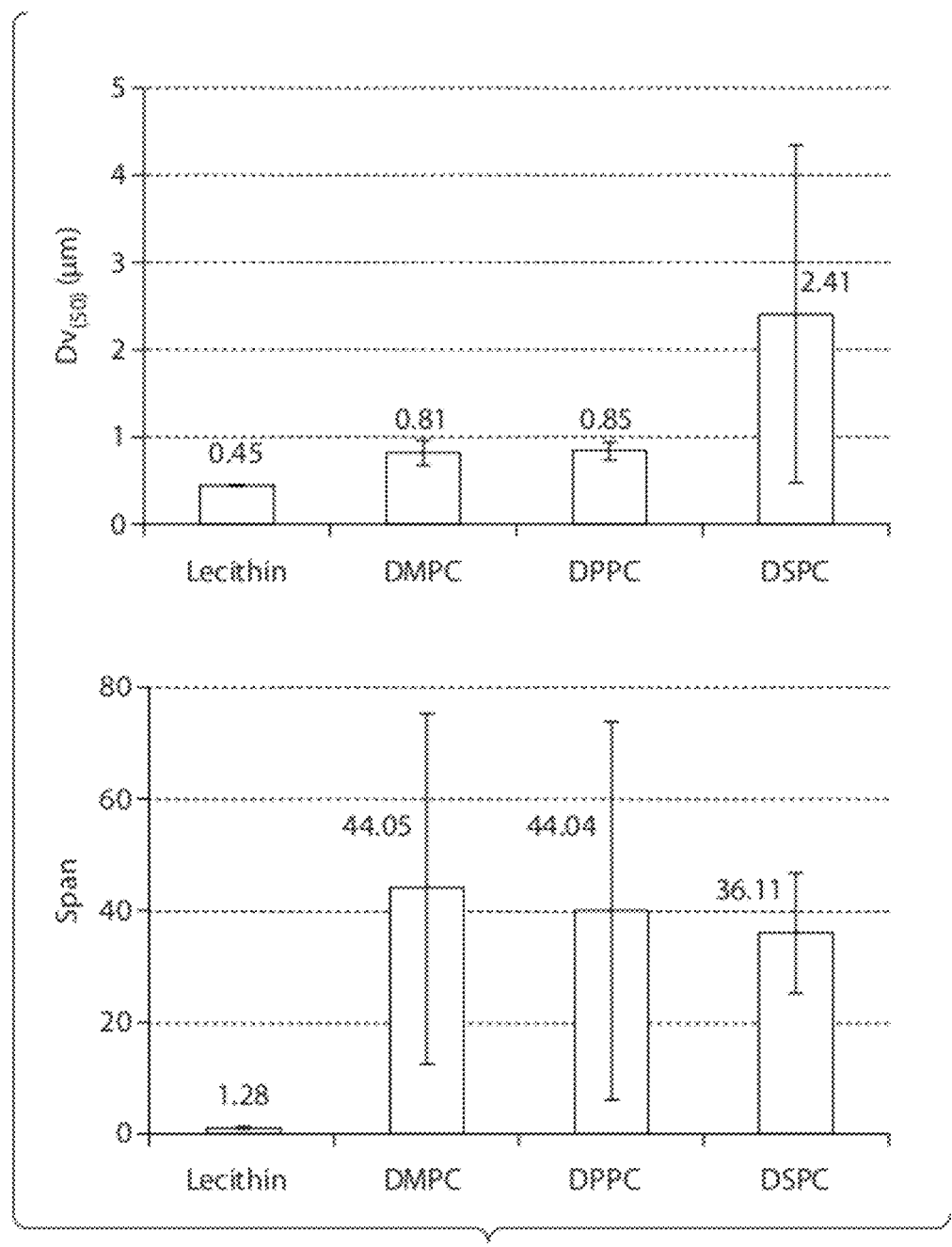
FIG. 16 shows a particle size distributions from laser diffraction technique of aqueous dispersions of CoQ10 following 50 passes in the microfluidizer. Results are expressed as means±standard deviations (n=3). Some standard deviations are too small to be visible on the graphs.
Figure 17:
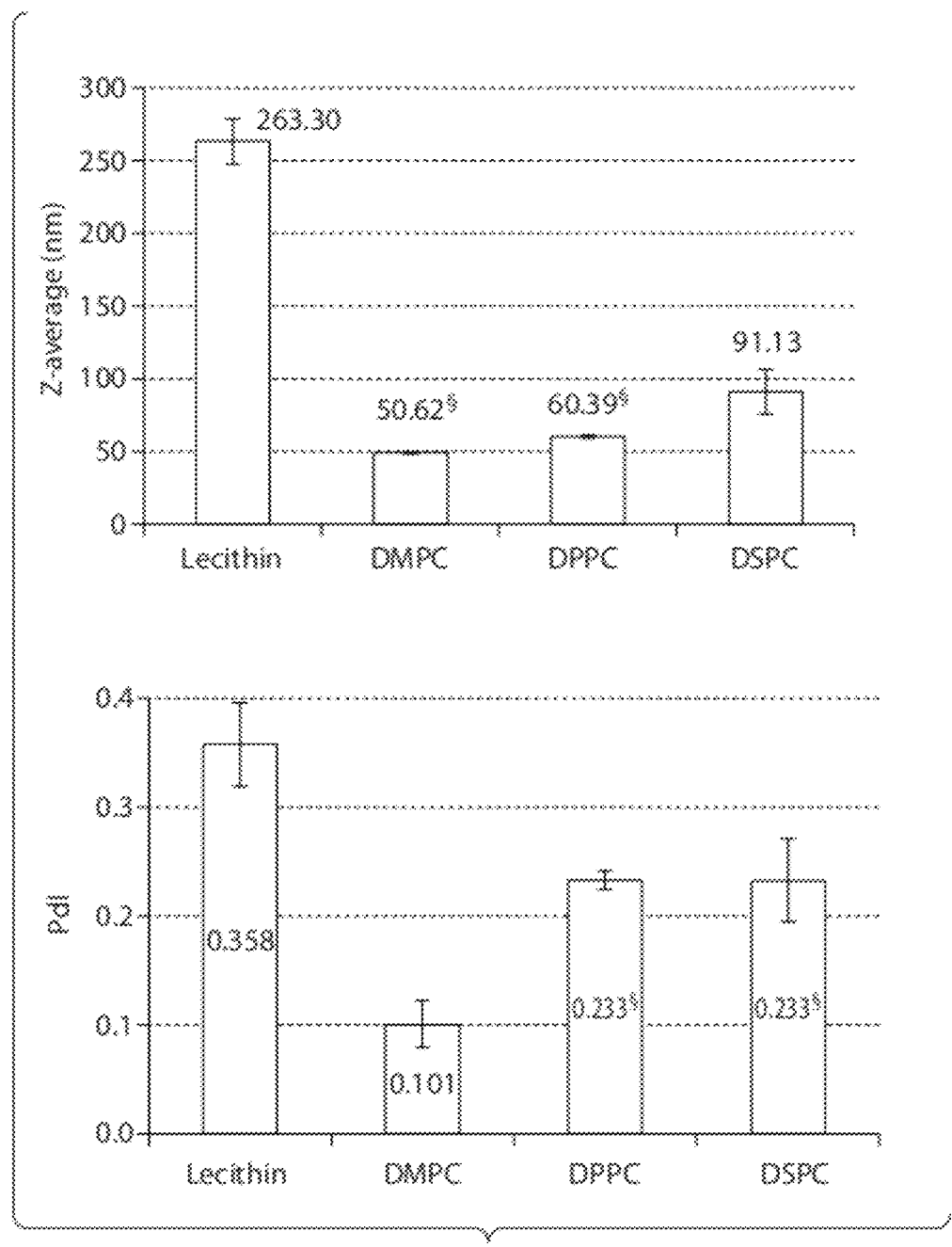
FIG. 17 shows Z-average and PdI values of aqueous dispersions of CoQ10 following 50 passes in the microfluidizer. Results are expressed as means±standard deviations (n=3). Some standard deviations are too small to be visible on the graph (n=3). § Not statistically different.

The hydrodynamic size in the dispersions (FIG. 16 and Table 3) show that the lecithin formulation drug particle size was predominantly in the submicron range. Synthetic phospholipid formulations presented some larger particles, though analysis of Dv(X) and span does not present statistical differences among formulations (excepting the Dv(10) of DMPC and DSPC dispersions). Further analysis of drug particle size distribution using DLS shows that lecithin dispersions presented larger nanoparticles with a higher polydispersity than the synthetic phospholipid formulations (FIG. 17). Among synthetic phospholipids, the DSPC dispersion presented the largest drug nanoparticles while the DMPC formulation presented the most monodisperse profile. Following processing, the synthetic phospholipids presented some microparticles, although the population of particles in the nanometric scale was primarily smaller than drug particles that were produced from lecithin dispersions of CoQ10.

Figure 18:
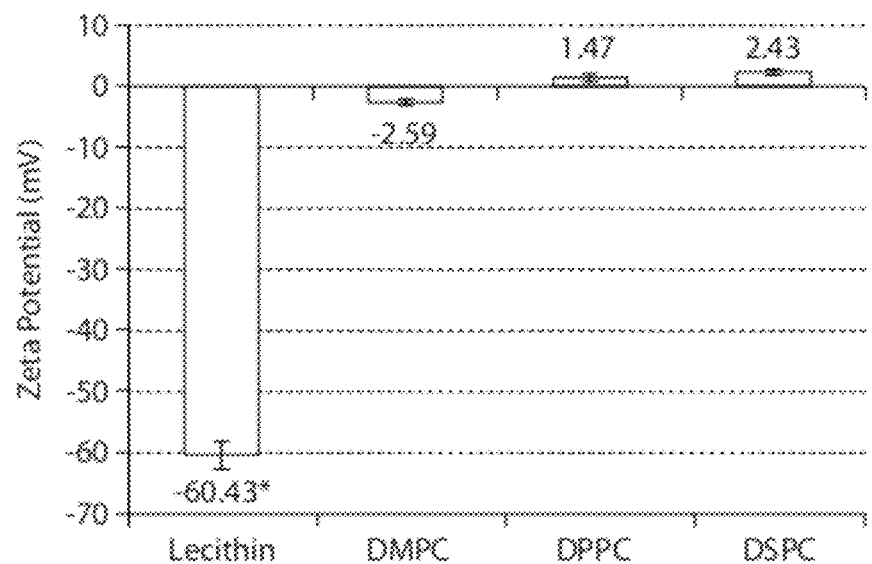
FIG. 18 shows Zeta potential of CoQ10 dispersions. Results are expressed as means±standard deviation (n=3). *P<0.05 when compared to synthetic phospholipids.

The zeta potential of lecithin dispersion was significantly higher than that of the synthetic phospholipid dispersions (FIG. 18). Without wishing to be bound by any particular theory, the mixture of different phospholipids at various concentrations depending on the source and extraction method for lecithin can lead to variable zeta potential values. The zeta potential values of synthetic phospholipids can be attributed to the presence of sodium chloride in the formulations because increases in ionic strength at neutral pH can increase the zeta potential of negatively charged phospholipids like DMPC, DPPC, and DSPC.

Figure 19:
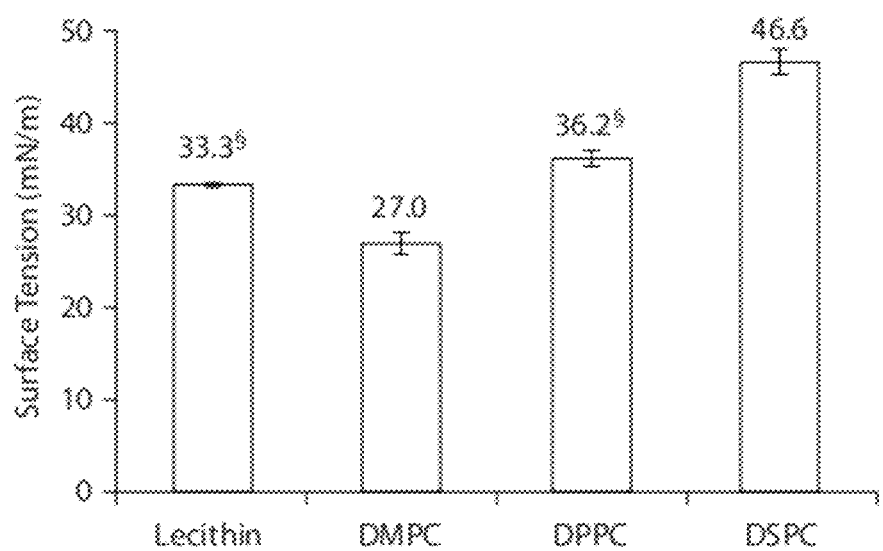
FIG. 19 shows surface tension of CoQ10 dispersions. Results are expressed as means±standard error (n≥5). The temperature values during measurement were 25° C., 25° C., 19° C. and 17° C., respectively. § Not statistically different.

Increasing the number of microfluidizer passes can cause a decrease in surface tension (e.g., possibly due to a more efficient encapsulation). For the synthetic phospholipid compositions, an increase in surface tension was observed which tracked the increase in the number of carbons in the acyl chains of the phospholipid. The formulations were designed to have the same amount of DMPC, DPPC, and DSPC at 2.5% w/w. However, the molecular weight vary slightly due to the different number of carbons in each respective acyl chain. Accordingly, the molar concentrations of the phospholipids in the dispersions were 36.9, 34.1 and 31.6 mM, respectively. The structure of phospholipids in water dispersions depended directly on the number of phospholipid molecules. Therefore, without wishing to be bound by any particular theory, it is believed that the number of phospholipid molecules available in "solution" to cause a decrease in surface tension at a constant temperature can explain the differences in surface tension. It is noteworthy that the surface tension of the CoQ10 dispersion prepared with lecithin, which is a mixture of phospholipids, falls between the values of DMPC and DSPC (FIG. 19).

Particle characteristics such as size, size distribution, shape, charge, deformability, and the interactions between particles and the surrounding fluid can play a role in the rheological behavior of dispersed systems. To evaluate the rheology of the dispersions, shear stress was plotted as a function of shear rate and the results were fit to the best rheological model. The Herschel-Bulkley model (See Equation 2 and corresponding text above) best represented most of the formulations.

The Power Law model is similar to Herschel-Bulkley, except that it does not present yield stress value. Standard errors are 35.92±3.57, 9.83±0.17, 10.27±0.35, 21.15±8.17 for lecithin, DMPC, DPPC and DSPC dispersions, respectively. The three elements of the Herschel-Bulkley model are presented in FIG. 20. DSPC dispersion of CoQ10 was governed by Power Law and therefore did not present yield stress. Interestingly, the yield stresses of the formulations are shown to be statistically different but no trend was identified. DSPC formulation had a significantly higher Non-Newtonian viscosity than the other analyzed samples, possibly due to its evident shear-thinning behavior (n<1). Interestingly, the flow index results indicated that DPPC, DMPC, and lecithin dispersions respectively presented increasing shear-thickening behavior (n>1).

Figure 21:
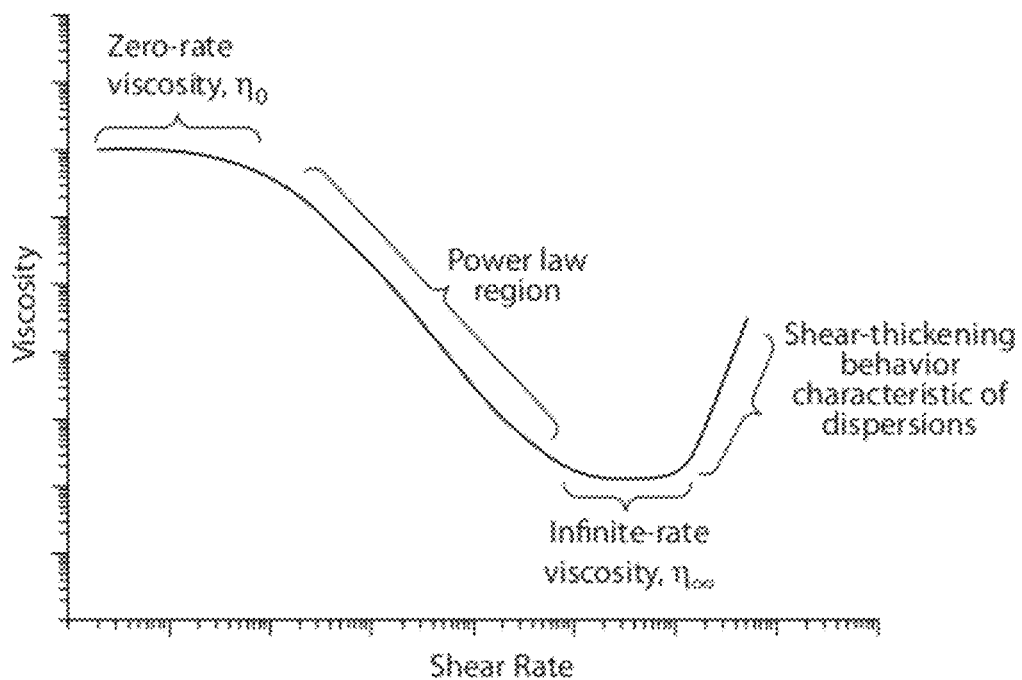
FIG. 21 shows an example schematic of a general flow curve of aqueous dispersions.

The rheology was further analyzed by holding shear rate and viscosity as the independent and dependent variables, respectively, in order to fit the results to the general flow curve of aqueous dispersions (FIG. 21). Graphical representations are presented in FIG. 22, which clearly shows the accentuated DSPC formulation shear-thinning event. Relevant equations related to these models are shown in Table 4. By fitting these curves to the rheological models, it was found that the formulations presented different behavior (Table 5). Standard errors are 93.49±8.60, 43.27±10.55, 41.34±8.57, 16.00±4.74 for lecithin, DMPC, DPPC and DSPC dispersions, respectively.

Figure 20:
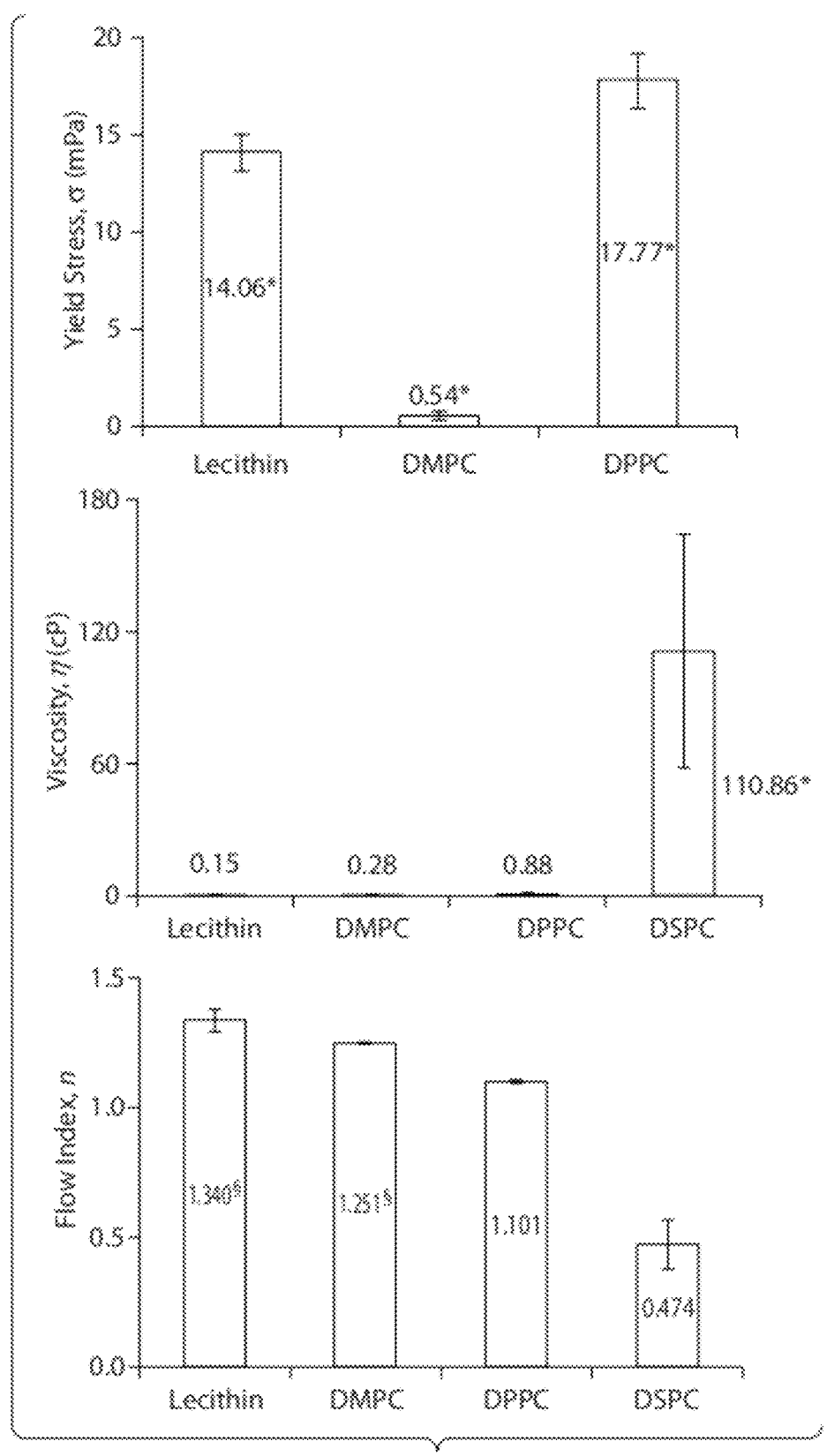
FIG. 20 shows elements of the Herschel-Bulkley model for aqueous dispersions of CoQ10, expressed as means±standard deviations (n=3). Yield stress of DSPC formulation is not presented because it follows Power Law model. Some standard deviations are too small to be visible on the graph. *P<0.05. § Not statistically different.

The lecithin formulation of CoQ10 fits to the Sisko model, indicating that the investigated shear rate range falls within the mid-to-high shear-rate range related to the general flow curve of dispersions. This is confirmed by the small characteristic time seen in Table 5 and the curve shape at higher shear rates shown in FIG. 22. This result also confirms the shear-thickening behavior presented from the evaluation of the Herschel-Bulkley model (FIG. 20). Of the formulations studied, only the lecithin dispersion presented thixotropic behavior. This indicates a time-dependent change following interruption of shear stress (e.g., shear-thinning event) during structure recovery from the shear-thickening behavior presented by this dispersion in the shear rate range studied. Therefore, the synthetic phospholipid formulations promptly recover to their initial state at cessation of shear stress.

Figure 22:
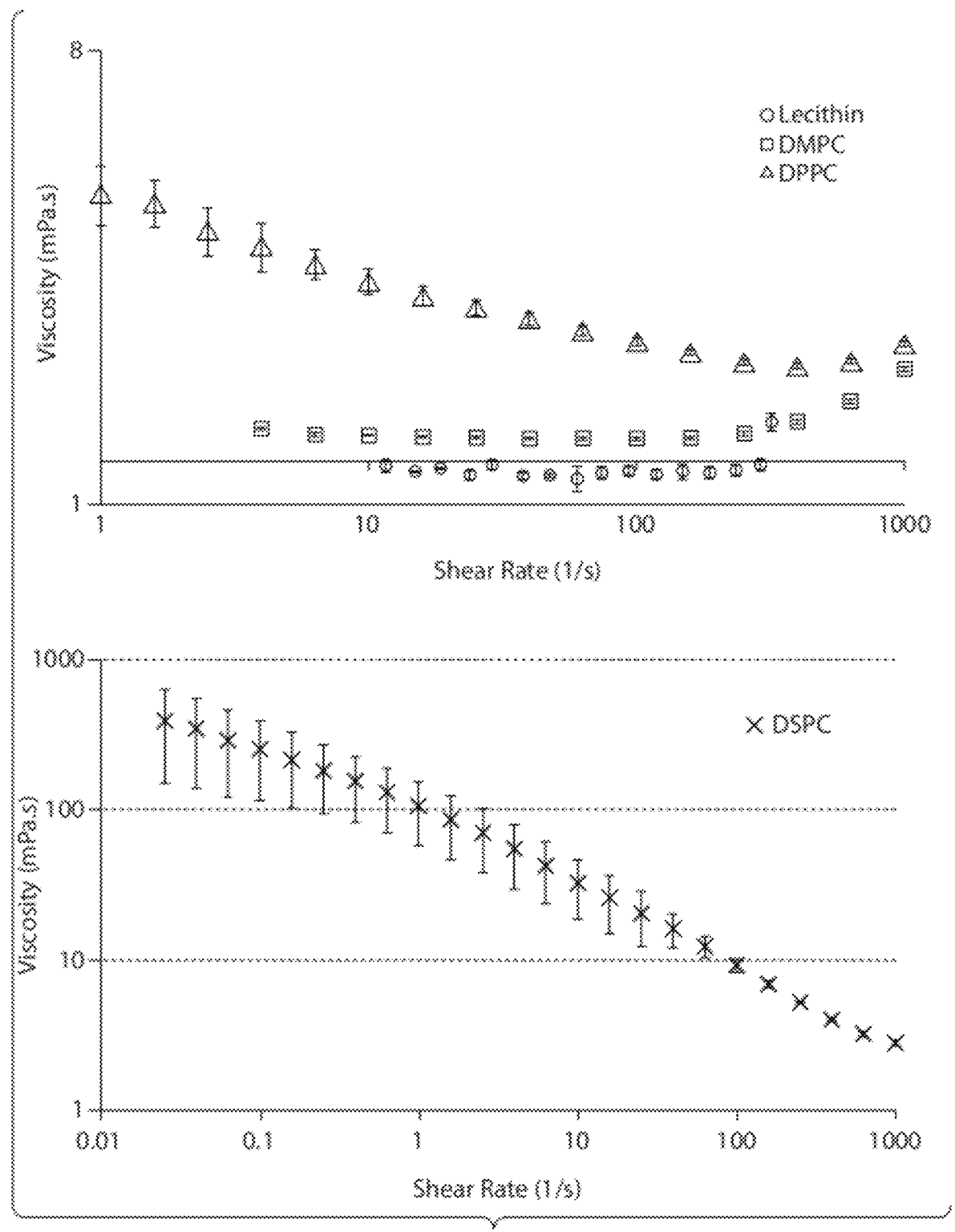
FIG. 22 shows rheological behavior of CoQ10 dispersions. Graphs presented in different scales are expressed as means±standard deviations (n=3).

The DMPC and DPPC dispersions followed the Cross model, thus both zero-rate and infinite-rate viscosities are presented. However, the formulations' characteristic times differ greatly, with the lowest value shown for the DMPC formulation. This indicates that, similarly to lecithin dispersion, the DMPC formulation falls towards the upper range of shear rate related to the general flow curve of dispersions (Table 5), explaining the second Newtonian plateau (3.66 cP) being greater than the first Newtonian zone (1.13 cP). Therefore, the rheological behavior of the DMPC dispersion is closer to the Sisko than the Cross model. For this reason, both lecithin and DMPC dispersions present rate index (or Cross rate constant) values above unity, reflecting the absence of the power law region in the shear rate range investigated. When the viscosity within this specific range is appropriately extending from the first to the second Newtonian zone, 1−m is close to the rate index n. The shear-thickening behavior is evident from the curve shape at higher shear rates (FIG. 22). The larger characteristic time of the DPPC formulation indicates that the curve falls more towards the lower range of shear rates and therefore supports the infinite-rate viscosity being smaller than the zero-rate viscosity. The Cross rate constant is close to unity, which indicates a degree of shear-thinning behavior in the power law region. Observation of the curve shape of DPPC dispersion in FIG. 22 supports these findings and the relatively low degree of shear-thickening behavior presented in the Herschel-Bulkley model (FIG. 20). This relatively low degree of shear-thickening behavior, when compared to lecithin and DMPC formulations, can be attributed to differences in rheology at higher shear rates.

The rheological behavior of the DSPC followed the Williamson model. The statistically significant higher characteristic time in conjunction with the flow curve shape of this dispersion indicate that the shear rate range investigated falls within the low-mid shear rate range of the general flow curve of dispersions (FIG. 22). The rate index value reflects the shear-thinning behavior at the power law region (Table 5).

As discussed in connection with Example 1, it can be important to investigate the capability of vibrating-mesh nebulizers to continuously and steadily aerosolize dispersions, with concomitant analysis of fluid rheology as opposed to simpler kinematic viscosity measurements. Previous works have focused on the viscosity of the dispersion media per se, regardless of the interactions between the dispersed particles within the surrounding fluid. Because high frequency mechanical stress of the nebulizer is directly transferred to the formulation, analysis of rheology parameters at higher shear rates may better translate to what is actually occurring in the vicinity of the vibrating membrane.

Some standard error values obtained from fitting the results to rheological models can be considered relatively high. Without wishing to be bound by any particular theory, it is believed that these values can be attributed to a limited shear rate range studied using the experimental design of the present examples. Although further and/or additional experiments could be conducted to lower standard error, the understanding of formulation reaction to the stress applied nevertheless provides valuable information about what can be expected from the active membrane nebulization of such dispersions.

Figure 23:
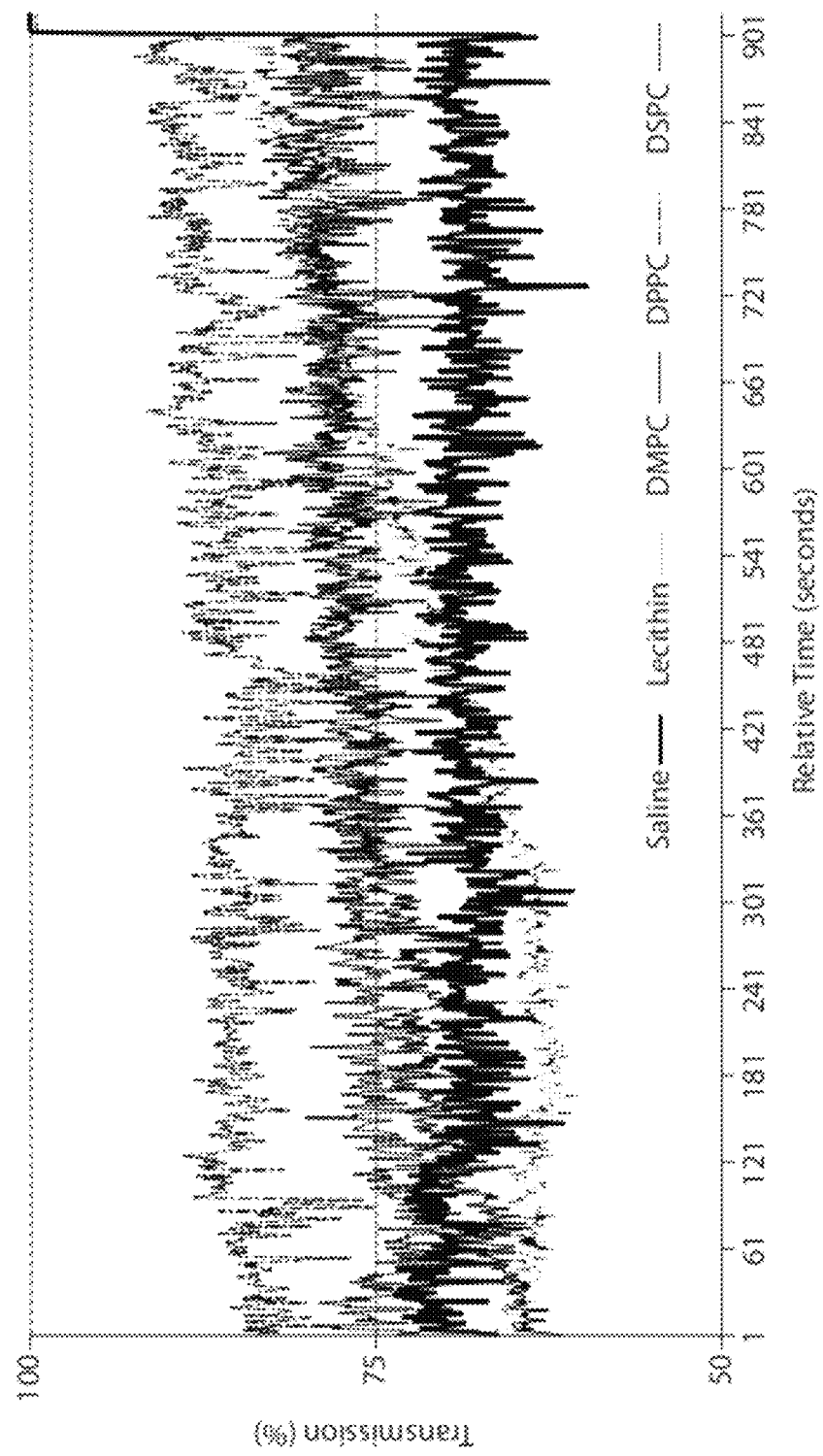
FIG. 23 shows transmittograms of saline (control) and lecithin, DMPC, DPPC and DSPC dispersions of CoQ10. Results are expressed as means (n=3) of percentage transmission relative to nebulization of CoQ10 dispersions for 15 minutes. The slope values from the linear regression analysis of the curves are evaluated as measurement of steadiness in aerosol production.
Figure 24:
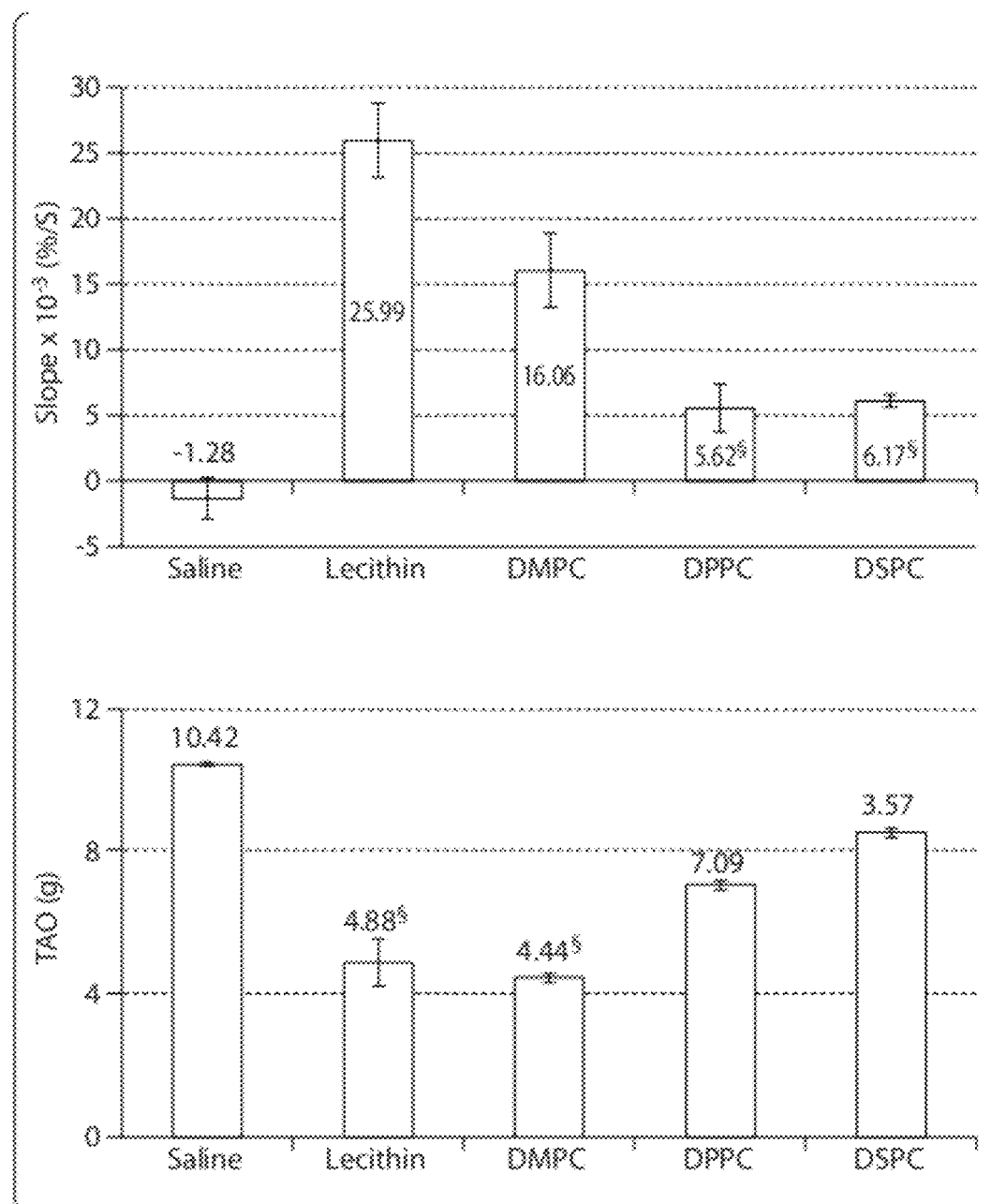
FIG. 24 shows slope of transmittograms (top) and Total Aerosol Output, TAO (bottom), expressed as means±standard deviations (n=3) relative to nebulization of CoQ10 dispersions for 15 minutes. § Not statistically different.

In order to compare the nebulization performance of the formulations, a Malvern Spraytec® was set up with the open bench method described in Example 1. The transmittograms presented in FIG. 23 show nebulization events with a 15 minute duration. At the end of this duration, the transmission values returns to 100%, indicating that the measurements were performed properly and without detector lens fogging. To evaluate the nebulization performance of these formulations, the transmittograms were fitted to a linear regression to analyze the slopes of the curves. The steadiness of a given nebulization event can be inferred from the slope. The slopes and the TAO results are presented in FIG. 24. Aerosolization of the control (i.e., saline) was steadiest over time, as indicated by the slope of essentially zero and the highest TAO. The lecithin formulation exhibited steady nebulization for the initial 5 minutes (300 seconds), followed by an increase in transmission. The DMPC dispersion exhibited a transmission profile with a pattern opposite to lecithin. At the start of nebulization, a slight slope was observed up to about 8 minutes (480 seconds), followed by steady nebulization. DPPC and DSPC dispersions presented a very shallow slope throughout nebulization.

The lecithin dispersion exhibited the highest slope and a low TAO (that was not statistically different from the DMPC formulation). Although the DPPC and DSPC formulations presented similar slopes (e.g., not statistically different), the TAO from DSPC showed a higher mass output than that the TAO from DPPC, despite both formulations being steadily nebulized. These results show the importance of analyzing the slope of the transmittograms in conjunction with the mass output (or TAO). The DSPC formulation presented the best results among the aqueous dispersions of CoQ10, exhibiting a low slope value and the highest TAO among the phospholipid dispersions. To summarize, the order of increasing nebulization performance in the studied formulations was: Lecithin<DMPC<DPPC<DSPC.

These findings can be evaluated concomitantly with the respective rheological behavior of the formulations at higher shear rates. Upon examination of the curves (FIG. 22), at high shear rates lecithin and DMPC dispersions present the characteristic shear-thickening behavior following the second Newtonian plateau, which is confirmed by their low respective characteristic times. The occurrence of shear-thickening following the shear-thinning event can be attributed to an arrangement instability following the two-dimensional layering of the fluid. Being above a critical shear stress can causes random arrangement of the dispersed particles, resulting in an increase in viscosity. The random arrangement can limit steady nebulization performance, as shown by these two formulations. On the other hand, the high characteristic times and shear-thinning behavior at the power law region presented by DSPC, and to a lesser extent DPPC, dispersions at high shear rates can explain their relatively superior nebulization performance. These results suggest that a high characteristic time corresponding to a shear-thinning behavior at high shear rates may favor the nebulization performance, while shear-thickening (low characteristic time) may have the opposite effect. Therefore, these results suggest that the rheological behavior at high shear rates can be directly related to the nebulization performance of the dispersions.

However, these data suggest that mass output may not be correlated (e.g., directly correlated) to drug emission in the case of the nebulization of the dispersions described herein. Therefore, in order to measure drug aerosolization and to gain understanding of the aerodynamic properties of the formulations, the in vitro deposition of the phospholipid formulations of CoQ10 was analyzed using NGI and adapted DUSA. Analysis of drug deposition at initial and final time fractions of the 15-minute nebulization period allowed for an evaluation of this data in conjunction with the nebulization performance.

Figure 25:
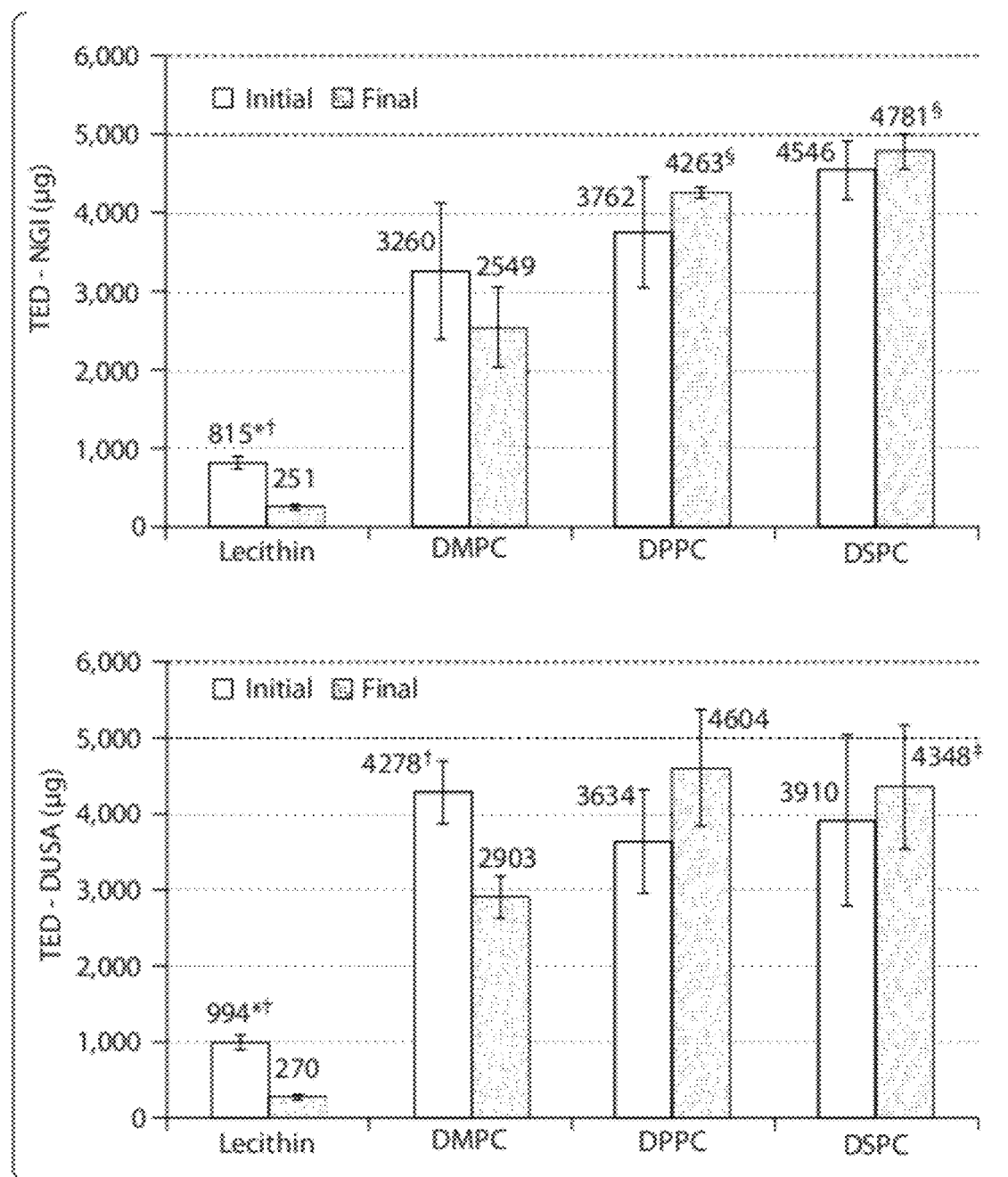
FIG. 25 shows TED from NGI (top) and from DUSA for DPI adapted for nebulizers (bottom) of dispersions of CoQ10. Results are expressed as means±standard deviations (n=3) of total drug deposited within a 15 second period at initial and final phases of a 15-minute nebulization event. TED: Total Emitted Dose; DUSA: Dose Uniformity Sampling Unit; DPI: Dry Powder Inhaler. *P<0.05 when compared to synthetic phospholipids. †P<0.05 within nebulization event. § Not statistically different compared to each other. ‡Not statistically different compared to other synthetic phospholipids.

The TED of lecithin, DMPC, DPPC and DSPC formulations are presented in FIG. 25. The lecithin dispersion of CoQ10 presented a statistically significant decrease in drug aerosolization comparing initial and final phases of nebulization period, following both NGI and DUSA analysis. This difference in amount of drug emitted at the beginning and at the end of the nebulization confirms that the slope ($25.99 \times 10^{-3} \pm 2.80 \times 10^{-3}$%/s) observed in the results from nebulization performance using LD is not only related to decreased mass output, but also to the amount of drug being aerosolized. Overall, the lecithin dispersion also presented a significantly smaller TED both at the initial and final phases when compared to the synthetic phospholipid formulations.

No statistical difference was found within the same nebulization event for the dispersions prepared with synthetic phospholipids under NGI analysis. However, the DMPC dispersion exhibited a smaller TED within the same nebulization event using the DUSA methodology. However, the TED/DUSA results can be more relevant to the present analysis because the droplets containing the drug are directly deposited in a filter whereas the TED/NGI results have potential losses associated with the NGI apparatus. Regardless of the potential losses, a satisfactory mass balance was achieved because no statistical difference was identified in comparing the two methods' determination of TED. The slope ($16.06 \times 10^{-3} \pm 2.88 \times 10^{-3}$%/s) from nebulization performance testing of DMPC dispersion is in agreement with the difference in drug amount being aerosolized within the 15-minute nebulization period. DPPC and DSPC dispersions of CoQ10 aerosolized in approximately equal. These results show that these formulations both exhibit steady nebulization (e.g., as quantified in the relatively small linear regression slope values).

Figure 26:
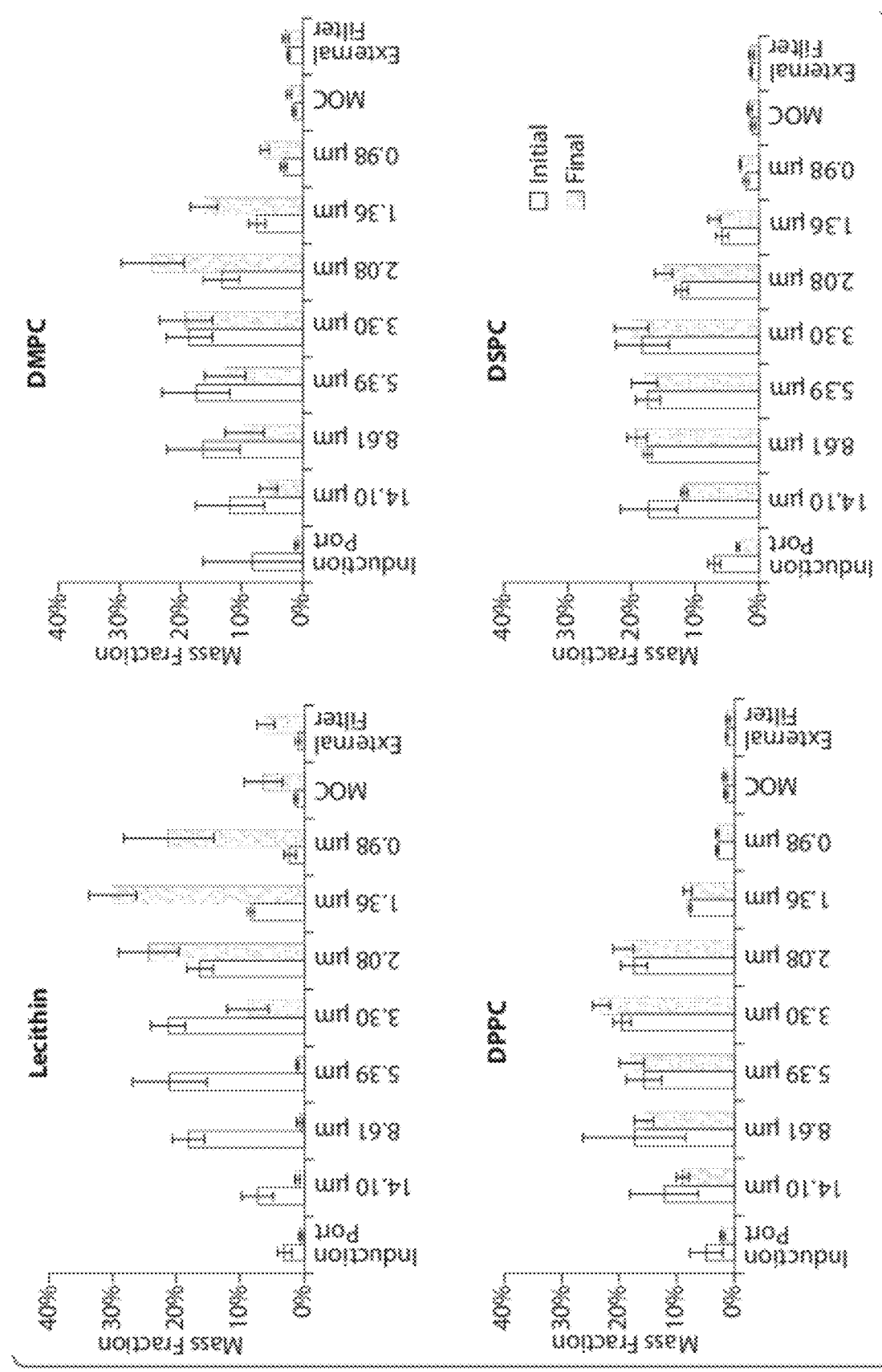
FIG. 26 shows in vitro deposition profiles of lecithin, DMPC, DPPC and DSPC dispersions of CoQ10 at a flow rate of 15 L/min using an Aeroneb Pro® nebulizer. Results are expressed as means±standard deviations (n=3) of the percentage of total drug deposited within a 15-second period at initial and final phases of a 15-minute nebulization event.
Figure 27:
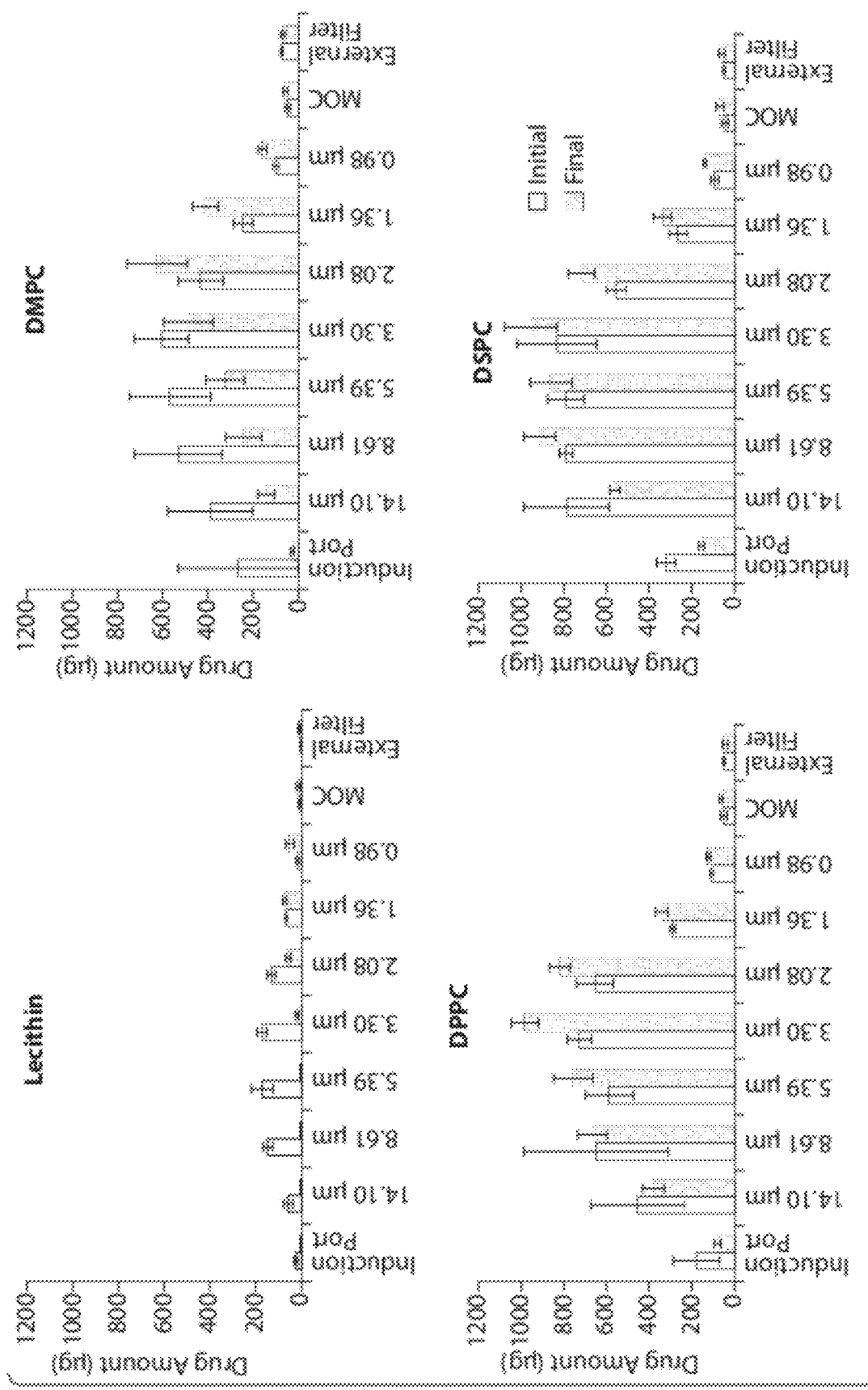
FIG. 27 shows in vitro deposition profiles of lecithin, DMPC, DPPC and DSPC dispersions of CoQ10 at a flow rate of 15 L/min using an Aeroneb Pro® nebulizer. Results are expressed as means±standard deviations (n=3) of the drug amount deposited within a 15-second period at initial and final phases of a 15-minute nebulization event.

Aerodynamic properties that can affect pulmonary drug delivery are shown in FIGS. 26 and 27. The lecithin formulation exhibited a higher droplet size, as related to drug mass fraction deposited, at the initial stage of nebulization than at the final stage (FIG. 26). The DMPC formulation, to a lesser extent, exhibited a similar pattern to the lecithin formulation. The DPPC and DSPC formulations had a more balanced droplet size throughout the 15 minute nebulization event. With respect to the drug amount deposited (as opposed to drug fraction), FIG. 27 shows that the overall deposition of lecithin formulation was low both at the initial and final phases (e.g., when compared to the other formulations). This result is in agreement with the TED results. Among the three synthetic phospholipids studied, the DMPC formulation presented the lowest deposition, which is in agreement with the TAO and TED results. The DPPC and DSPC formulations had high drug amounts deposited and maintained consistent aerodynamic properties throughout the 15 minute nebulization event.

Figure 28:
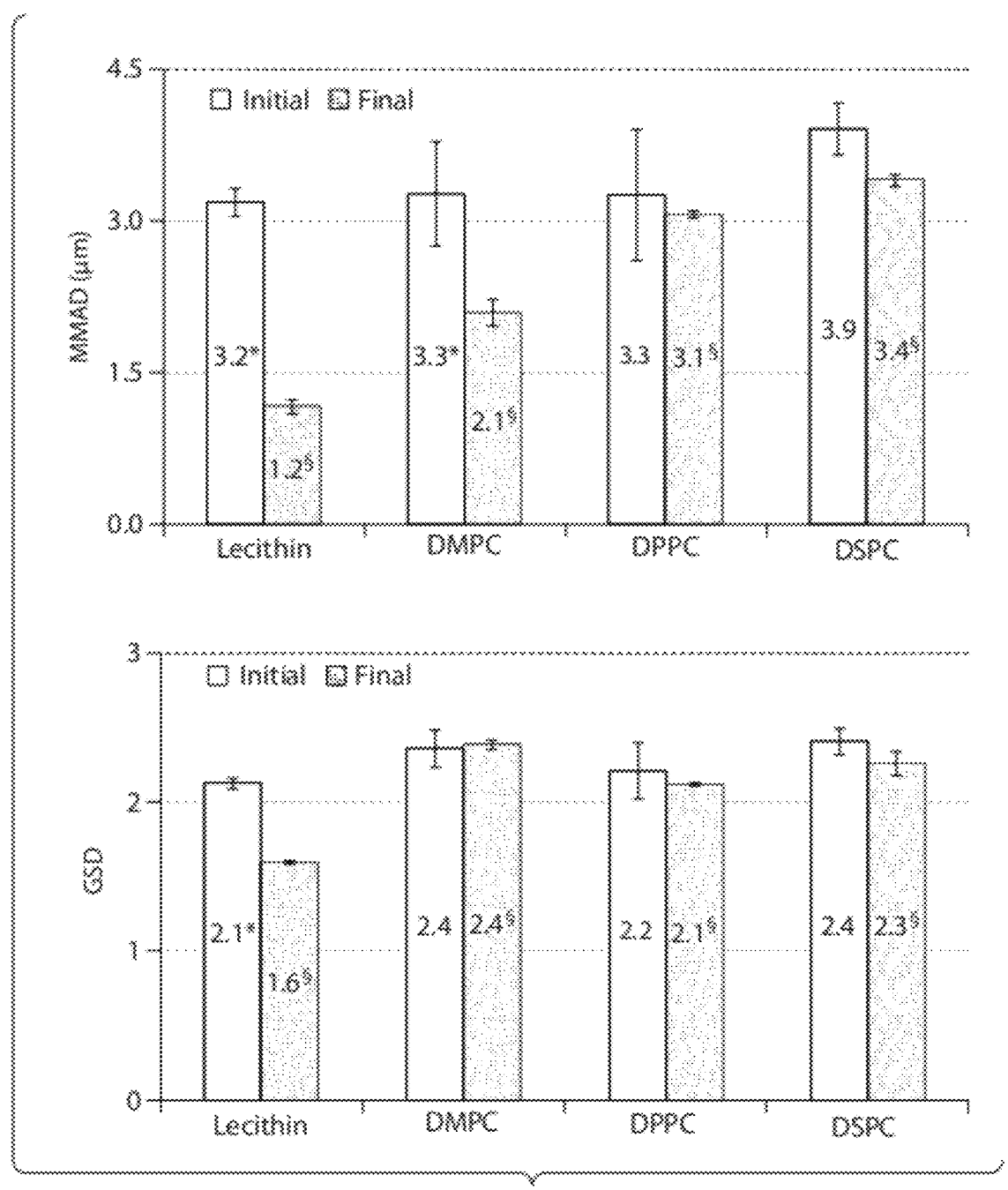
FIG. 28 shows the aerodynamic properties of lecithin, DMPC, DPPC and DSPC dispersions of CoQ10 at a flow rate of 15 L/min using an Aeroneb Pro® nebulizer. Results are expressed as means±standard deviations (n=3) of MMAD or GSD within a 15-second period at initial and final phases of a 15-minute nebulization event. *P<0.05 within nebulization event. § P<0.05 when compared to each other.

To further compare the aerodynamic properties of the aerosolized dispersions, the MMADs and GSDs are presented in FIG. 28. The MMAD and GSD values are initially similar for all four formulations. However, by the completion of the nebulization event, the values were different. This behavior indicates that the size of the emitted droplets containing drug nanoparticles is phospholipid dependent. Remarkably, the changes in transmittogram slope observed within the same nebulization event for lecithin and DMPC dispersions (FIG. 24) are reflected not only in the amount of drug being aerosolized (TED results, FIG. 25), but also on the aerodynamic properties shown in their in vitro NGI deposition profiles (FIGS. 26 and 27). As the nebulization progresses, the droplets aerosolized became smaller and fewer.

Figure 29B:
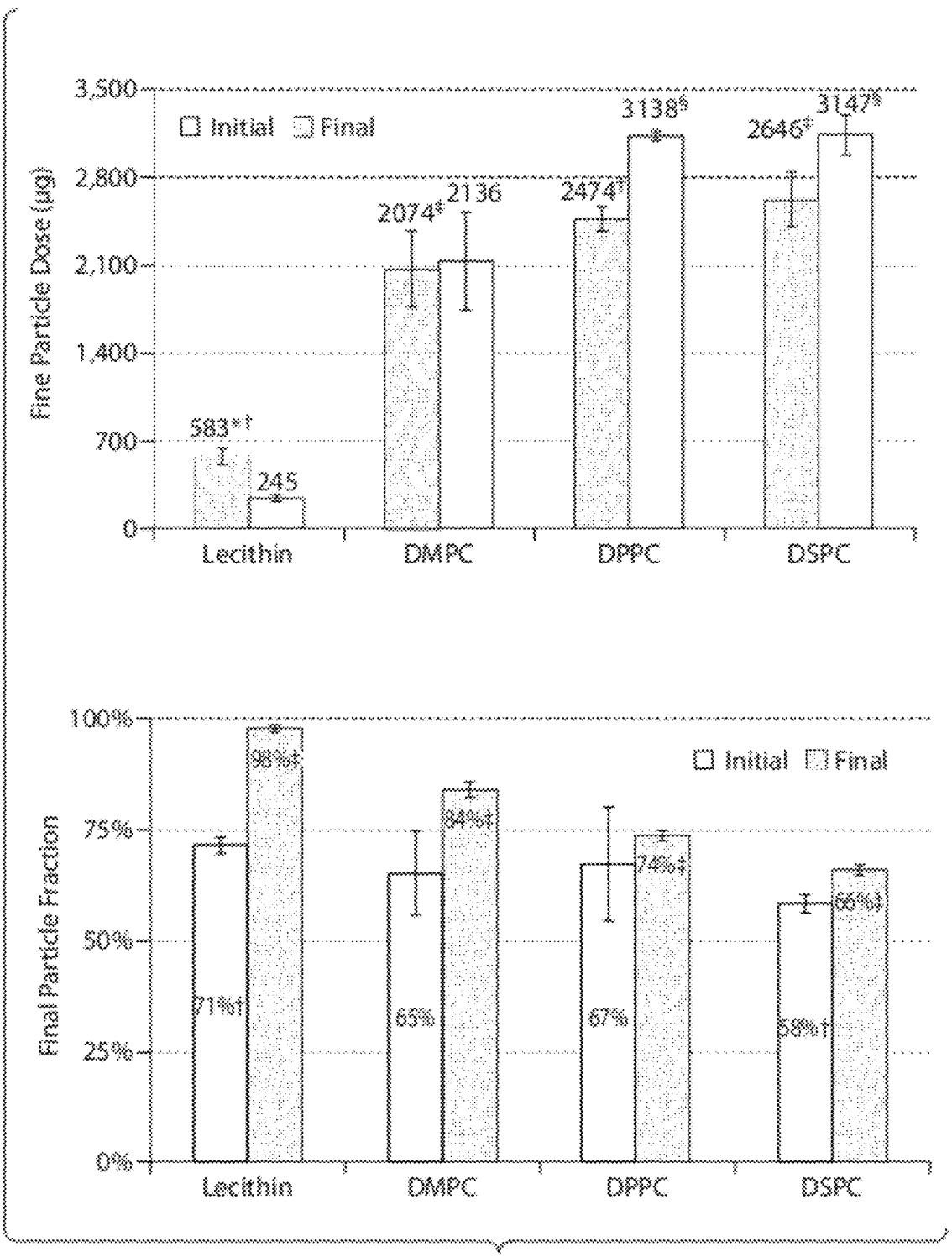
FIG. 29B shows estimated total dose (FPDet) and fraction (FPF) of aerosolized fine particles from lecithin, DMPC, DPPC and DSPC dispersions of CoQ10 at a flow rate of 15 L/min using an Aeroneb Pro® nebulizer. Results are expressed as means±standard deviations (n=3) related to a 15-second period at initial and final phases of a 15-minute nebulization event. *P<0.05 when compared to synthetic phospholipids. †P<0.05 within nebulization event. § Not statistically different compared to each other. ‡P<0.05 when compared to each other.

A further understanding of the nebulization output's potential for lung deposition can be obtained by analyzing fine particles (e.g., aerodynamic sizes below 5.39 μm). FIG. 29A shows the TED NGI and TED DUSA values for the studied formulations. The TED NGI data suggests that only the lecithin formulation exhibited a significant difference in drug amount aerosolized when comparing the initial and final phases within a 15-minutes nebulization. The TED DUSA values show that the lecithin and DMPC formulations exhibited a difference in drug amount aerosolized when comparing the initial and final phases within a 15-minutes nebulization. The TED DUSA results can be considered more meaningful because droplets containing the drug are directly deposited in a filter for measurement, whereas the TED NGI results can have losses throughout the NGI equipment aerosol passageways. FIG. 29B shows the FPDet and FPF values for the studied formulations. The FPF increased over time for all of the dispersions aerosolized with the Aeroneb Pro® nebulizer under the present experimental conditions, confirming that droplet sizes decreases during the course of nebulization. The FPD of the lecithin formulation changes drastically during nebulization. The MMAD values of aerosolized DMPC dispersions decreases during nebulization, while FPD does not statistically change. The DPPC formulation exhibited steady nebulization performance and, consequently, consistent TED values throughout nebulization. Although the MMAD values are not statistically different, the FPD results show that the DPPC formulation exhibit a higher amount of aerosolized drug by the end of nebulization. A similar behavior was observed for the DSPC formulation, but the results was not statistical significant (P=0.08) based on this example alone.

Figure 30:
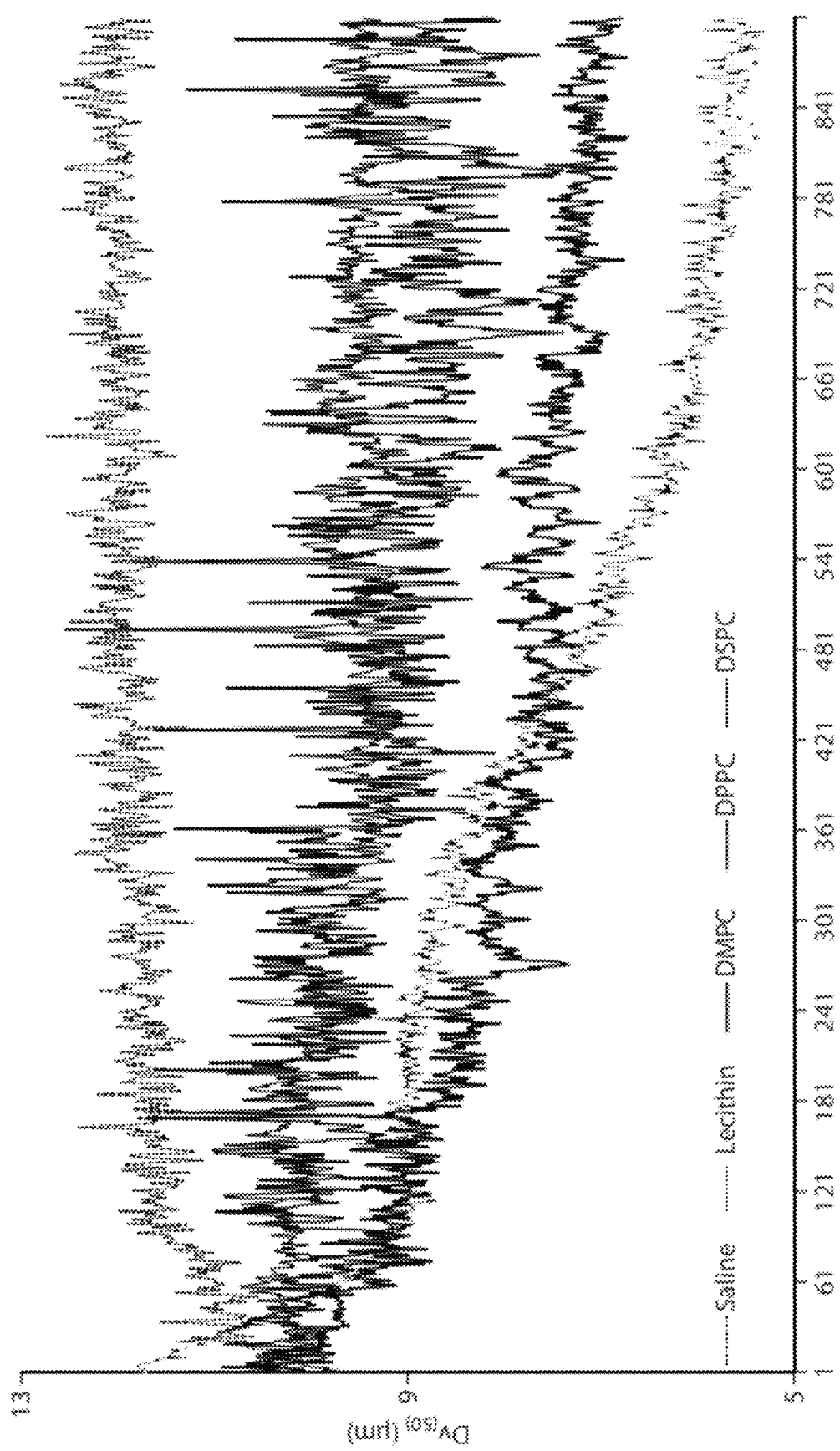
FIG. 30 shows average Dv(50) of CoQ10 dispersions aerosolized using Aeroneb Pro® nebulizer for 15 minutes (n=3).

FIG. 30 shows that the geometric sizes of the droplets containing CoQ10 particles also decrease over time, especially in the lecithin and DMPC formulations. Aerosols of the DPPC and DSPC formulations exhibited a relatively consistent (e.g., similar to the saline control) droplet size during the 15 minute nebulization. Discrepancies in aerodynamic and geometric sizes can be attributed to the different experimental setups (see discussion in Example 1).

Table 6 show the unprecedentedly high doses with the potential to reach the lungs (based on FPD) exhibited by the present invention, with the DPPC and DSPC formulations presenting the highest values. These doses are approximately 10 to 40 times greater than itraconazole nanodispersions previously aerosolized using the same type of nebulizer (vibrating-mesh device, data not shown) and as much as 280 times greater than previous aerosolization of budesonide suspension (Pulmicort Respule®, AstraZeneca, UK) using a Sidestream® PortaNeb® jet nebulizer (Medic-Aid Ltd., UK). Of perhaps equivalent importance, the present invention allows for verifying the quality and quantity of nebulization (e.g., bolus vs. steady aerosol during nebulization event).

In some cases refinements can be necessary for effective drug loading. For example, water evaporation can occur during hot high pressure homogenization. Similarly, the small volume of formulation prepared (e.g., 100 mL) can result in drug loss through deposition on the manufacturing equipment.

Finally, the observed changes in nebulization performance during nebulization events have been shown to correspond to differences in aerodynamic properties between the different formulations. Nevertheless, the rheological behavior of these formulations was shown to be compatible with active vibrating-mesh nebulizer for continuously nebulizing phospholipid-stabilized nanodispersions of hydrophobic bioactive agents. The concentration of the various elements of the dispersion (e.g., hydrophobic bioactive agent) has a significant role in determining the critical shear rate at which the shear thickening event post-second Newtonian plateau begins. Thus, knowledge of a dispersion's rheology can be used to identify a maximum drug loading while still maintaining a desired nebulization performance. Nebulizer aerosol generation occurs through application of a stress (e.g., air jet stream, ultrasonic force, vibrating-mesh) into or onto the bulk liquid formulation. Therefore, the methodology provided herein, including the combination of rheological studies of dispersions and analysis of nebulization performance using LD techniques, provides for the formulation development of hydrophobic drugs continuous nebulizer based inhalation therapy.

Example 3

Pulmonary Deposition and Systemic Distribution in Mice of Inhalable Formulations of CoQ10

Example 3 presents an evaluation of in vivo systemic distribution, lung, and nasal depositions in mice following pulmonary delivery of CoQ10 formulations prepared with synthetic phospholipids. Three synthetic phospholipids were selected to stabilize these dispersions based upon the experimental results presented above and because of the phospholipids physiological occurrence in the lungs: DMPC, DPPC, and DSPC. Lecithin was not selected as a results of its low in vitro deposition. The dosing apparatus includes a nose-only inhalation chamber receiving aerosol generated by an Aeroneb Pro® vibrating-mesh nebulizer. The results showed the achievement of a high and sustained dose of CoQ10 to the mice's lungs, which varied from 1.8 to 3.0% of the theoretical exposure.

Materials and Methods
Materials:

CoQ10 was supplied by Asahi Kasei Corp. (Tokyo, Japan). Genzyme Pharmaceuticals (Liestal, Switzerland) provided 1,2-dimyristoyl-sn-glycero-3-phosphocholine (DMPC), 1,2-dipalmitoyl-sn-glycero-3-phosphocholine (DPPC), and 1,2-distearoyl-sn-glycero-3-phosphocholine (DSPC). DMPC was also obtained from Lipoid GmbH (Ludswighafen, Germany). Sodium chloride (crystalline, certified ACS) was acquired from Fisher Chemical (Fisher Scientific, Fair lawn, NJ, USA) and the deionized water was obtained from a central reverse osmosis/demineralizer system. Mouse restraint tubes (item E2QY-PC), anterior nose inserts (item E2TE-N) and posterior holders (item E2TA-N) were purchased from Battelle Toxicology Northwest (Richland, Wash., USA). A fan (12V, 0.10 A, model OD4020-12HB) was purchased from Knight Electronics (Dallas, Tex., USA). HPLC grade hexane and ethanol 200 proof were purchased from Sigma-Aldrich (St. Louis, Mo., USA). Syringes (1 mL) and needles (gauges 21G1 and 23G1) were obtained from Becton Dickinson (Franklin Lakes, N.J., USA). Heparinized tubes (1.3 mL microtubes Lithium Heparin (LH) with screw cap closure, product no. 41.1393.105) were purchased from Sarstedt AG & Co. (Numbrecht, Germany). Microcentrifuge tubes (1.5 mL, clear, RNase/DNase free, BL3152) were obtained from Bio-Link Scientific, LLC (Wimberley, Tex., USA).

Formulation:

Formulations were prepared using high pressure homogenization as described in Example 2. To summarize, following overnight hydration while stirring, a phospholipid dispersion containing 2.5% w/w of phospholipids (DMPC, DPPC, or DSPC) in water was added to the molten CoQ10 (4% w/w) at 55° C. The formulation was predispersed, using an Ultra-Turrax® TP 18/10 Homogenizer with 8 mm rotor blade, by high shear mixing (IKA-Werke, Staufen, Germany) for 5 minutes at 20,000 rpm. The formulation was then passed 50 times through a M-110P "Plug-and-Play" Bench-top Microfluidizer® (Microfluidics, Newton, Mass. USA) at approximately 30,000 psi while maintaining a temperature between 55 and 65° C. Following microfluidization, 0.9% w/v of sodium chloride was added to the final formulation. A formulation for the control group was similarly prepared using DPPC in absence of drug (CoQ10 was not added).

Figure 31:
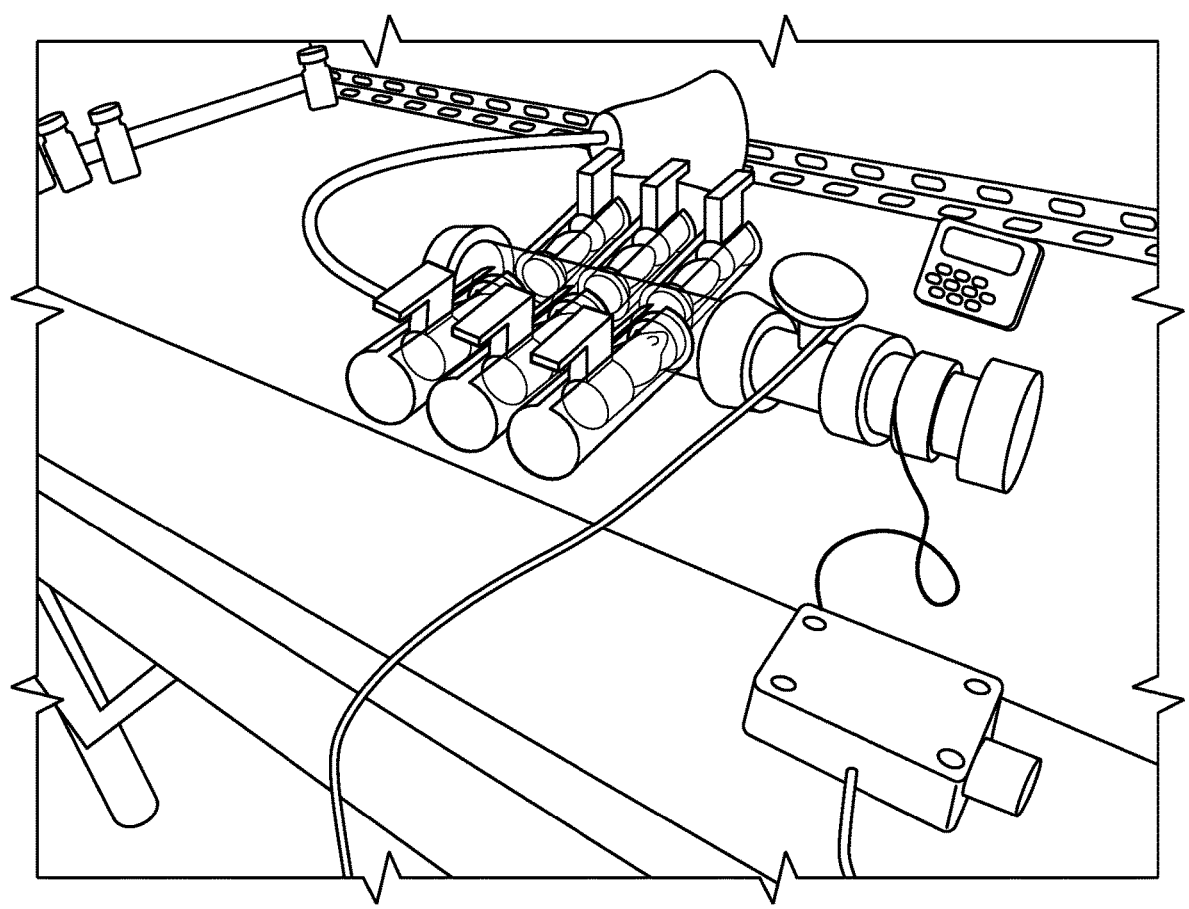
FIG. 31 shows an example nose-only dosing apparatus used to aerosolize CoQ10 to mice. Six mice are individually restrained in a tube, exposing their noses to the chamber. The nebulizer is positioned between the chamber and the fan that will provide sufficient airflow to fill the chamber with the drug aerosol. The tubing system is open to avoid drug recirculation.

Pulmonary Delivery to Mice:

Animals were caged in groups of 4 and maintained on a normal rodent chow diet with free access to water. A nose-only chamber apparatus capable of dosing six mice at a time was assembled as shown in FIG. 31. Prior to dosing, CD-1® IGS ICR mice (Charles River Laboratories International, Inc., Wilmington, Mass., USA) were individually acclimatized for approximately 10 minutes per day for 3 days into restraint tubes, restricted by an anterior nose insert and a posterior holder. The dosing apparatus was placed inside a fume hood to collect escaping aerosol containing drug. To avoid influence from the airflow provided by the fume hood, an erlenmeyer container was placed at the end of the tubing system as a buffer. The airflow rate was set to 1 L/min to ensure proper drug aerosolization into the nose-only chamber (internal volume: 230 mL; diameter: 3.8 cm; length: 20.3 cm) using an Aeroneb Pro® vibrating-mesh nebulizer (Aerogen, Galway, Ireland). Following preparation, all formulations (saline control, DMPC, DPPC, and DSPC) were dosed for 15 minutes to mice weighing from 23 to 33 g each, at time of dosing. Each single-dose studied group consisted of thirty-six male animals. At each time point (0.5, 1, 3, 8, 24, and 48 hours after the end of the aerosolization event) six animals randomly selected from different dosing events of the same formulation were sacrificed by narcosis with carbon dioxide. As part of the collection process, blood was withdrawn by cardiac puncture, lungs were harvested, and a nasal wash was performed. The samples were extracted for analysis with liquid chromatography coupled with tandem mass spectrometry (LC/MS/MS).

Estimated Dose:

To estimate the dose to which mice were exposed during this study, it was assumed that the nose-only chamber gradually fills with the aerosol containing CoQ10. Therefore, the drug concentration steadily increases until it reaches a plateau. At steady-state, it is also assumed that the rate of drug entering the chamber is equal to the rate of drug leaving the chamber (dC/dt=0). Therefore, Equation 5 can be used to measure the drug concentration inside the chamber at any given time:

$$C = FPDr/F^* (1 - e^{-\lambda t}) \quad \text{(Equation 5)}$$

Where C is the drug concentration, FPDr is the rate of delivery of the Fine Particle Dose (the amount of particles with aerodynamic cutoff diameter below 5.39 μm per minute) as determined in the previous chapter, F is the airflow rate, λ is the chamber air-change rate and t is any given time within the nebulization period. The chamber air-change rate, λ, can be determined based on the airflow rate and on the chamber internal volume, V, based upon Equation 6:

$$\lambda = F/V \quad \text{(Equation 6)}$$

Based on these assumptions, the following Equation 7 describes the estimated dose delivered to mice:

$$\text{Estimated Dose} = RMV \cdot \frac{FPD_r}{F} \cdot \left\{ t' + \frac{V}{F} \cdot [(e^{-\lambda t'}) - 1] \right\} \quad \text{(Equation 7)}$$

Where RMV is the species-specific Rate Minute Volume and t' is the duration of the nebulization event. The estimated dose as calculated above can then be normalized by the animal body weight, W (g). RMV is calculated in accordance with Equation 8:

$$RMV = 4.19 * W^{0.66} \quad \text{(Equation 8)}$$

Analysis of CoQ10 Levels in Lung Tissue, Blood Plasma, and Nasal Cavity:

For each experiment, CoQ10 levels were determined after liquid extraction using liquid chromatography coupled with tandem mass spectrometry (LC-MS/MS). The methods were validated in the drug concentration range of 0.1 to 600 µg/mL. The general sample preparation protocols for lung tissue, blood plasma, and nasal cavity analysis are described below.

Following harvesting of the mice lungs, the tissue was weighed (wet weight), frozen in dry ice, and transferred to a −80° C. refrigerator for storage until to analysis. After samples were thawed for analysis, lung tissue (50±1.5 mg) was weighed subsequently homogenized with Dulbecco's Phosphate Buffer Saline (dPBS). Homogenate (100 µL) and internal standard were added to isopropanol (IPA) and vortexed. Following centrifugation, the supernatant (100 µL) was added to another tube containing IPA. The sample was vortexed again and transferred for LC-MS/MS analysis.

Following cardiac puncture, approximately 1 mL of mice blood was collected in heparinized tubes and kept in ice bath until centrifugation for 10 minutes at 7000 g. The supernatant was then transferred to 1.5 mL microcentrifuge tubes and kept refrigerated at −80° C. until analysis (see lung tissue procedure described above).

A solvent wash was performed to evaluate the amount of drug deposited into the nasal cavity. The murine nasal cavity was directly accessed from the posterior portion of the hard palate by inserting a needle into the nasopharynx and flushing the nasal fossa with hexane:ethanol 2:1 (v/v). The solvent was collected in a scintillation vial from the anterior (frontal) portion of the nose and subsequently allowed to dry at room temperature. The sample was then re-suspended and injected into LC-MS/MS for quantification of CoQ10.

Statistical Analysis:

Samples were tested for normality using the Shapiro Wilk test ($p < 0.05$) and outliers were excluded from data analysis. Pharmacokinetic parameters were determined using Microsoft Office Excel 2007 software (Redmond, Wash.) with the add-in program PKSolver. Statistical analysis was performed using NCSS/PASS software Dawson edition. At each time point, lung tissue samples were analyzed for statistical differences among different groups with One-Way ANOVA for significance ($p < 0.05$). The same analysis was performed for nasal wash samples, with additional post hoc multiple comparison tests performed to identify statistically significant differences between treated and control groups using Dunnett's method ($p < 0.05$). A paired t-test was performed to analyze statistical differences ($p < 0.05$) within the same treatment group for changes in drug deposition in the nasal cavity over time.

Results and Discussion

A nebulizer was used to generate aerosol for dosing mice for 15 minutes with control, DMPC, DPPC, and DSPC formulations. The dose delivered to the lungs was estimated based on the FPDr values, as determined during the in vitro characterization of drug deposition using the Next Generation Impactor (NGI) described in Example 2.

Figure 32:
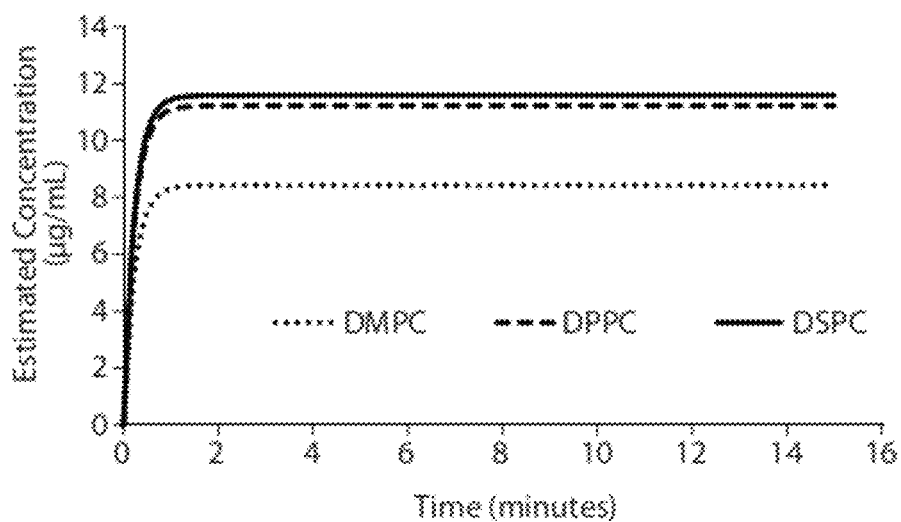
FIG. 32 shows estimated drug concentration-time profiles of CoQ10 inside the nose-only inhalation chamber.
Figure 33:
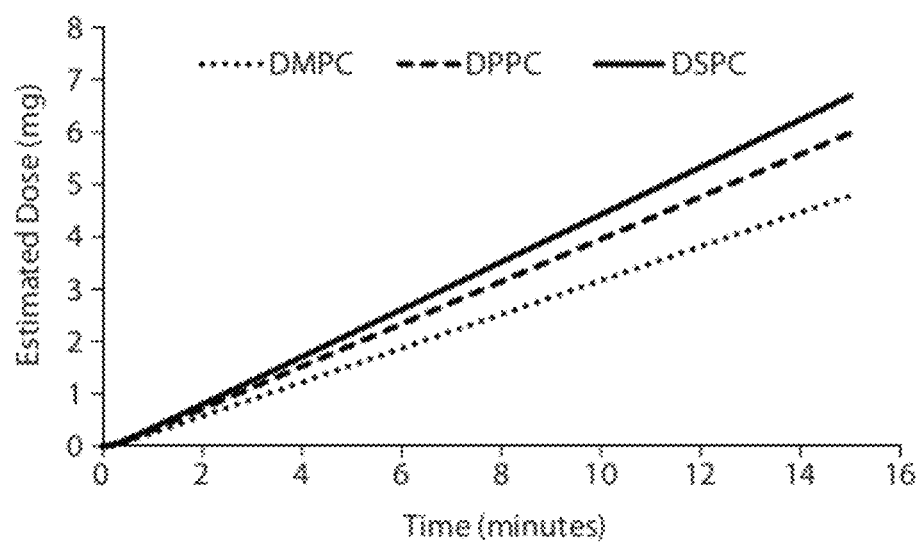
FIG. 33 shows cumulative estimated doses of CoQ10 from synthetic phospholipid formulations aerosolized to mice into a nose-only inhalation chamber during 15 minutes.

FIG. 32 shows the calculated drug concentration-time profile within the dosing chamber. A plateau is reached at 3.0 minutes. The concentration at steady-state (CSS) is equal to FPDr since the airflow rate during this experiment was 1 L/min (Table 7). The chamber air-change rate was 4.35 $min^{-1}$. The estimated doses delivered to mice of aerosolized DMPC, DPPC, and DSPC dispersions of CoQ10 for 15 minutes increases in this respective order (FIG. 33). When normalized to the body weight of animals, similar estimated doses were delivered to mice receiving either DPPC or DSPC formulations. These doses of CoQ10 were found to be greater than when the mice were dosed with the DMPC formulation.

Figure 34:
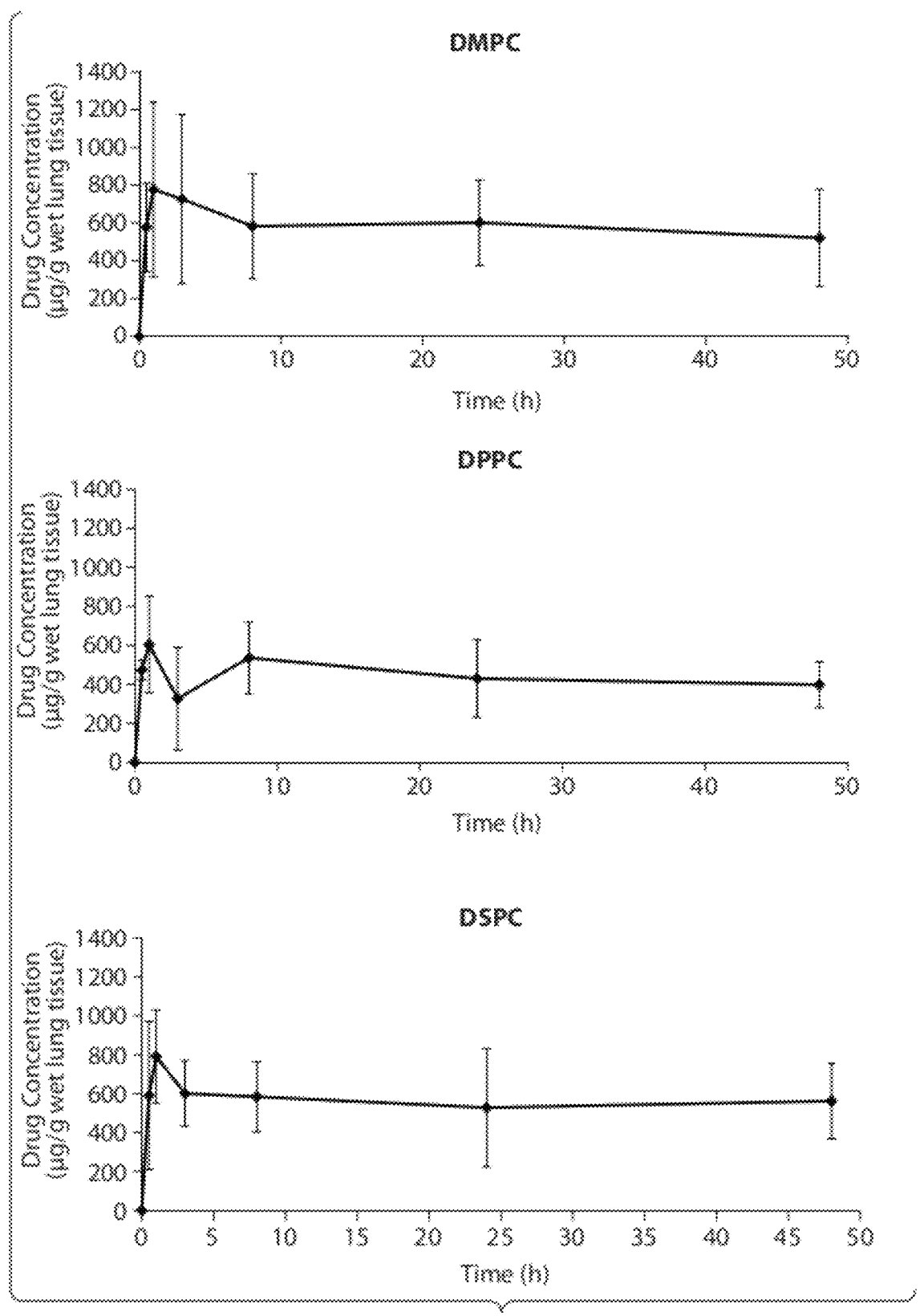
FIG. 34 shows mean lung concentrations normalized to wet lung tissue of CoQ10 from synthetic phospholipid dispersions following aerosolization to mice into a nose-only inhalation chamber during 15 minutes. Error bars indicate standard deviation (n=6).

The drug concentration in plasma was below the quantitative level (0.1 µg/mL) for all studied groups at every time point. The baseline concentration of CoQ10 in mice blood plasma is approximately 0.1 µmol/L (86 ng/mL). In the lungs, the drug concentration was also below the quantitative level for the control group at every time point investigated. However, FIG. 34 shows that CoQ10 stays in the lungs at relatively high concentrations for up to 48 hours. The mechanism by which CoQ10 could be absorbed through the lung epithelium is unknown. Without wishing to be bound by any particular theory, it is believed that, despite the lipophilicity of CoQ10, passive diffusion is only part of a more complex absorption process involving an additional active and facilitated transport phenomena. It is possible that the relatively small amount of lungs to systemic translocation is, at least in part, part due to this low permeability. In addition, the dispersions are formulated in the nano-size range, which are known (e.g., with respect particles below 0.2-0.5 µm) to be stealth to alveolar macrophages. In addition to size, other physicochemical properties of the drug can influence the translocation of nanoparticles across the air-blood barrier, for example: particle material, in vivo solubility, and binding affinity to cell membranes (e.g. through surface charge and structure). The presence of phospholipids in these formulations may have also caused a greater lung peripheral distribution of the drug nanoparticles.

The translocation of insoluble nanoparticles across the air-blood barrier is known to be minimal compared to the long term clearance from the alveoli up to the mucociliary escalator and into the GI tract, which can take weeks. A significant spreading of drug towards the lung periphery due to the presence of phospholipids in the formulations investigated in this study is a possible contributing factor explaining why the clearance of CoQ10 from the lungs was not detected after 48 hours and similarly why the drug levels in the plasma were below the quantitative limit. Furthermore, because drug clearance from the lungs was not significant in the studied time period, the elimination constants and half-lives could not be determined for the nebulized formulations.

Figure 35:
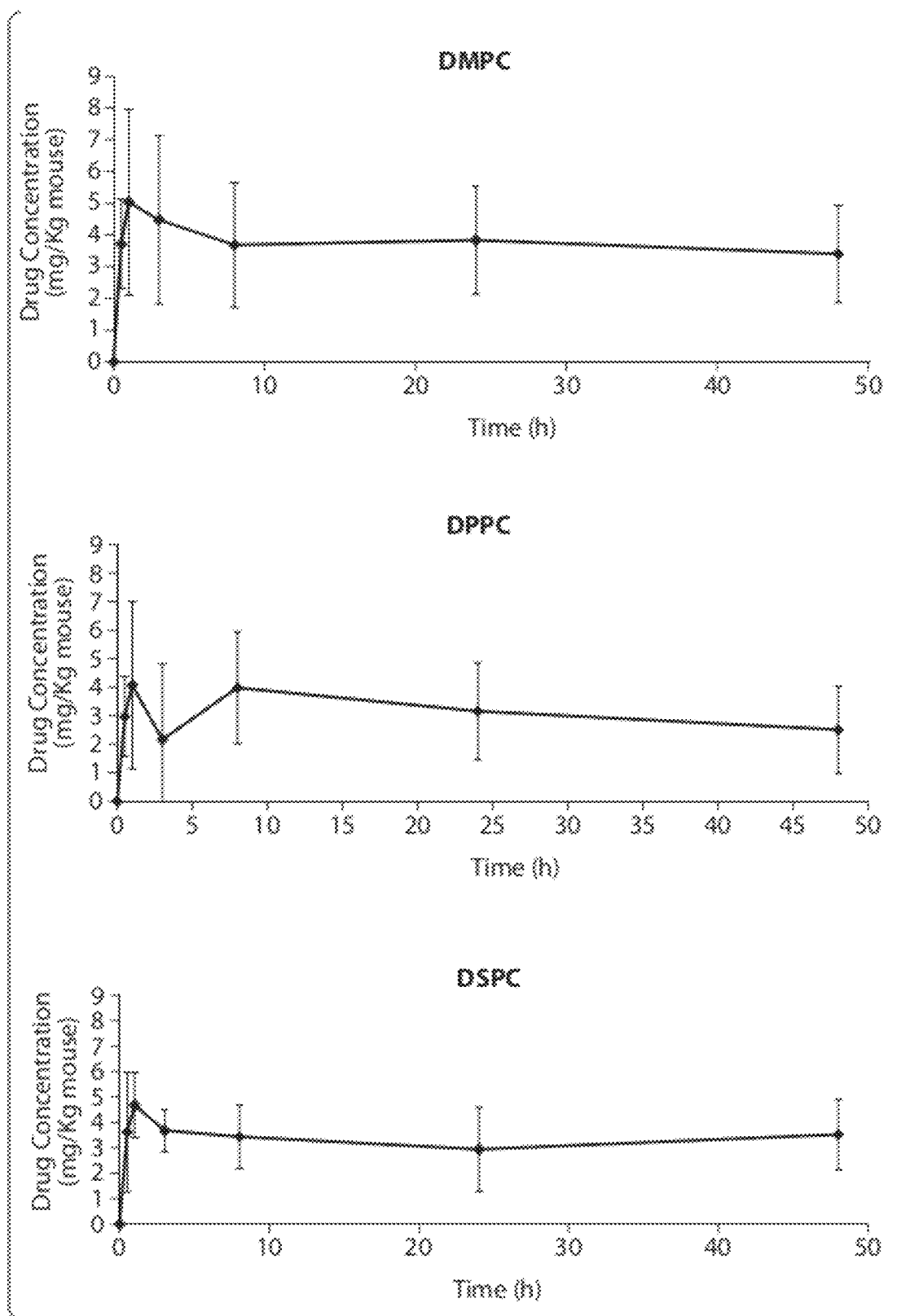
FIG. 35 shows mean lung concentrations normalized to animal body weight of CoQ10 from synthetic phospholipid dispersions following aerosolization to mice into a nose-only inhalation chamber during 15 minutes. Error bars indicate standard deviation (n=6).

Other pharmacokinetic parameters are presented in Table 8. The lung deposition profiles of aqueous dispersions of CoQ10 using different phospholipids presented relatively similar results. The Cmax ranged from 604.0 to 791.3 µg/g of wet lung tissue, and was observed 1 hour (tmax) post dosing for all treated groups. These values translate to approximately 4.0 to 5.0 mg/kg of mouse body weight and correspond to 1.8 to 3.0% of the theoretical exposure dose (FIG. 35). The AUC0-48 results were surprisingly different; with the DMPC formulation of CoQ10 presenting the highest value regardless of whether the smallest estimated dose that the mice were exposed to was presented. Although DPPC and DSPC dispersions of CoQ10 presented high estimated dose, their Cmax and AUC0-48 values varied widely. No statistical differences were found in drug concentration at the same time point among the treated groups (FIGS. 34 and 35).

Figure 36:
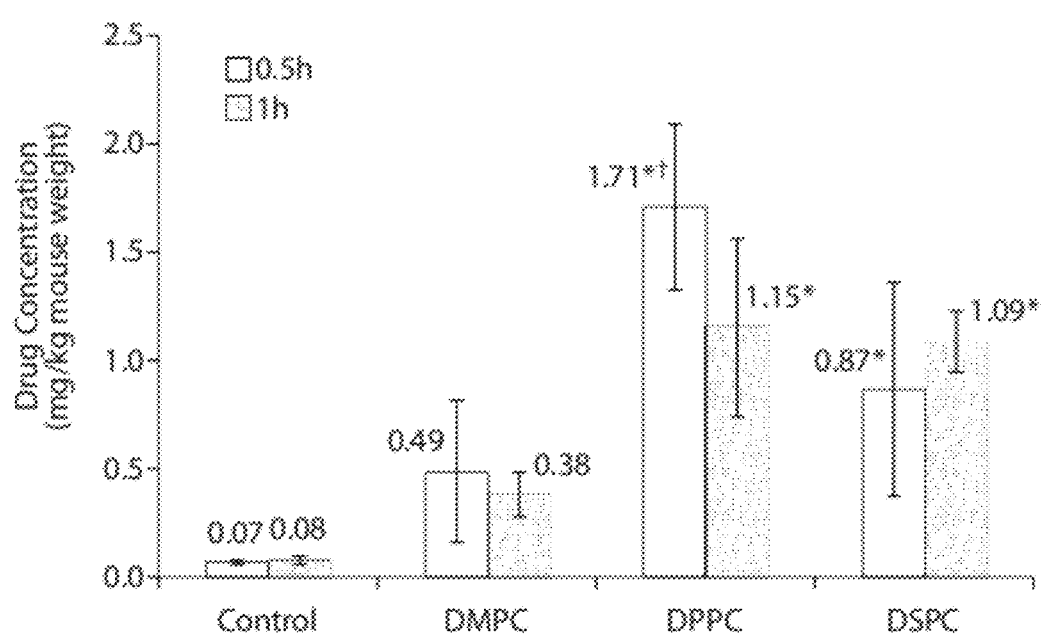
FIG. 36 shows deposition of CoQ10 in the nasal cavity of mice 0.5 and 1 hour post 15-minute nebulizer dosing. Results are expressed as means±standard deviations (n=6). *P<0.05 when compared to control group. †P<0.05 when compared within the same group.

The drug deposition in the nasal cavity was lower than that which was measured in the lungs (FIG. 36), not exceeding an average of 1.7 mg/kg of mouse body weight among the treated groups. Only the DPPC group demonstrated a statistically significant decreasing trend for the first two time points investigated. A small amount of CoQ10 was observed in the control group, possibly from an endogenous source. Finally, all mice were alive and presenting healthy signs 48 hours after the end the nebulization event. This demonstrates the safety of delivering high amounts of exogenous CoQ10 to the lungs.

In Example 2, unprecedentedly high doses with potential to reach the lungs based on FPDet results were predicted, with DPPC and DSPC formulations presenting the highest values. These doses are approximately 10 to 40 times greater than itraconazole nanodispersions previously aerosolized using the same type of nebulizer (vibrating-mesh device) and as much as 280 times greater than previous aerosolization of a budesonide suspension (Pulmicort Respule®, AstraZeneca, UK) using a Sidestream® PortaNeb® jet nebulizer (Medic-Aid Ltd., UK). This Example verified that the high doses translated into an improved drug deposition in the lungs. Cmax values of CoQ10 were as much as 75-fold and 165-fold higher than previous studies using the same nebulizer to deliver dispersions of cyclosporine A and itraconazole, respectively (data not shown). These data present a significant improvement in delivery of high amounts of hydrophobic drug directly to the lungs. The in vitro methods of the invention for designing and screening formulations with optimized potential to deliver high drug amounts to the lungs were essential in achieving these results.

Example 4

Low Concentration Range Determination of Hydrophobic Drugs Using HPLC

Preclinical and clinical studies require the determination of small amounts of compounds (e.g., hydrophobic drugs such as CoQ10) in different biological fluids and tissues. Currently, there are many analytical methods of HPLC with ultraviolet (UV) detectors available. However, for high sensitivity analysis, more sophisticated and complex methods are required, for example: HPLC followed by chemical reactions, HPLC with electrochemical detectors (ECD) and liquid chromatography-triple quadrupole (tandem) mass spectrometry (LC-MS/MS). Among the parameters for validation of HPLC methods are accuracy, precision, range, linearity and limits of detection (LOD) and quantification (LOQ). Signal-to-noise (S/N) ratio is a quick and simple method to determine LOD and LOQ, which are essential when analyzing low concentration of drugs.

Methods:
A Waters HPLC and column system including a 1525 binary pump, a 717 autosampler, a 2487 dual λ absorbance detector, set at 275 nm, and a Symmetry RP-C8 column 5 μm (3.9×150 mm) connected to Symmetry C8 guard column 5 μm (3.9×20 mm) was selected. The mobile phase (MP) includes Methanol:Hexane at 97:3 (v/v). Stock solution of pure CoQ10 was initially dissolved in Hexane:Ethanol (diluent) at a ratio of 2:1 (v/v) and subsequently diluted with the mobile phase to obtain the desired concentration. Limit of Detection (LOD), Limit of Quantification (LOQ) and linearity (3-interday curves) were determined by injecting 50 μL samples at a controlled temperature of 30° C. Chromatogram peaks were acquired within run time of 11 minutes at a flow rate of 1.0 mL/min. Area and height of peaks were used to determine curve linearity. LOD and LOQ were defined by signal-to-noise (S/N) ratio calculations according to method from the European Pharmacopoeia, with minimum acceptable values of 3 and 10, respectively. Concentration points were 10, 25, 37.5 and 50 ng/mL (n=6).

For mobile phase preparation, solvents were filtered prior to use through 0.45 μm nylon membrane filters and sparged for 10 minutes with helium gas. For preparation of stock and working standard solutions (500 μg/mL), 12.5 mg of CoQ10 was accurately weighed in a 25 mL amber volumetric flask and dissolved in hexane-ethanol (2:1 v/v). Subsequently, this stock standard solution was diluted with MP to 10 μg/mL. To avoid light degradation of the API, standard solutions were kept in amber containers during drug manipulation. Working standard solutions were prepared by transferring suitable aliquots of stock solution to transparent tubes and diluted to final concentration with MP. Finally, the working standard solutions were transferred to polypropylene conical containers and placed them in amber HPLC vials for analyses.

Results:
The retention time (RT) of CoQ10 was determined as approximately 8 minutes and injection of blank sample (diluent) shown not to interfere in peak determination at 275 nm. Temperature control was observed to be essential to obtain symmetric peaks at lower concentrations. LOD and LOQ were defined as 10 ng/mL (n=6; S/N ratio=6.0; SD=0.6; RSD=10.5%) and 25 ng/mL (n=6; S/N ratio=12.6; SD=1.3; RSD=10.1%); respectively. The curve linearities were obtained using height or area of the chromatogram peaks in the range of 25 to 2500 ng/mL with $r^2 \geq 0.9999$ (n=3 for each concentration).

Conclusion:
The method can be used as an alternative to more complex and expensive methods for analysis of CoQ10 in small concentrations. The ease of sample preparation and small retention time allows for a quick analysis. The possibility of using either the area or the height of chromatogram peaks gives more flexibility to adapt this method to different applications. Further studies on extraction of CoQ10 from biological materials, stability, and internal standard selection are needed to define the role of this method. This study provides an alternative and suitably stable method to determine CoQ10 at very low concentrations using an economically viable RP-HPLC system.

Example 5

Determination of Suitable Hydrophobic Drug Concentrations in Phospholipid Nanodispersions Suitable for Continuous Nebulization In developing hydrophobic drug formulations for continuous nebulization, it can be useful to establish a maximum nominal drug loadings to phospholipid-stabilized dispersions that will sustain continuous vibrating-mesh nebulization. This is because, for example, vibrating-mesh nebulizer can exhibit problems such as variable aerosolization due to clogging of mesh pores that can be mitigated by appropriate formulation.

Methods:
Formulations were prepared based upon the general methods discussed in connection with Examples 1 and 2. For this study, specific dispersions were prepared with 50 microfluidization discrete passes using 2.5% w/w of dimyristoyl phosphatidylcholine (DMPC) and 7.5%, 7.0%, 6.0%, 5.0%, or 4.0% w/w of CoQ10. The dispersions were then aerosolized within 24 hour using an Aeroneb Pro® nebulizer for 15 minute aerosolization event. The aerosolization profile was monitored via analysis of Total Aerosol Output (TAO) and using laser diffraction with a Malvern Spraytec® coupled with an inhalation cell as described above.

Figure 37:
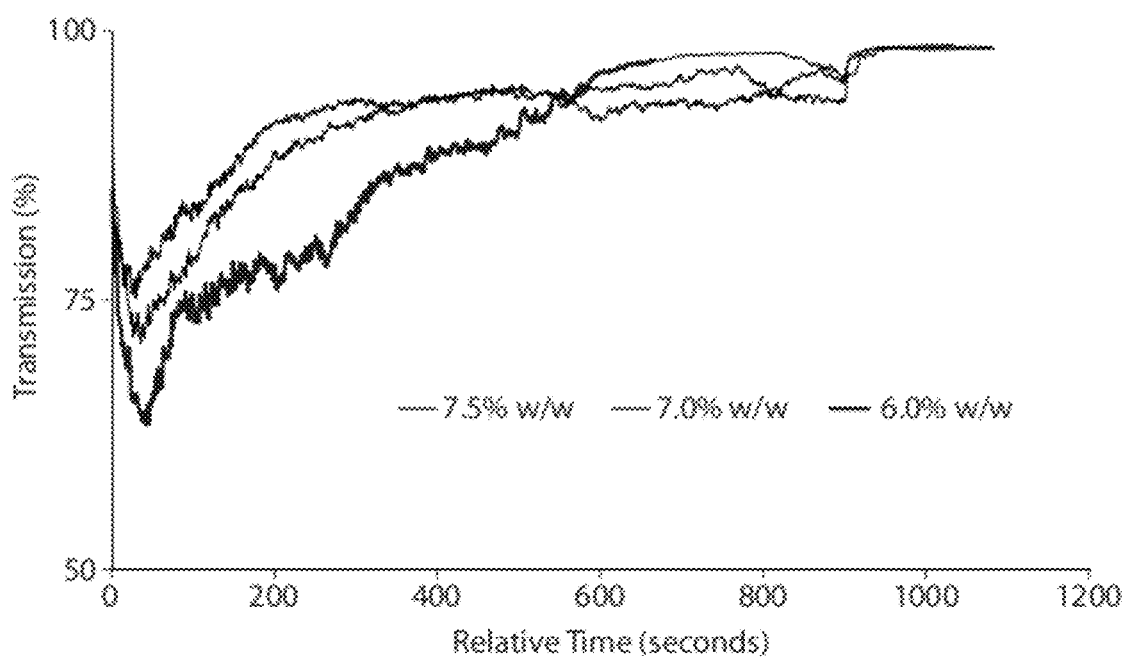
FIG. 37 shows transmittograms of aerosolization of DMPC-stabilized dispersions with different concentrations of CoQ10.

Results and Discussion:

The nebulization performances of the DMPC-stabilized formulations are presented in FIG. 37. As the hydrophobic drug concentration decreases, the aerosolization becomes more continuous. The TAO values for decreasing drug concentrations are, respectively, 1.25 g (12.4%), 1.62 g (16.1%) and 2.15 g (21.4%)° The TAO results are in agreement with the analysis of nebulization performance from laser diffraction, with increasing values as the drug concentrations decrease. The transmission values do not return to 100% at the end of nebulization, due to an experimental artifact. Although a formulation containing 5% w/w of CoQ10 was prepared, the analysis using laser diffraction could not be performed appropriately due to this artifact. Based on visual observation, it was determined that this drug concentration was not suitable for continuous aerosolization of the CoQ10 dispersion because of generation of intermittent mist during nebulization. For the 4.0% w/w CoQ10 formulation, this intermittence was only observed at the end phase of nebulization, therefore being chosen as a suitable nominal drug concentration.

Conclusion:

The nominal concentration of 4% w/w of CoQ10 was determined to be the appropriate drug loading for continuous aerosolization with the Aeroneb Pro® nebulizer as established using DMPC at 2.5% w/w to stabilize the dispersions. Nominal concentrations can vary depending upon the specific hydrophobic drug used, as well as other components of the formulation such as the phospholipid.

Example 6

Measuring Inflamatory Reponse to Pulmonary Administration of Dispersions of Phospholipid Encapsulated Hydrophobic Bioactive Agents The inflammatory response to the administration of hydrophobic bioactive agents (e.g., as discussed in connection with Example 1-3 above) was measured. Surgery is performed on sacrificed mice to expose the pleural cavity and trachea at the throat. A small incision is cut into the trachea and a cannula possessing about a 23 gauge needle with a sheath of plastic tubing (about 0.037 inch outside diameter (OD) and about 0.025 inch ID) is inserted through the incision to the base of the trachea and clamped to seal the opening. An aliquot (about 0.75 mL) of phosphate buffered saline is instilled through the cannula into the lungs and removed to wash the bronchial and alveolar surfaces. This process is repeated for a total of three washes. The phosphate buffered saline containing cells is placed into centrifuge vials and centrifuged at about 3000 rpm (MiniSpin Plus, Eppendorf International, Hamburg, Del.). The supernatant is removed leaving the collected cells in the pellet. The supernatant from the BAL (Bronchoalveolar Lavage) is analyzed by enzyme-linked immunosorbent assay (ELISA) for IL-12 elevation (n=2 per sample tested). Administering CoQ10 is not associated with a rise in IL-12 levels and does not cause lung inflammation.

Example 7

Figure 38:
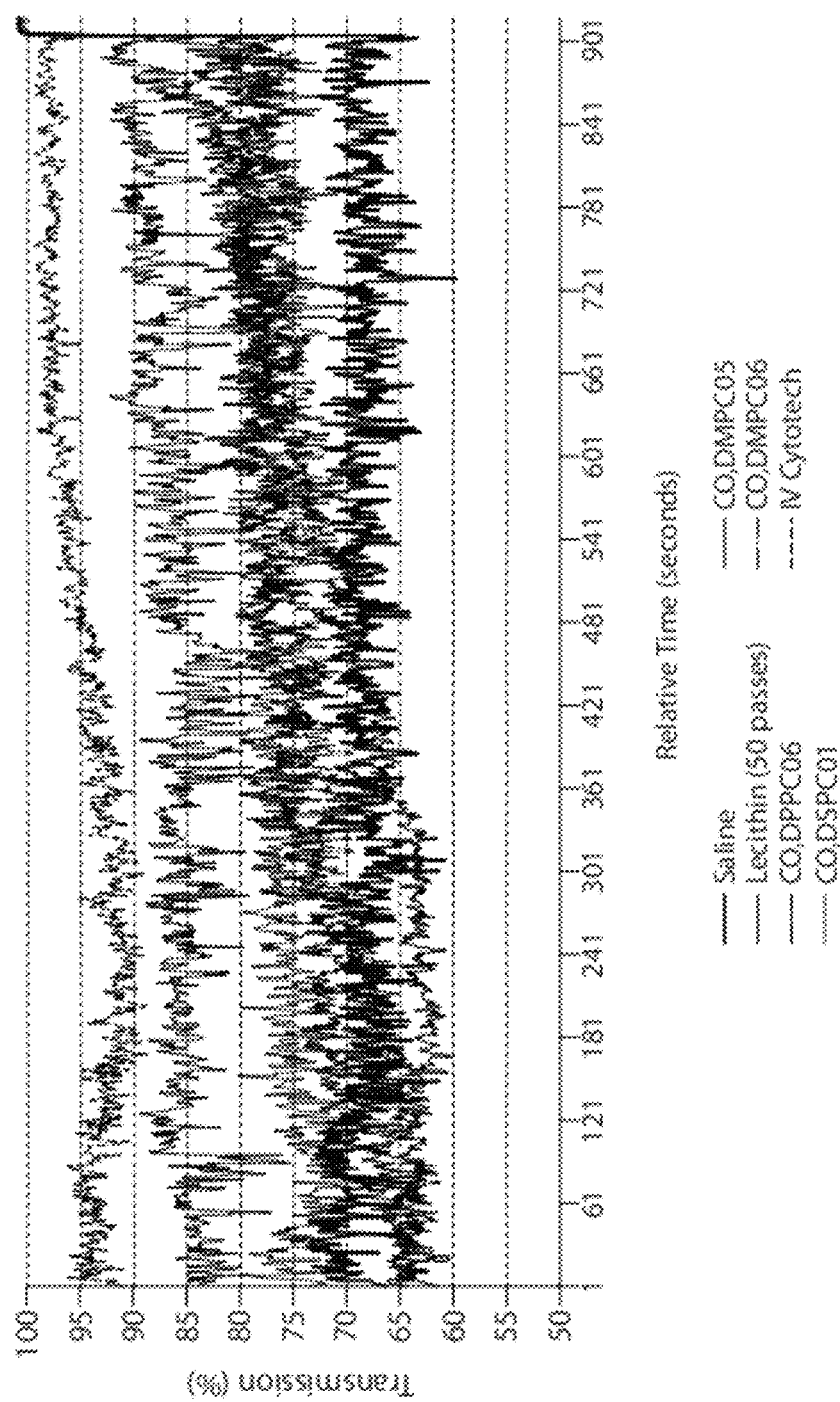
FIG. 38 shows transmittograms of aerosolization of DMPC- and DSPC-stabilized dispersions, as compared to an intravenous formulation that includes a particular opsonisation reducer.
Figure 39:
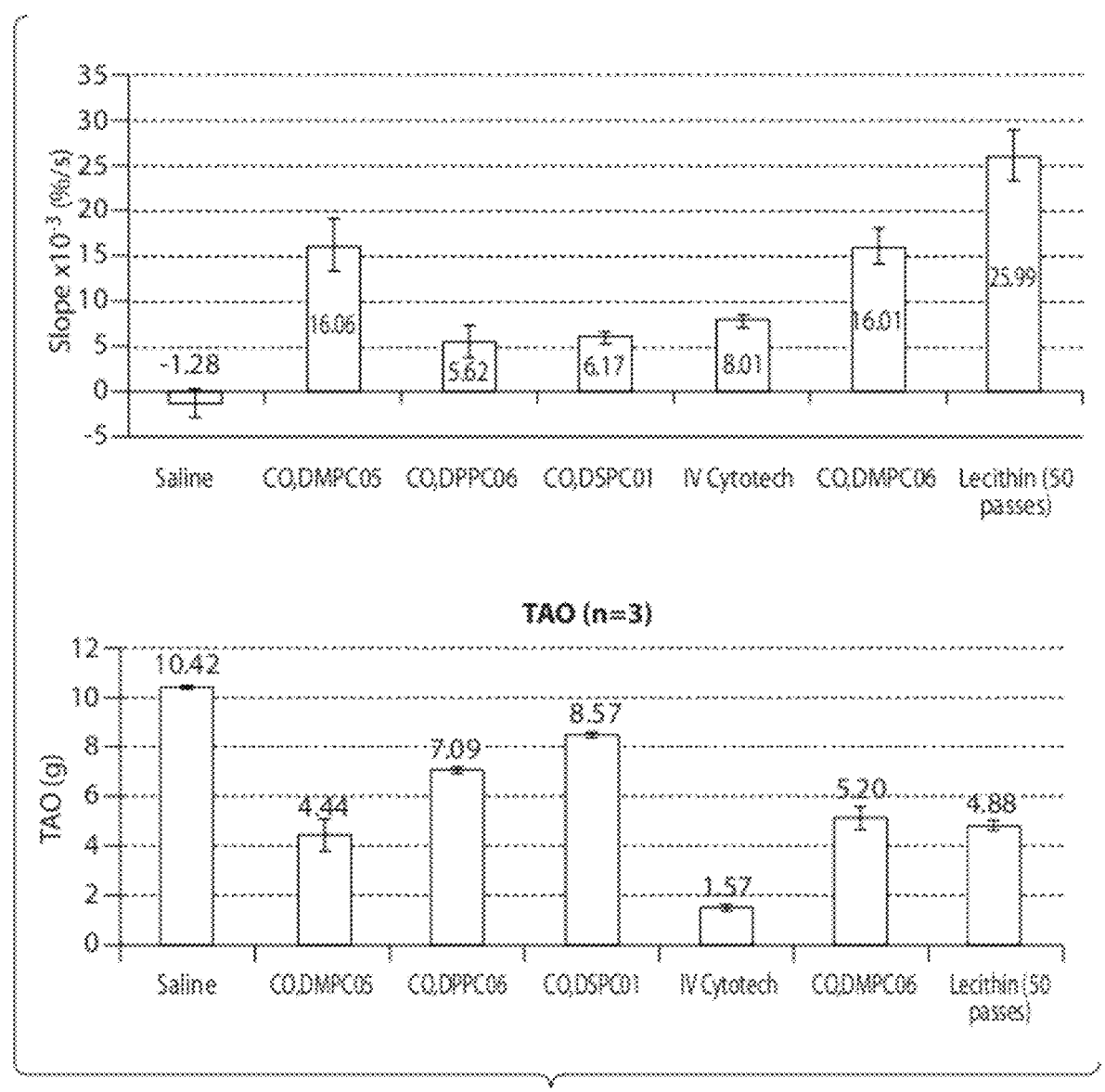
FIGS. 39-41 show further characterization of FIG. 42 shows Table 1.

Comparison of Nebulization Performance Between Aqueous Dispersions of CoQ10 and an Intravenous Formulation In order to more fully understand the effect of the inclusion and amount certain pharmaceutical formulation components on nebulization performance, the continuous aerosolization of several aqueous dispersions of CoQ10 and an intravenous formulation were studied. The results of this example are summarized in FIG. 38, which shows transmittograms of aerosolization of DMPC- and DSPC-stabilized dispersions, as compared to an intravenous formulation that includes a particular opsonisation reducer. Additional data is presented in FIGS. 39-41.

Tested formulations studied included (i) a saline control (0.9% w/w NaCl in water); (ii) Lecithin (50 passes, as presented in Example 1); (iii) CQDPPC06—formulation containing DPPC (4:2.5); (iv) CQDSPC01—formulation containing DSPC (4:2.5); (v) CQDMPC05—formulation containing DMPC (4:2.5); (vi) CQDMPC06—formulation containing DMPC (3:2.5); (vii) IV Cytotech—an intravenous formulation provided by Cytotech Labs for analysis of nebulization performance, including CoQ10:DMPC:Poloxamer 188 (4:3:1.5). Formulations iii-vi were prepared by the method presented in Example 2. Formulation viii was prepared in accordance with the method presented in International Publication Number WO 2011/112900.

Saline, presented a slope close to zero and a high TAO, which indicates successful delivery of the solution using the nebulizer. Dispersion formulations prepared with DMPC (excepting the IV formulation), despite drug concentration differences, presented similar results both for slope and TAO, whereas lecithin (50 passes) presented the highest slope and a comparatively a low TAO. The importance of analyzing both TAO and slope are illustrated by these figures. Although formulations CQDPPC06 and CQDSPC01 presented similar slopes, the TAO from CQDSPC01 was higher than CQDPPC06, showing a higher output despite both being steady nebulized. On the other hand, although the IV formulation presented some nebulization, the aerosol output was the lowest among all formulations. Therefore, for all practical purposes, the IV formulation failed to continuously nebulize in that it could not be reasonably used for delivering a therapeutic dose of the bioactive agent. Formulation CQDSP01 presented the arguably best results among the aqueous dispersions of API 31510. The order of nebulization performance observed was (high to low): DSPC, DPPC, DMPC, lecithin, and IV Cytotech.

Figure 40:
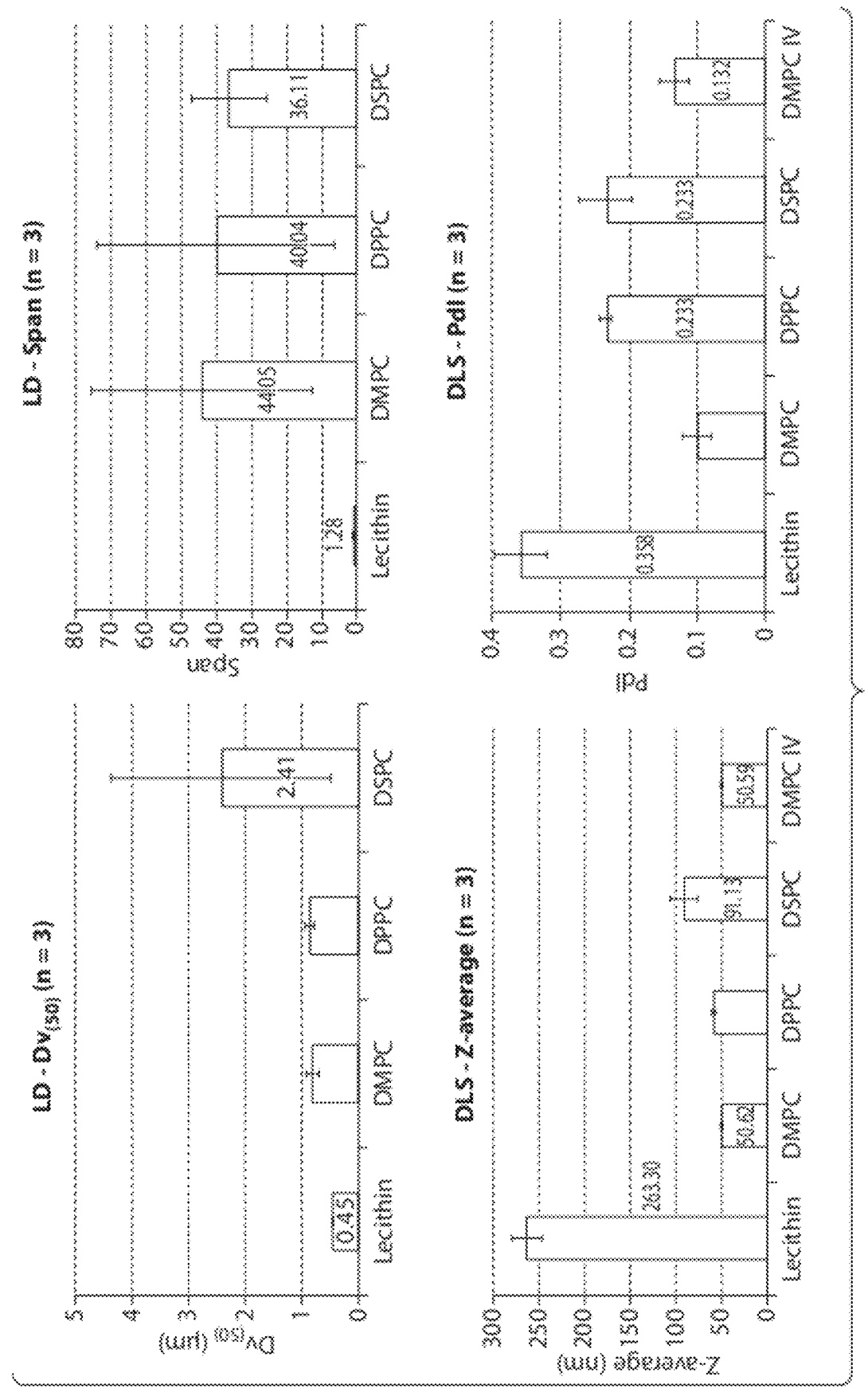

FIG. 40 shows an analysis of drug particles dispersed in the formulations studied in connection with Example 7. Lecithin, DMPC, and DSPC present predominantly submicron sizes, although only lecithin presented a low span. Nevertheless, the lecithin formulation nanoparticles are relatively large (e.g., ~260 nm) and polydisperse (PdI>0.2). The fraction of micron-size particles is largest in the DSPC formulation. The IV formulation presented a monodisperse distribution of ~60 nm particles. The DMPC and DPPC formulations present a mixture of small and large drug particles.

Figure 41:
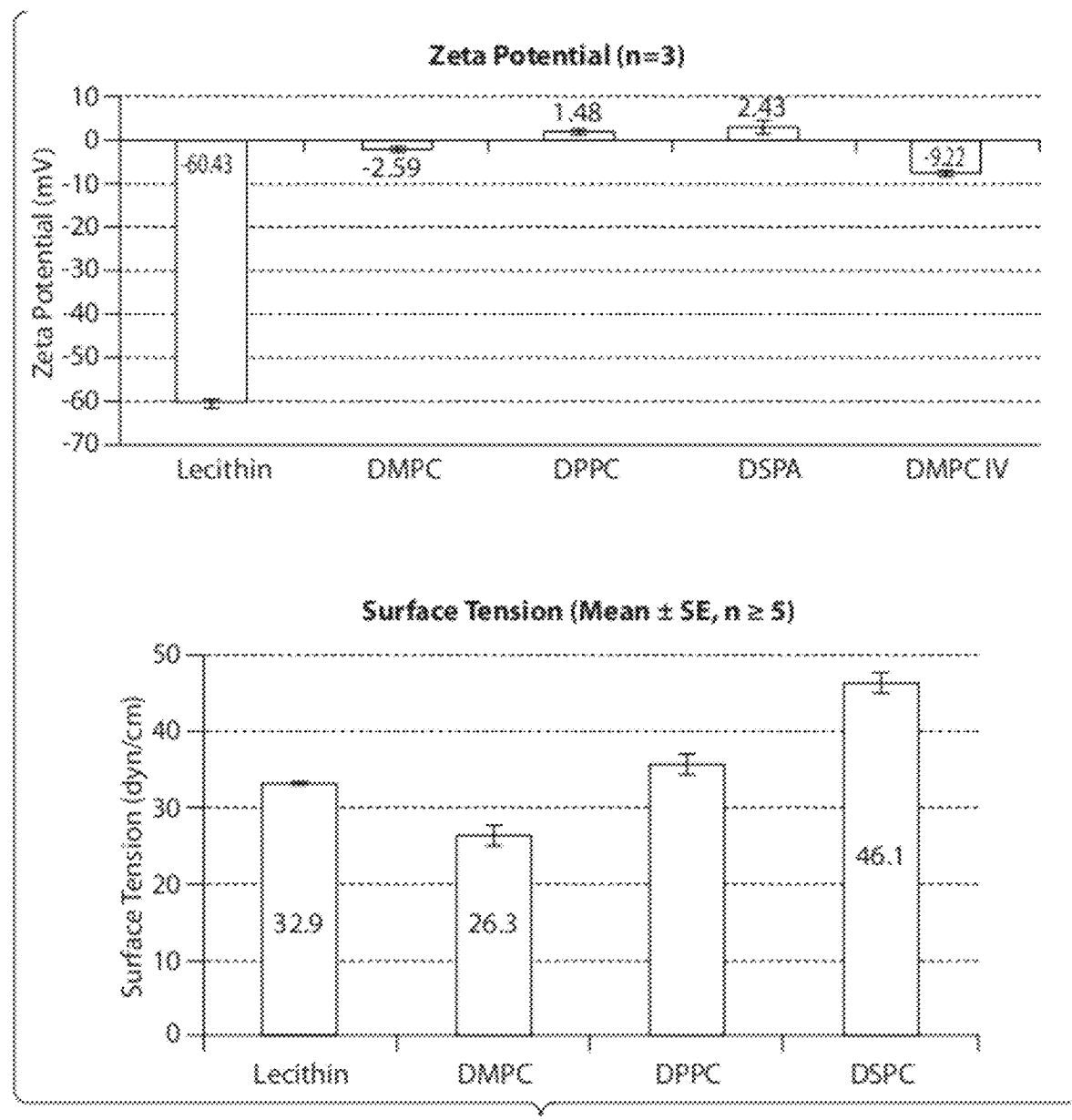

FIG. 41 shows another analysis of drug particles dispersed in the formulations studied in connection with Example 7. The surface charge of drug particles in dispersion was relatively low for the DMPC, DPPC, and DSPC formulations, as reflected by their zeta potential values. The lecithin formulation had the largest zeta potential, despite the lowest phospholipid concentration. The surface tension of the formulations increase with increasing hydrophobicity of synthetic phospholipids (increase in the number of carbons in lipid chain of phospholipids): DMPC<DPPC<DSPC. Interestingly, the surface tension of lecithin, a mixture of phospholipids, falls within the DMPC and DSPC values. However, the mole fractions of the synthetic phospholipids are different because the formulations were prepared by weight (DMPC was the highest and DSPC was the lowest).

Without wishing to be bound by any particular theory, it is believed that the inclusion of poloxamer in the IV formulation was the predominant factor in the IV formulations weak nebulization performance. However, the differences in nebulization can also be potentially attributed to other factors including, but not limited to, the inclusion of PBS rather than saline in the IV formulation, ionic concentration and charge of the formulation (e.g., due to different aqueous dispersion agents and/or the presence of the opsonization reducer), and/or differences in the manufacturing method.

EQUIVALENTS

The specification should be understood as disclosing and encompassing all possible permutations and combinations of the described aspects, embodiments, and examples unless the context indicates otherwise. One of ordinary skill in the art will appreciate that the invention can be practiced by other than the summarized and described aspect, embodiments, and examples, which are presented for purposes of illustration, and that the invention is limited only by the following claims.

Recitation of ranges of values herein is merely intended to serve as a shorthand method of referring individually to each separate value falling within the range. Unless otherwise indicated, each individual value is incorporated into the specification as if it were individually recited. Each of the documents cited herein (including all patents, patent applications, scientific publications, manufacturer's specifications, and instructions), are hereby incorporated by reference in their entirety.

Those skilled in the art will recognize, or be able to ascertain using no more than routine experimentation, many equivalents to the specific embodiments of the invention described herein. Such equivalents are intended to be encompassed by the following claims.

The invention claimed is:

1. An inhalable pharmaceutical composition comprising a dispersion of particles suitable for continuous aerosolization, the composition comprising:
   a dispersion of particles having an average diameter between about 30 and 200 nm, each particle comprising Coenzyme Q10 (CoQ10), DPPC, and an aqueous dispersion vehicle,
   wherein the CoQ10 is about 4% w/w of the composition, the phospholipid is about 2.5% w/w of the composition, and the particles are dispersed within the aqueous dispersion vehicle, and
   wherein, upon administration to a subject, the composition is characterized by continuous aerosolization sufficient to provide a therapeutic dose of CoQ10 to the subject.

2. An inhalable pharmaceutical composition comprising a dispersion of particles suitable for continuous aerosolization, the composition comprising:
   a dispersion of particles having an average diameter between about 30 and 200 nm, each particle comprising Coenzyme Q10 (CoQ10), DSPC, and an aqueous dispersion vehicle,
   wherein the CoQ10 is about 4% w/w of the composition, the phospholipid is about 2.5% w/w of the composition, and the particles are dispersed within the aqueous dispersion vehicle, and
   wherein, upon administration to a subject, the composition is characterized by continuous aerosolization sufficient to provide a therapeutic dose of CoQ10 to the subject.

3. An inhalable pharmaceutical composition comprising a dispersion of particles suitable for continuous aerosolization, the composition comprising:
   a dispersion of particles having an average diameter between about 30 and 200 nm, each particle comprising Coenzyme Q10 (CoQ10), DMPC, and an aqueous dispersion vehicle,
   wherein the CoQ10 is about 4% w/w of the composition, the phospholipid is about 2.5% w/w of the composition, and the particles are dispersed within the aqueous dispersion vehicle, and
   wherein, upon administration to a subject, the composition is characterized by continuous aerosolization sufficient to provide a therapeutic dose of CoQ10 to the subject.

4. An inhalable pharmaceutical composition comprising a dispersion of particles suitable for continuous aerosolization, the composition comprising:
   a dispersion of particles having an average diameter between about 30 and 200 nm, each particle comprising CoQ10, a phospholipid, and an aqueous dispersion vehicle,
   wherein the CoQ10 is about 4% w/w of the composition, the phospholipid is about 2.5% w/w of the composition, and the particles are dispersed within the aqueous dispersion vehicle,
   wherein the phospholipid is DPPC, DSPC, DMPC, or a combination thereof, and
   wherein, upon continuous aerosolization, the composition is capable of achieving a CoQ10 concentration of at least about 500 µg/g wet lung tissue.

5. The inhalable pharmaceutical composition of claim 1, wherein the aqueous dispersion vehicle comprises water or an aqueous salt solution.

6. The inhalable pharmaceutical composition of claim 1, wherein the dispersion of particles is in the form of a continuous respirable aerosol comprising a plurality of aqueous droplets containing a dispersion of particles and having a mass median aerodynamic diameter (MMAD) between about 1 and 5 µm.

7. The inhalable pharmaceutical composition of claim 1, wherein the composition has a polydispersivity index (PDI) of about 0.1, 0.2, 0.3, 0.4, 0.5, 0.6, or 0.7.

8. The inhalable pharmaceutical composition of claim 1, wherein the composition has a total aerosol output (TAO) of at least about 40, 45, 50, 55, 60, 65, 70, 75, 80, 85, 90, 95, or 100%.

9. The inhalable pharmaceutical composition of claim 1, further comprising sodium chloride in an amount less than about 1.0% w/v of the composition.

10. The inhalable pharmaceutical composition of claim 1, further comprising a salt in an amount making the composition essentially isosmotic with the human lung.

11. The inhalable pharmaceutical composition of claim 1, wherein the dispersion is a suspension or an emulsion.

12. The inhalable pharmaceutical composition of claim 1, wherein the continuous aerosolization has a duration of about 1, 2, 3, 4, 5, 6, 7, 8, 9, 10, 11, 12, 13, 14, 15, 20, 25, 30, 35, 40, 50, or 60 minutes.

13. The inhalable pharmaceutical composition of claim 1, further comprising a polyoxypropylene-poloxyethylene block polymer at 0.001-5% by weight of the total composition.

14. The inhalable pharmaceutical composition of claim 1, wherein the dispersion is a nano-suspension or microemulsion.

15. The inhalable pharmaceutical composition of claim 2, wherein the aqueous dispersion vehicle comprises water or an aqueous salt solution.

16. The inhalable pharmaceutical composition of claim 2, wherein the dispersion of particles is in the form of a continuous respirable aerosol comprising a plurality of aqueous droplets containing a dispersion of particles and having a mass median aerodynamic diameter (MMAD) between about 1 and 5 μm.

17. The inhalable pharmaceutical composition of claim 2, wherein the composition has a polydispersivity index (PDI) of about 0.1, 0.2, 0.3, 0.4, 0.5, 0.6, or 0.7.

18. The inhalable pharmaceutical composition of claim 2, wherein the composition has a total aerosol output (TAO) of at least about 40, 45, 50, 55, 60, 65, 70, 75, 80, 85, 90, 95, or 100%.

19. The inhalable pharmaceutical composition of claim 2, further comprising sodium chloride in an amount less than about 1.0% w/v of the composition.

20. The inhalable pharmaceutical composition of claim 2, further comprising a salt in an amount making the composition essentially isosmotic with the human lung.

21. The inhalable pharmaceutical composition of claim 2, wherein the dispersion is a suspension or an emulsion.

22. The inhalable pharmaceutical composition of claim 2, wherein the continuous aerosolization has a duration of about 1, 2, 3, 4, 5, 6, 7, 8, 9, 10, 11, 12, 13, 14, 15, 20, 25, 30, 35, 40, 50, or 60 minutes.

23. The inhalable pharmaceutical composition of claim 2, further comprising a polyoxypropylene-poloxyethylene block polymer at 0.001-5% by weight of the total composition.

24. The inhalable pharmaceutical composition of claim 3, wherein the aqueous dispersion vehicle comprises water or an aqueous salt solution.

25. The inhalable pharmaceutical composition of claim 3, wherein the dispersion of particles is in the form of a continuous respirable aerosol comprising a plurality of aqueous droplets containing a dispersion of particles and having a mass median aerodynamic diameter (MMAD) between about 1 and 5 μm.

26. The inhalable pharmaceutical composition of claim 3, wherein the composition has a polydispersivity index (PDI) of about 0.1, 0.2, 0.3, 0.4, 0.5, 0.6, or 0.7.

27. The inhalable pharmaceutical composition of claim 3, wherein the composition has a total aerosol output (TAO) of at least about 40, 45, 50, 55, 60, 65, 70, 75, 80, 85, 90, 95, or 100%.

28. The inhalable pharmaceutical composition of claim 3, further comprising sodium chloride in an amount less than about 1.0% w/v of the composition.

29. The inhalable pharmaceutical composition of claim 3, further comprising a salt in an amount making the composition essentially isosmotic with the human lung.

30. The inhalable pharmaceutical composition of claim 3, wherein the dispersion is a suspension or an emulsion.

31. The inhalable pharmaceutical composition of claim 3, wherein the continuous aerosolization has a duration of about 1, 2, 3, 4, 5, 6, 7, 8, 9, 10, 11, 12, 13, 14, 15, 20, 25, 30, 35, 40, 50, or 60 minutes.

32. The inhalable pharmaceutical composition of claim 3, further comprising a polyoxypropylene-poloxyethylene block polymer at 0.001-5% by weight of the total composition.

33. A method for preparing an inhalable pharmaceutical composition comprising the steps of:
hydrating a phospholipid, thereby forming a hydrated phospholipid;
mixing the hydrated phospholipid, CoQ10, and an aqueous dispersion vehicle, thereby producing a mixture; and
homogenizing the mixture, thereby producing a dispersion of particles comprising the phospholipid and CoQ10 dispersed within the aqueous dispersion vehicle and having an average diameter between about 30 and 200,
wherein the CoQ10 is about 4% w/w of the composition, and the phospholipid is about 2.5% w/w of the composition,
wherein the phospholipid is DPPC, DSPC, DMPC, or a combination thereof, and
wherein, upon administration to a subject, the composition is characterized by continuous aerosolization sufficient to provide a therapeutic dose of CoQ10 to the subject.

34. The method of claim 33, further comprising:
aerosolizing the dispersion of particles, thereby forming a respirable aerosol comprising a plurality of droplets, each droplet comprising a dispersion of particles and having a mass median aerodynamic diameter (MMAD) between about 1 and 5 μm.

35. The method of claim 33, wherein mixing comprises high shear mixing for up to about 5 minutes at about 10,000 to 20,000 rpm and at about 50 to 65° C.

36. The method of claim 33, wherein homogenizing comprises microfluidization.

37. The method of claim 33, wherein homogenizing comprises high pressure homogenization for about 1-50 passes at about 30,000 psi and at about 50 to 65° C.

38. The method of claim 33, wherein homogenizing comprises ultrasonic homogenization.

39. The method of claim 33, wherein aerosolization comprises vibrating mesh nebulization.

40. A method for administering an inhalable pharmaceutical composition comprising the steps of:
aerosolizing a dispersion of particles, thereby forming a respirable aerosol comprising a plurality of droplets having a mass median aerodynamic diameter (MMAD) between about 1 and 5 μm,
wherein the dispersion of particles has an average diameter between about 30 and 200 nm, each particle comprising Coenzyme Q10 (CoQ10) and a phospholipid dispersed within an aqueous dispersion vehicle,
wherein the CoQ10 is about 4% w/w of the composition, and the phospholipid is about 2.5% w/w of the composition; and
wherein the phospholipid is DPPC, DSPC, DMPC, or a combination thereof,
wherein, upon administration to a subject, the composition is characterized by continuous aerosolization sufficient to provide a therapeutic dose of CoQ10 to the subject; and
delivering a therapeutically effective amount of CoQ10 to a lung of a subject in need of treatment.

41. The method of claim 40, wherein aerosolization comprises vibrating mesh nebulization.

42. The method of claim 40, wherein the aerosol is characterized by an APT between about 50 and 100% over at least 15 minutes of continuous aerosolization.

43. The method of claim 40, wherein the aerosol is characterized by an APT between about 50 and 100%, between about 60 and 100%, between about 70 and 100%, between about 80 and 100%, or between about 90 and 100%.

44. The method of claim 40, wherein the plurality of droplets has a MMAD between about 1 and 5 μm over at least 15 minutes of continuous aerosolization.

45. The method of claim 40, wherein the MMAD is about 1, 2, 3, 4, or 5 μm.

46. The method of claim 40, wherein the droplets have a geometric standard deviation (GSD) of at least about 2.0.

47. The method of claim 40, wherein delivery achieves a mass fraction deposited of at least about 1, 5, 10, 15, or 20%.

48. The method of claim 40, wherein delivery achieves local delivery to the lung substantially without systemic delivery.

49. The method of claim 40, wherein delivery achieves an elevated amount of the CoQ10 in the lung for at least 48 hours after administration.

50. The method of claim 40, wherein, upon continuous aerosolization, the composition is capable of achieving a CoQ10 concentration of at least about 500 μg/g wet lung tissue.

51. The method of claim 40, wherein delivering a therapeutically effective amount of the CoQ10 comprises metering a dose of the CoQ10.

52. The method of claim 40, wherein the subject has lung cancer.

53. The method of claim 40, wherein the subject has one or more of asthma, allergies, chronic obstructive pulmonary disease, chronic bronchitis, acute bronchitis, emphysema, cystic fibrosis, pneumonia, tuberculosis, pulmonary edema, acute respiratory distress syndrome, pneumoconiosis, interstitial lung disease, pulmonary edema, pulmonary embolism, pulmonary hypertension, pleural effusion, pneumothorax, mesothelioma, amyotrophic lateral sclerosis, and myasthenia gravis.

54. An inhalable pharmaceutical composition prepared by a process comprising the steps of:
hydrating a phospholipid, thereby forming a hydrated phospholipid;
mixing the hydrated phospholipid, Coenzyme Q10 (CoQ10), and an aqueous dispersion vehicle, thereby producing a mixture; and
homogenizing the mixture, thereby producing a dispersion of particles comprising the phospholipid and CoQ10 dispersed within the aqueous dispersion vehicle and having an average diameter between about 30 and 200 nm,
wherein the CoQ10 is about 4% w/w of the composition, and the phospholipid is about 2.5% w/w of the composition; and
wherein the phospholipid is DPPC, DSPC, DMPC, or a combination thereof, and
wherein, upon administration to a subject, the composition is characterized by continuous aerosolization sufficient to provide a therapeutic dose of CoQ10 to the subject.

55. An inhalable pharmaceutical composition comprising a dispersion of particles suitable for continuous aerosolization, the composition comprising:
a dispersion of particles having an average diameter between about 30 and 200 nm, each particle comprising Coenzyme Q10 (CoQ10), a phospholipid, and an aqueous dispersion vehicle,
wherein the CoQ10 is about 4% w/w of the composition, and the phospholipid is about 2.5% w/w of the composition, and the particles are dispersed within the aqueous dispersion vehicle;
wherein the phospholipid is DPPC, DSPC, DMPC, or a combination thereof, and
wherein, upon continuous aerosolization, the composition is capable of achieving a total emitted dose (TED) of at least about 2,900 μg over 15 seconds.

56. The inhalable pharmaceutical composition of claim 55, wherein the TED is at least about 3,600, 3,900, 4,300, or 4,600 μg over 15 seconds.

\* \* \* \* \*